US010005720B2

(12) United States Patent
Sexton et al.

(10) Patent No.: US 10,005,720 B2
(45) Date of Patent: Jun. 26, 2018

(54) COMPOUNDS USEFUL FOR THE TREATMENT OF METABOLIC DISORDERS AND SYNTHESIS OF THE SAME

(71) Applicants: NORTH CAROLINA CENTRAL UNIVERSITY, Durham, NC (US); The University of North Carolina at Chapel Hill, Chapel Hill, NC (US)

(72) Inventors: Jonathan Z. Sexton, Raleigh, NC (US); Jay E. Brenman, Chapel Hill, NC (US); David L. Musso, Raleigh, NC (US)

(73) Assignees: North Carolina Central University, Durham, NC (US); The University of North Carolina at Chapel Hill, Chapel Hill, NC (US)

( * ) Notice: Subject to any disclaimer, the term of this patent is extended or adjusted under 35 U.S.C. 154(b) by 0 days. days.

(21) Appl. No.: 14/782,415

(22) PCT Filed: Apr. 4, 2014

(86) PCT No.: PCT/US2014/033065
§ 371 (c)(1),
(2) Date: Oct. 5, 2015

(87) PCT Pub. No.: WO2014/165816
PCT Pub. Date: Oct. 9, 2014

(65) Prior Publication Data
US 2016/0046560 A1 Feb. 18, 2016

Related U.S. Application Data

(60) Provisional application No. 61/808,939, filed on Apr. 5, 2013.

(51) Int. Cl.
*C07C 235/64* (2006.01)
*A61K 45/06* (2006.01)
*C07C 255/60* (2006.01)
*C07C 233/66* (2006.01)
*C07C 233/81* (2006.01)
*C07C 235/68* (2006.01)
*C07D 213/75* (2006.01)
*C07D 213/82* (2006.01)
*C07D 249/08* (2006.01)
*C07D 257/04* (2006.01)
*C07D 271/06* (2006.01)
*C07D 295/155* (2006.01)
*A61K 31/167* (2006.01)
*A61K 31/196* (2006.01)
*A61K 31/245* (2006.01)
*A61K 31/277* (2006.01)
*A61K 31/40* (2006.01)
(Continued)

(52) U.S. Cl.
CPC .......... *C07C 235/64* (2013.01); *A61K 31/167* (2013.01); *A61K 31/196* (2013.01); *A61K 31/245* (2013.01); *A61K 31/277* (2013.01); *A61K 31/40* (2013.01); *A61K 31/44* (2013.01); *A61K 31/5375* (2013.01); *A61K 45/06* (2013.01); *C07C 45/46* (2013.01); *C07C 67/39* (2013.01); *C07C 231/02* (2013.01); *C07C 233/66* (2013.01); *C07C 233/81* (2013.01); *C07C 235/68* (2013.01); *C07C 253/30* (2013.01); *C07C 255/60* (2013.01); *C07D 207/34* (2013.01); *C07D 213/75* (2013.01); *C07D 213/82* (2013.01); *C07D 249/08* (2013.01); *C07D 257/04* (2013.01); *C07D 271/06* (2013.01); *C07D 295/155* (2013.01); *C07C 2601/14* (2017.05)

(58) Field of Classification Search
CPC .................................................... C07C 235/64
See application file for complete search history.

(56) References Cited

U.S. PATENT DOCUMENTS 7,189,715 B2    3/2007  Jerussi et al.
2003/0124157 A1  7/2003  Engles et al.
(Continued)

FOREIGN PATENT DOCUMENTS

WO    WO 97/10224 A1    3/1997
WO    WO 02/06234 A1    1/2002
(Continued)

OTHER PUBLICATIONS

Registry No. 1405849-02-6, File Registry on STN, Nov. 25, 2012.*
Sexton et al. "High content screening for nonclassical peroxisome proliferators", *Int. J. High Throughput Screening* 1:127-140 (2010).
Notification of Transmittal of the International Search Report and the Written Opinion of the International Searching Authority, or the Declaration corresponding to International Application No. PCT/US14/33065 dated Aug. 27, 2014.
Notification Concerning Transmittal of International Preliminary Report on Patentability corresponding to International Application No. PCT/US14/33065 dated Oct. 15, 2015.

*Primary Examiner* — Rebecca L Anderson
(74) *Attorney, Agent, or Firm* — Ward and Smith, P.A.

(57) ABSTRACT

The present invention provides compounds of Formula (I): wherein variables X, Y, Z and R1 are as described herein. Some of the compounds described herein are glutamate dehydrogenase activators. The invention is also directed to pharmaceutical compositions comprising these compounds, uses of these compounds and compositions in the treatment of metabolic disorders as well as synthesis of the compounds.

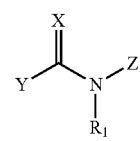

(I)

20 Claims, 7 Drawing Sheets

(51) Int. Cl.
  *A61K 31/44* (2006.01)
  *A61K 31/5375* (2006.01)
  *C07C 45/46* (2006.01)
  *C07C 67/39* (2006.01)
  *C07C 231/02* (2006.01)
  *C07C 253/30* (2006.01)
  *C07D 207/34* (2006.01)

(56) References Cited

U.S. PATENT DOCUMENTS

| | | |
|---|---|---|
| 2009/0186879 A1 | 7/2009 | Aso et al. |
| 2009/0239919 A1* | 9/2009 | Wood .................... C07C 235/64 514/371 |
| 2010/0292143 A1 | 11/2010 | Bhuniya et al. |

FOREIGN PATENT DOCUMENTS

| | | |
|---|---|---|
| WO | WO 02/20500 A2 | 3/2002 |
| WO | WO 2004/039365 A1 | 5/2004 |
| WO | WO 2004/041266 A1 | 5/2004 |
| WO | WO 2004/048363 A1 | 6/2004 |
| WO | WO 2004/082601 A2 | 9/2004 |
| WO | WO 2004/106276 A1 | 12/2004 |
| WO | WO 2005/030740 A1 | 4/2005 |
| WO | WO 2005/058823 A1 | 6/2005 |
| WO | WO 2005/063725 A1 | 7/2005 |
| WO | WO 2005/063729 A1 | 7/2005 |
| WO | WO 2005/087710 A1 | 9/2005 |
| WO | WO 2005/095338 A1 | 10/2005 |
| WO | WO 2005/110996 A1 | 11/2005 |
| WO | WO 2005/113504 A1 | 12/2005 |
| WO | WO 2006/112549 A1 | 10/2006 |
| WO | WO 2007/013689 A1 | 2/2007 |
| WO | WO 2007/013694 A1 | 2/2007 |
| WO | WO 2007/018314 A2 | 2/2007 |
| WO | WO 2007/028135 A2 | 3/2007 |
| WO | WO 2008/001931 A2 | 1/2008 |
| WO | WO 2008/047821 A1 | 4/2008 |
| WO | WO 2008/050821 A1 | 5/2008 |
| WO | WO 2008/093639 A1 | 8/2008 |
| WO | WO 2008/099794 A1 | 8/2008 |
| WO | WO 2008/136428 A1 | 11/2008 |
| WO | WO 2008/156757 A1 | 12/2008 |
| WO | WO 2010/101648 A1 | 9/2010 |
| WO | WO 2011/088201 A1 | 7/2011 |
| WO | WO 2012/068274 A1 | 5/2012 |
| WO | WO 2012/125893 A1 | 9/2012 |

* cited by examiner

| B-127443 | | Markush Structure | | |
|---|---|---|---|---|
| Compound | R1 | R3 | R4 | FGF21 |
| B-127443 | Cl– | –NO₂ | –OH | 3.5 |
| B-500199 | (none) | –C(O)OCH₃ | –OH | 11.0 |
| B-500200 | (none) | –C(O)OH | –OH | 3.1 |
| B-500845 | –CF₃ | –C(O)OH | –OH | 4.6 |
| B-500828 | –CH(CH₃)₂ (isopropyl) | –C(O)OCH₃ | –OH | 2.5 |
| B-500203 | Scaffold Change | | | 3.5 |
| DMSO | Negative Control | | | 1.0 |

FIG. 1

Fig. 2. Generalized reaction scheme for generating analogs containing ester or acid groups in the aniline R3-position.

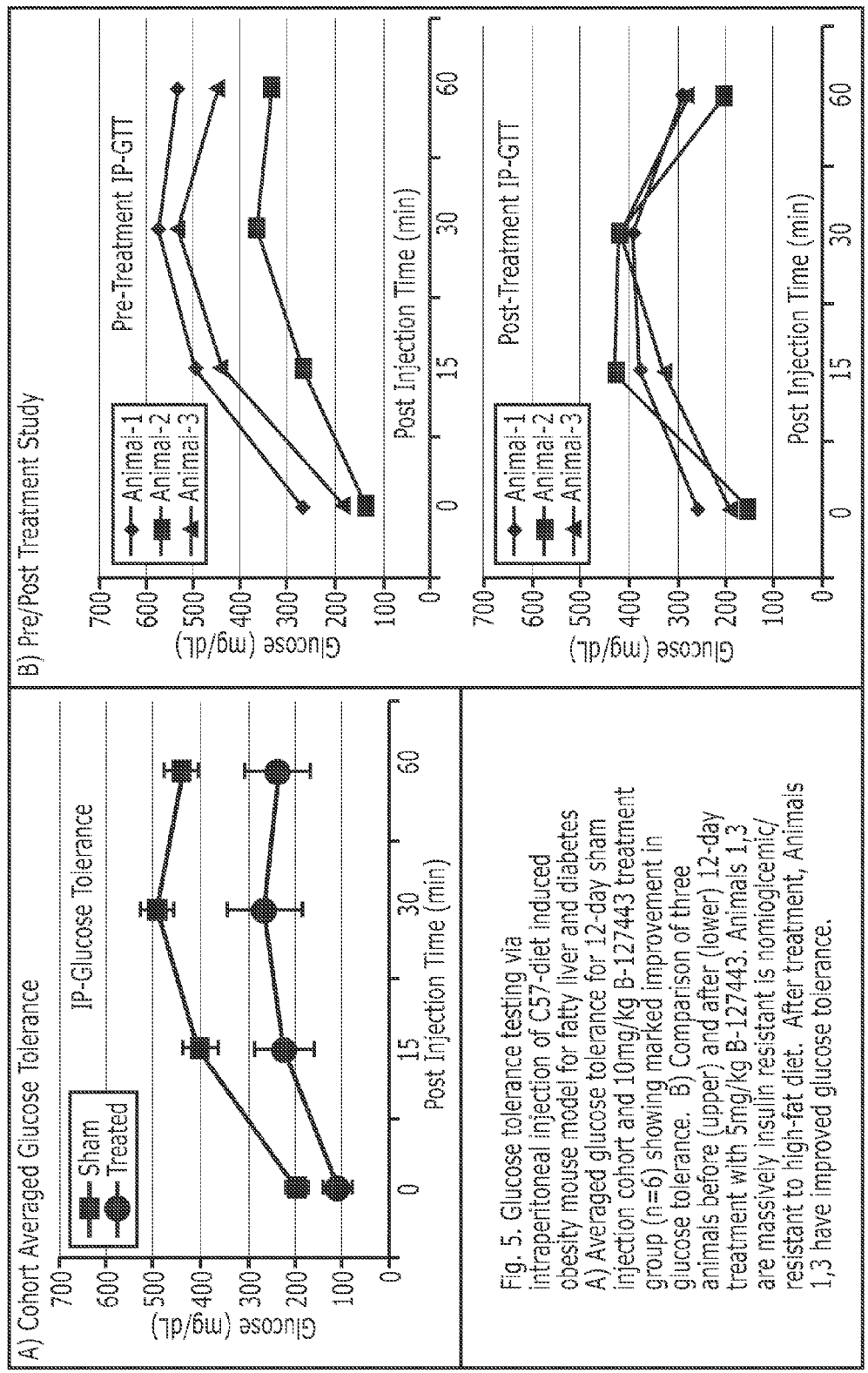

FIG. 5

Fig. 5. Glucose tolerance testing via intraperitoneal injection of C57-diet induced obesity mouse model for fatty liver and diabetes A) Averaged glucose tolerance for 12-day sham injection cohort and 10mg/kg B-127443 treatment group (n=6) showing marked improvement in glucose tolerance. B) Comparison of three animals before (upper) and after (lower) 12-day treatment with 5mg/kg B-127443. Animals 1,3 are massively insulin resistant is normoglicemic/resistant to high-fat diet. After treatment, Animals 1,3 have improved glucose tolerance.

COMPOUNDS USEFUL FOR THE TREATMENT OF METABOLIC DISORDERS AND SYNTHESIS OF THE SAME

STATEMENT OF PRIORITY

This application is a 35 U.S.C. § 371 national phase application of PCT Application No. PCT/US2014/033065 filed Apr. 4, 2014, which claims benefit of U.S. Provisional Application No. 61/808,939 filed Apr. 5, 2013, the entire contents of each of which is incorporated by reference herein.

STATEMENT OF GOVERNMENT SUPPORT

This invention was made with government support under grant number IR43DK093345-01 from the NIH/National Institute of Diabetes and Digestive and Kidney Diseases. The government has certain rights to this invention.

FIELD OF THE INVENTION

The present invention relates to novel compounds and synthesis thereof and compositions including the compounds as well methods for treating metabolic disorders.

BACKGROUND OF THE INVENTION

Non-alcoholic fatty liver disease (NAFLD) includes related disorders ranging from mild hepatic steatosis to non-alcoholic steatohepatitis (NASH), potentially progressing to fibrosis or liver cirrhosis (Cohen et al., Science, 2011, 332, 1519-1523). NAFLD affects nearly one-third of US adults (Schuppan et al., Liver Int., 2010, 30, 795-808) and is the most common chronic liver disease in both US children and adults (Lavine et al., JAMA, 2011, 305, 1659-68). Deposition of triglycerides in the cytoplasm of 5-10% of hepatocytes defines mild fatty liver disease. Like many burgeoning metabolic diseases, including type 2 diabetes (T2D), NAFLD associates with obesity and insulin resistance and likely reflects the liver's manifestation of metabolic syndrome (Schuppan et al., Liver Int., 2010, 30, 795-808). Indeed, 50-60% of patients with T2D have NAFLD (Smith et al., Nat. Rev. Endocrinol., 2011, 7, 456-465). First line therapy for fatty liver disease includes weight loss, dietary changes and exercise; however, for most patients these interventions prove therapeutically insufficient and/or difficult to maintain. Currently, there is no FDA-approved small molecule treatment for NAFLD.

Despite being the most common chronic liver disease, accounting for 60-90% of abnormal liver blood tests (Day, Clin. Med., 2011, 11, 176-178), there is no widely implemented, treatment for NAFLD ("No treatment has been established" [Lavine et al., JAMA, 2011, 305, 1659-68; Sanyal, et al., N. Engl. J. Med., 2010, 362, 1675-1685]). While the molecular pathogenesis of NAFLD remains unclear (Cohen et al., Science, 2011, 332, 1519-1523), the predominant hepatic phenotype is cytoplasmic triglyceride accumulation. Although no clinically validated molecular target for treating NAFLD exists, small molecules that eliminate ("clear") excess triglycerides from the liver may lead to novel treatments for NAFLD.

SUMMARY OF THE INVENTION

Embodiments of present invention are directed to compounds of Formula (I):

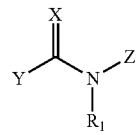

wherein variables Y, X, $R_1$ and Z are as described herein.

Embodiments of the present invention further include compounds of Formula (I):

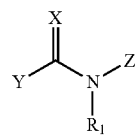

wherein:
X is O or S;
$R_1$ is selected from the group consisting of hydrogen, alkyl, araalkyl, cycloalkyl, and aryl, wherein said alkyl, araalkyl, cycloalkyl and aryl groups can be optionally substituted with one to five substituents selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol;
Y and Z are each independently aryl or heterocycle;
wherein aryl is selected from the group consisting of azulenyl, indanyl, indenyl, naphthyl, phenyl, and tetrahydronaphthyl; heterocycle is selected from the group consisting of benzimidazolyl, benzopyranyl, benzofuranyl, benzothiazolyl, benzoxazolyl, chromanyl, 1,3-dioxolanyl, furanyl, imidazolinyl, imidazolyl, indazolyl, indolinyl, indolyl, isoindolinyl, isoindolyl, isoquinolinyl, isothiazolyl, isoxazolyl, naphthyridinyl, oxadiazolyl, oxazolyl, purinyl, pyridyl, pyrimidinyl, pyrazinyl, pyrazolyl, pyridazinyl, pyrrolyl, quinazolinyl, quinolinyl, quinoxalinyl, tetrahydroisoquinolinyl, tetrahydroquinolinyl, tetrazolyl, thiazolinyl, thiazolyl, triazine, and thienyl; wherein aryl and heterocycle is unsubstituted or substituted with one to seven substituents each independently selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, trifluoromethyl and thiol; and wherein the substituent can be optionally substituted with one to five substituents selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocycle, heteroaryl, hydroxy, nitro, oxo, oxy, peptide, sulfone, sulfoxide, and thiol; or an individual enantiomer, diastereomer, pharmaceutically acceptable salt or prodrug thereof.

In some embodiments of Formula (I),
X is O or S;
$R_1$ is selected from:
(1) hydrogen,
(2) $C_{1-6}$ alkyl, which is unsubstituted or substituted with 1-5 substituents each independently selected from:

(a) halo,
(b) $C_{3-6}$ cycloalkyl,
(c) $CF_3$,
(d) $OR^a$
(3) $C_{3-6}$ cycloalkyl,
(4) araalkyl, and
(5) phenyl;
wherein Y and Z are each independently aryl or heterocycle; wherein the heterocycle is defined above and which aryl or heterocycle is unsubstituted or substituted with 1-7 substituents each independently selected from:
(a) halo,
(b) $C_{1-6}$ alkyl,
(c) $OR^a$,
(d) $NO_2$,
(e) CN,
(f) $NR^bR^c$,
(g) $OCO_2R^e$,
(h) $CO_2R^a$,
(i) $C(=O)R^a$,
(j) $C(=O)NR^bR^c$,
(k) $S(O)_dR^e$,
(m) $N(R^b)SO_2R^e$,
(n) $N(R^b)CO_2R^a$,
(o) $N(R^b)C(=O)R^a$,
(p) $OCOR^e$,
$R^a$ is independently selected from:
(1) hydrogen, or
(2) $C_{1-6}$alkyl, which is unsubstituted or substituted with 1-7 substituents each independently selected from:
(a) halo,
(b) O—$C_{1-6}$ alkyl, which is unsubstituted or substituted with 1-6 halo,
(c) hydroxyl,
(d) CN, and
(e) aryl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine, and pyrazinyl, which aryl or heterocycle is unsubstituted or substituted with 1-7 substituents each independently selected from:
(i) halo,
(ii) O—$C_{1-6}$ alkyl, which is unsubstituted or substituted with 1-6 halo,
(iii) CN,
(iv) nitro,
(v) hydroxyl, and
(vi) $C_{1-6}$ alkyl, which is unsubstituted or substituted with 1-6 halo;
$R^b$ and $R^c$ are independently selected from:
(1) hydrogen, or
(2) $C_{1-6}$ alkyl, which is unsubstituted or substituted with 1-7 substituents each independently selected from:
(a) halo,
(b) $OR^a$,
(c) CN,
(d) $CO_2R^a$,
(e) aryl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuryl, tetrahydropyranyl, triazine, and pyrazinyl, which aryl or heterocycle is unsubstituted or substituted with 1-7 substituents each independently selected from:
(i) halo,
(ii) $OR^a$,
(iii) $C_{1-6}$ alkyl, which is unsubstituted or substituted with 1-6 halo, and
(iv) nitro;
$R^e$ is independently selected from:
(1) $C_{1-6}$ alkyl, which is unsubstituted or substituted with 1-4 substituents each independently selected from:
(a) halo,
(b) $OR^a$,
(c) $CO_2R^a$,
(d) CN, and
(e) aryl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) $OR^a$,
(iii) $C_{1-6}$ alkyl, which is unsubstituted or substituted with 1-6 halo, and
(iv) nitro;
d is 0, 1, or 2; or
an individual enantiomer, diastereomer, pharmaceutically acceptable salt or prodrug thereof.
In some embodiments of Formula (I), X is O.
In some embodiments of Formula (I), X is O and $R_1$ is hydrogen.
In some embodiments of Formula (I);
X is O or S;
$R_1$ is as defined above;
wherein:
Y and Z are each independently selected from one of the following:

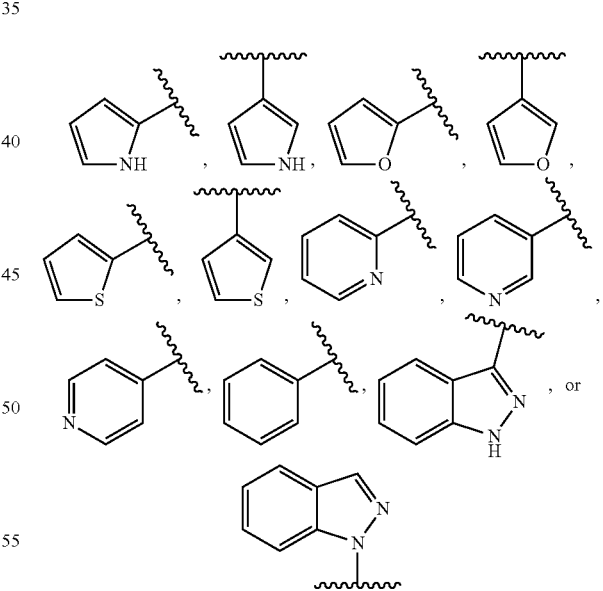

wherein Y and Z are each independently unsubstituted or substituted with 1-5 substituents each independently selected from:
(a) halo,
(b) $C_{1-6}$ alkyl, which is unsubstituted or substituted with 1-5 halo,
(c) $OR^a$,
(d) $NO_2$,
(e) CN, (f) NR$^b$R$^c$,
(g) OCO$_2$R$^e$,
(h) CO$_2$R$^a$,
(i) C(=O)R$^a$,
(j) C(=O)NR$^b$R$^c$,
(k) S(O)$_d$R$^e$,
(m) N(R$^b$)SO$_2$R$^e$,
(n) N(R$^b$)CO$_2$R$^a$,
(o) N(R$^b$)C(=O)R$^a$, and
(p) OCOR$^e$,
wherein:
R$^a$, R$^b$, R$^c$, R$^e$ are as defined above;
d is 0, 1, or 2; or
an individual enantiomer, diastereomer, pharmaceutically acceptable salt or prodrug thereof.

In some embodiments, the present invention provides compounds of Formula (II):

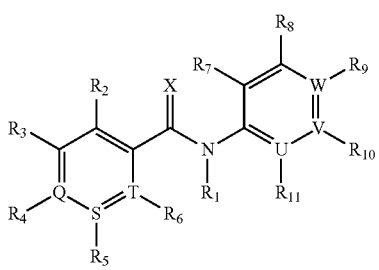

(II)

wherein:
X is O or S;
Q, S, T, U, V, and W are CH or N;
R$_1$ is as defined above, R$_2$, R$_4$, R$_5$, R$_7$, R$_8$, and R$_{10}$ are H;
R$_3$ is selected from the group consisting of hydrogen, C$_{1-6}$ alkyl, which is unsubstituted or substituted with 1-5 halo, halo, and OR$^a$;
R$_6$ is selected from the group consisting of hydrogen, OR$^a$, NO$_2$, and OC(O)R$^e$;
R$_9$ is selected from the group consisting of hydrogen, C$_{1-6}$ alkyl, which is unsubstituted or substituted with 1-5 halo; CO$_2$R$^a$, C(=O)NR$^b$R$^c$, NO$_2$, OR$^a$, halo, and CN;
R$_{11}$ is selected from the group consisting of hydrogen, halo, OR$^a$, and C$_{1-6}$ alkyl, which is unsubstituted or substituted with 1-5 halo;
wherein:
R$^a$, R$^b$, R$^c$, R$^e$ are as defined above; or
an individual enantiomer, diastereomer, pharmaceutically acceptable salt or prodrug thereof.

In some embodiments of Formula (II), X is O.
In some embodiments of Formula (II), X is O and R$_1$ is H;
In some embodiments, the present invention provides compounds of Formula (III):

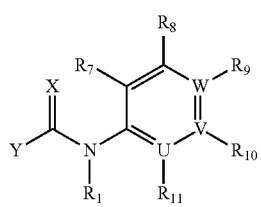

(III)

wherein:
X is O or S;
Y is pyrrole;

wherein said pyrrole is unsubstituted or substituted with one to four substituents each independently selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol; and wherein said substituent can be optionally substituted with one to five substituents selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol;
U, V, and W are CH or N;
R$_7$, R$_8$, and R$_{10}$ are H;
R$_9$ is selected from the group consisting of hydrogen, C$_{1-6}$ alkyl, which is unsubstituted or substituted with 1-5 halo; CO$_2$R$^a$, C(=O)NR$^b$R$^c$, NO$_2$, OR$^a$, halo, and CN;
R$_{11}$ is selected from the group consisting of hydrogen, halo, OR$^a$, and C$_{1-6}$ alkyl, which is unsubstituted or substituted with 1-5 halo;
R$_1$, R$^a$, R$^b$ and R$^c$ are as defined above; and
an individual enantiomer, diastereomer, pharmaceutically acceptable salt or prodrug thereof.

Also provided are compounds of Formula (IV):

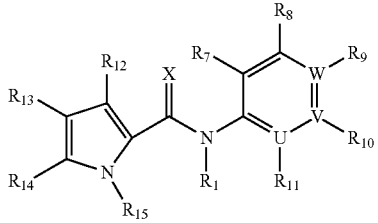

(IV)

wherein:
X is O or S;
U, V, and W are CH or N;
R$_7$, R$_8$, and R$_{10}$ are H;
R$_9$ is selected from the group consisting of hydrogen, C$_{1-6}$ alkyl, which is unsubstituted or substituted with 1-5 halo; CO$_2$R$^a$, C(=O)NR$^b$R$^c$, NO$_2$, OR$^a$, halo, and CN;
R$_{11}$ is selected from the group consisting of hydrogen, halo, OR$^a$, and C$_{1-6}$ alkyl, which is unsubstituted or substituted with 1-5 halo;
R$_{12}$, R$_{13}$, R$_{14}$ is selected from the group consisting of hydrogen, halo, C$_{1-6}$ alkyl, OR$^a$, NO$_2$, CN, NR$^b$R$^c$, OCO$_2$R$^e$, CO$_2$R$^a$, C(=O)R$^a$, C(=O)NR$^b$R$^c$, S(O)$_d$R$^e$, N(R$^b$)SO$_2$R$^e$, N(R$^b$)CO$_2$R$^a$, N(R$^b$)C(=O)R$^a$, and OCOR$^e$;
R$_{15}$ is selected from:
(1) hydrogen,
(2) C$_{3-6}$ alkyl, which is unsubstituted or substituted with 1-5 substituents each independently selected from:
(a) halo,
(b) C$_{3-6}$ cycloalkyl,
(c) CF$_3$,
(d) OR$^a$
(3) C$_{3-6}$ cycloalkyl,
(4) araalkyl, and
(5) phenyl;
wherein:
R$^a$, R$^b$, R$^c$, R$_d$ and R$^e$ are as defined above.
In some embodiments of Formula IV, X is O.
In some embodiments, the compounds described herein are glutamate dehydrogenase activators. These compounds may be useful in the treatment or prevention of diseases in which glutamate dehydrogenase is involved, for example, fatty liver disease. Embodiments of the present invention are also directed to pharmaceutical compositions comprising the compounds described as well as the use of these compounds and compositions in the prevention or treatment of various diseases, such as diseases in which glutamate dehydrogenase is involved, diabetes, fatty liver disease, and use for pancreatic beta-cell regeneration. A further embodiment of the present invention is the use of the compound or composition as described herein for carrying out a method as described herein, and/or for the preparation of a medicament for carrying out a method as described herein.

BRIEF DESCRIPTION OF THE DRAWINGS

FIG. 1 depicts a tabulated analysis of dose response results in a bioassay panel. Lead molecule B-127443, R-group/Markush structure and SAR table for 6 selected compounds showing active substitutions and FGF21 fold-change simulation in human liver cells.

FIG. 5 shows results of glucose tolerance testing via intraperitoneal injection of C57-diet induced obesity mouse model for fatty liver and diabetes. A) Averages glucose tolerance for 12-day sham injection cohort and 10 mg/kg B-127443 treatment group (n=6) showing marked improvement in glucose tolerance. B) Comparison of three animals before (upper) and after (lower) 12-day treatment with 5 mg/kg B-127443. Animals 1,3 are massively insulin resistant with normoglycemic/resistant to high-fat diet. After treatment, Animals 1,3 have improved glucose tolerance.

DETAILED DESCRIPTION OF EMBODIMENTS

Figure 2:
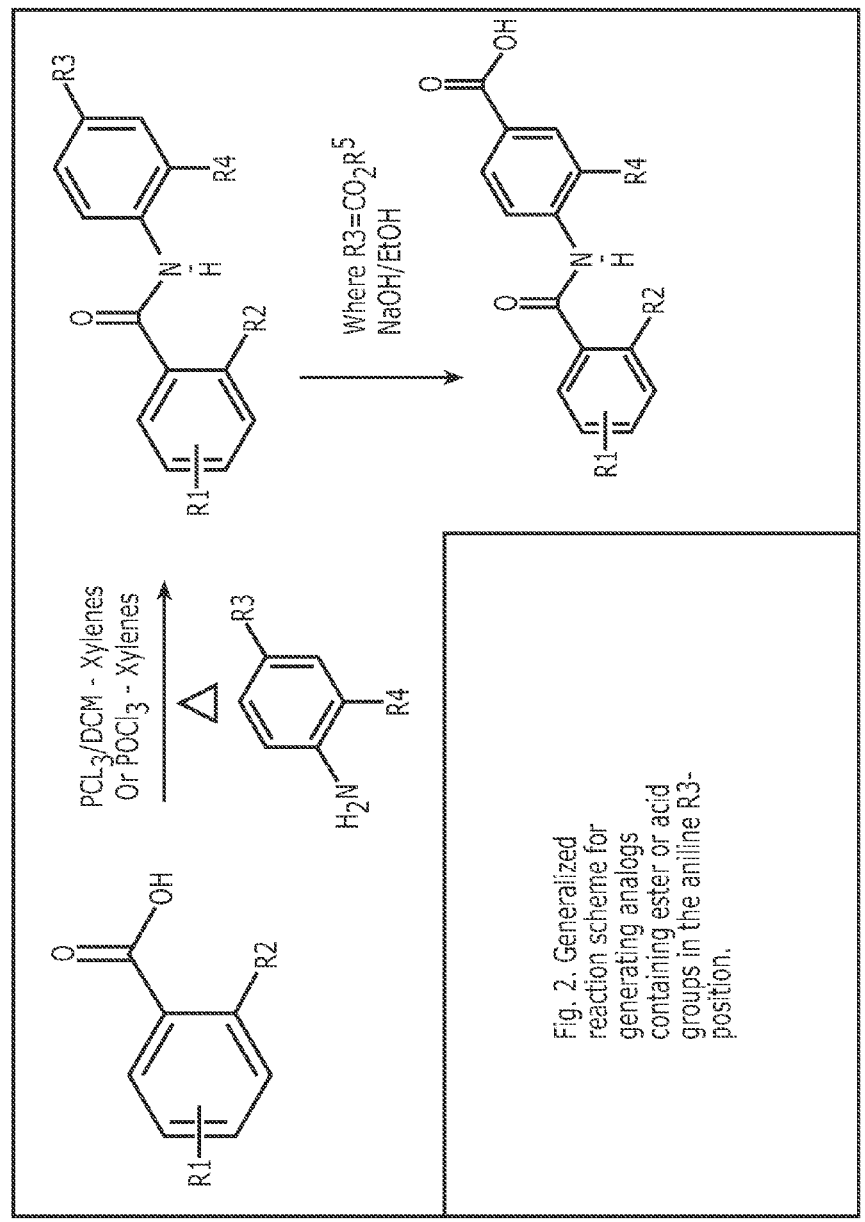
FIG. 2 presents the general reaction scheme for generating analogs containing ester or acid groups in the aniline R3-position.

The present invention is further described below in greater detail. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

All patent and patent application references referred to in this patent application are hereby incorporated by reference in their entirety as if set forth fully herein.

As discussed above, new treatments for NAFLD would fulfill a large unmet medical need that will only grow larger with the T2D/metabolic syndrome (MetS)/obesity epidemic. To achieve this goal, we have established a phenotypic drug discovery platform for fatty liver disease, incorporating high-content screening and quantitative histomorphometry for in vitro and in vivo models. We have identified novel small molecules that modulate lipid metabolism and stimulate lipid clearance in lipid-loaded human cells in an in vitro disease model of fatty liver disease (Sexton et al., International J. High Throughput Screening, 2010, 1, 127-140).

From these initial small molecule leads, a scaffold has been selected based on in vivo efficacy (see Preliminary Data), and medicinal chemistry potential. Our preliminary efforts at developing a structure activity relationship (SAR) have achieved improvements in efficacy and reduced toxicity with 39 novel compounds synthesized and tested in vitro. At least some of these novel compounds have been identified as glutamate dehydrogenase activators. There has recently been some discussion that glutamate dehydrogenase modulation may be therapeutic for type 2 diabetes (Gohring et al., J. Endocrinol., 2012, 212, 239-242).

The most commonly used animal model of metabolic syndrome and related disorders is the C57BL/6J 60% fat diet, diet-induced obesity (DIO) mouse model. This C57-DIO model mimics many aspects of Western diet associated disorders including hyperphagia/obesity, fatty liver, insulin resistance, and increased plasma fatty acids/triglycerides. Using this model, we have demonstrated that our phenotypic high content-high throughput screening assay can identify small molecules with efficacy in reducing triglyceride content in the liver. In proof-of-principle studies, we have tested two prototype compounds in C57BL/6J mice on a 60% high-fat diet and have demonstrated substantial therapeutic value.

Thus, in certain embodiments, the present invention provides compounds of Formula (I):

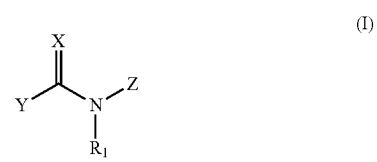

wherein:
X is O or S;
$R_1$ is selected from the group consisting of hydrogen, alkyl, araalkyl, cycloalkyl, and aryl, wherein said alkyl, araalkyl, cycloalkyl and aryl groups can be optionally substituted with one to five substituents selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol;

Y and Z are each independently aryl or heterocycle;
wherein aryl is selected from the group consisting of azulenyl, indanyl, indenyl, naphthyl, phenyl, and tetrahydronaphthyl;
heterocycle is selected from the group consisting of benzimidazolyl, benzopyranyl, benzofuranyl, benzothiazolyl, benzoxazolyl, chromanyl, 1,3-dioxolanyl, furanyl, imidazolinyl, imidazolyl, indazolyl, indolinyl, indolyl, isoindolinyl, isoindolyl, isoquinolinyl, isothiazolyl, isoxazolyl, naphthyridinyl, oxadiazolyl, oxazolyl, purinyl, pyridyl, pyrimidinyl, pyrazinyl, pyrazolyl, pyridazinyl, pyrrolyl, quinazolinyl, quinolinyl, quinoxalinyl, tetrahydroisoquinolinyl, tetrahydroquinolinyl, tetrazolyl, thiazolinyl, thiazolyl, thiazine, and thienyl; wherein:
aryl and heterocycle is unsubstituted or substituted with one to seven substituents each independently selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol; and wherein the substituent can be optionally substituted with one to five substituents selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol; and
a pharmaceutically acceptable salt or prodrug thereof and individual enantiomers and diastereomers thereof.

In some embodiments of Formula (I),
X is O or S;
$R_1$ is selected from:
(1) hydrogen,
(2) $C_{1-6}$ alkyl, which is unsubstituted or substituted with 1-5 substituents each independently selected from:
  (a) halo,
  (b) $C_{3-6}$ cycloalkyl,
  (c) $CF_3$,
  (d) $OR^a$
(3) $C_{3-6}$ cycloalkyl,
(4) araalkyl, and
(5) phenyl;
wherein Y and Z are each independently aryl or heterocycle;
wherein heterocycle is selected from the group consisting of: benzimidazolyl, benzopyranyl, benzofuranyl, benzothiazolyl, benzoxazolyl, chromanyl, 1,3-dioxolanyl, furanyl, imidazolinyl, imidazolyl, indazolyl, indolinyl, indolyl, isoindolinyl, isoindolyl, isoquinolinyl, isothiazolyl, isoxazolyl, naphthyridinyl, oxadiazolyl, oxazolyl, purinyl, pyridyl, pyrimidinyl, pyrazinyl, pyrazolyl, pyridazinyl, pyrrolyl, quinazolinyl, quinolinyl, quinoxalinyl, tetrahydroisoquinolinyl, tetrahydroquinolinyl, tetrazolyl, thiazolinyl, thiazolyl, triazine, and thienyl, which aryl or heterocycle is unsubstituted or substituted with 1-7 substituents each independently selected from:
  (a) halo,
  (b) $C_{1-6}$ alkyl,
  (c) $OR^a$,
  (d) $NO_2$,
  (e) CN,
  (f) $NR^bR^c$,
  (g) $OCO_2R^e$,
  (h) $CO_2R^a$,
  (i) $C(=O)R^a$,
  (j) $C(=O)NR^bR^c$,
  (k) $S(O)_dR^a$,
  (m) $N(R^b)SO_2R^e$,
  (n) $N(R^b)CO_2R^a$,
  (o) $N(R^b)C(=O) R^a$,
  (p) $OCOR^e$,
$R^a$ is independently selected from:
(1) hydrogen, or
(2) $C_{1-6}$ alkyl, which is unsubstituted or substituted with 1-7 substituents each independently selected from:
  (a) halo,
  (b) O—$C_{1-6}$ alkyl, which is unsubstituted or substituted with 1-6 halo,
  (c) hydroxyl,
  (d) CN, and
  (e) aryl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
    (i) halo,
    (ii) O—$C_{1-6}$ alkyl, which is unsubstituted or substituted with 1-6 halo,
    (iii) CN,
    (iv) nitro,
    (v) hydroxyl, and
    (vi) $C_{1-6}$ alkyl, which is unsubstituted or substituted with 1-6 halo;
$R^b$ and $R^c$ are independently selected from:
(1) hydrogen, or
(2) $C_{1-6}$ alkyl, which is unsubstituted or substituted with 1-7 substituents each independently selected from:
  (a) halo,
  (b) $OR^a$,
  (c) CN,
  (d) $CO_2R^a$,
  (e) aryl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
    (i) halo,
    (ii)
    (iii) $C_{1-6}$ alkyl, which is unsubstituted or substituted with 1-6 halo, and
    (iv) nitro;
$R^e$ is independently selected from:
(1) $C_{1-6}$alkyl, which is unsubstituted or substituted with 1-4 substituents each independently selected from:
  (a) halo,
  (b) $OR^a$,
  (c) $CO_2R^a$,
  (d) CN, and
  (e) aryl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) OR$^a$,
(iii) C$_{1-6}$ alkyl, which is unsubstituted or substituted with 1-6 halo, and
(iv) nitro;
d is 0, 1, or 2; or
an individual enantiomer, diastereomer, pharmaceutically acceptable salt or prodrug thereof, In some embodiments of Formula (I),
X is O;
R$_1$ is selected from:
(1) hydrogen,
(2) C$_{1-6}$ alkyl, which is unsubstituted or substituted with 1-5 substituents each independently selected from:
(a) halo,
(b) C$_{3-6}$ cycloalkyl,
(c) CF$_3$,
(d) OR$^a$
(3) C$_{3-6}$ cycloalkyl,
(4) araalkyl, and
(5) phenyl;
wherein Y and Z are each independently aryl or heterocycle;
wherein heterocycle is selected from the group consisting of: benzimidazolyl, benzopyranyl, benzofuranyl, benzothiazolyl, benzoxazolyl, chromanyl, 1,3-dioxolanyl, furanyl, imidazolinyl, imidazolyl, indazolyl, indolinyl, indolyl, isoindolinyl, isoindolyl, isoquinolinyl, isothiazolyl, isoxazolyl, naphthyridinyl, oxadiazolyl, oxazolyl, purinyl, pyridyl, pyrimidinyl, pyrazinyl, pyrazolyl, pyridazinyl, pyrrolyl, quinazolinyl, quinolinyl, quinoxalinyl, tetrahydroisoquinolinyl, tetrahydroquinolinyl, tetrazolyl, thiazolinyl, thiazolyl, triazine and thienyl, which aryl or heterocycle is unsubstituted or substituted with 1-7 substituents each independently selected from:
(a) halo,
(b) C$_{1-6}$alkyl,
(c) OR$^a$,
(d) NO$_2$,
(e) CN,
(f) NR$^b$R$^c$,
(g) OCO$_2$R$^e$,
(h) CO$_2$R$^a$,
(i) C(=O)R$^a$,
(j) C(=O)NR$^b$R$^c$,
(k) S(O)$_d$R$^e$,
(m) N(R$^b$)SO$_2$R$^e$,
(n) N(R$^b$)CO$_2$R$^a$,
(o) N(R$^b$)C(=O)R$^a$,
(p) OCOR$^e$,
R$^a$ is independently selected from:
(1) hydrogen, or
(2) C$_{1-6}$ alkyl, which is unsubstituted or substituted with 1-7 substituents each independently selected from
(a) halo,
(b) O—C$_{1-6}$ alkyl, which is unsubstituted or substituted with 1-6 halo,
(c) hydroxyl,
(d) CN, and
(e) aryl or heterocycle wherein heterocycle is selected from pyridyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) O—C$_{1-6}$ alkyl, which is unsubstituted or substituted with 1-6 halo,
(iii) CN,
(iv) nitro,
(v) hydroxyl, and
(vi) C$_{1-6}$alkyl, which is unsubstituted or substituted with 1-6 halo;
R$^b$ and R$^c$ are independently selected from:
(1) hydrogen, or
(2) C$_{1-6}$ alkyl, which is unsubstituted or substituted with 1-7 substituents each independently selected from:
(a) halo,
(b) OR$^a$,
(c) CN,
(d) CO$_2$R$^a$,
(e) aryl or heterocycle, wherein heterocycle is selected from pyridyl, pyrimidinyl, thienyl, pyridazinyl, piperidinyl, azetidinyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) OR$^a$,
(iii) C$_{1-6}$alkyl, which is unsubstituted or substituted with 1-6 halo, and
(iv) nitro;
R$^e$ is independently selected from:
(1) C$_{1-6}$ alkyl, which is unsubstituted or substituted with 1-4 substituents each independently selected from:
(a) halo,
(b) OR$^a$,
(c) CO$_2$R$^a$,
(d) CN, and
(e) aryl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) OR$^a$,
(iii) C$_{1-6}$ alkyl, which is unsubstituted or substituted with 1-6 halo, and
(iv) nitro;
d is 0, 1, or 2; or
an individual enantiomer, diastereomer, pharmaceutically acceptable salt or prodrug thereof.

In some embodiments of Formula (I),
X is O;
R$_1$ is selected from hydrogen;
wherein Y and Z are each independently aryl or heterocycle;
wherein heterocycle is selected from the group consisting of: benzimidazolyl, benzopyranyl, benzofuranyl, benzothiazolyl, benzoxazolyl, chromanyl, 1,3-dioxolanyl, furanyl, imidazolinyl, imidazolyl, indazolyl, indolinyl, indolyl, isoindolinyl, isoindolyl, isoquinolinyl, isothiazolyl, isoxazolyl, naphthyridinyl, oxadiazolyl, oxazolyl, purinyl, pyridyl, pyrimidinyl, pyrazinyl, pyrazolyl, pyridazinyl, pyrrolyl, quinazolinyl, quinolinyl, quinoxalinyl, tetrahydroisoquinolinyl, tetrahydroquinolinyl, tetrazolyl, thiazolinyl, thiazolyl, triazine and thienyl, which aryl or heterocycle is unsubstituted or substituted with 1-7 substituents each independently selected from:
(a) halo,
(b) $C_{1-6}$ alkyl,
(c) $OR^a$,
(d) $NO_2$,
(e) CN,
(f) $NR^bR^c$,
(g) $OCO_2R^e$,
(h) $CO_2R^a$,
(i) $C(=O)R^a$,
(j) $C(=O)NR^bR^c$,
(k) $S(O)_qR^e$,
(m) $N(R^b)SO_2R^e$,
(n) $N(R^b)CO_2R^a$,
(o) $N(R^b)C(=O)R^a$,
(p) $OCOR^c$,
$R^a$ is independently selected from:
(1) hydrogen, or
(2) $C_{1-6}$ alkyl, which is unsubstituted or substituted with 1-7 substituents each independently selected from:
(a) halo,
(b) O—$C_{1-6}$ alkyl, which is unsubstituted or substituted with 1-6 halo,
(c) hydroxyl,
(d) CN, and
(e) aryl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) O—$C_{1-6}$ alkyl, which is unsubstituted or substituted with 1-6 halo,
(iii) CN,
(iv) nitro,
(v) hydroxyl, and
(vi) $C_{1-6}$ alkyl, which is unsubstituted or substituted with 1-6 halo;
$R^b$ and $R^c$ are independently selected from:
(1) hydrogen, or
(2) $C_{1-6}$ alkyl, which is unsubstituted or substituted with 1-7 substituents each independently selected from:
(a) halo,
(b) $OR^a$,
(c) CN,
(d) $CO_2R^a$,
(e) aryl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) $OR^a$,
(iii) $C_{1-6}$ alkyl, which is unsubstituted or substituted with 1-6 halo, and
(iv) nitro;
$R^e$ is independently selected from:
(1) $C_{1-6}$ alkyl, which is unsubstituted or substituted with 1-4 substituents each independently selected from:
(a) halo,
(b) $OR^a$,
(c) $CO_2R^a$,
(d) CN, and
(e) aryl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) $OR^a$,
(iii) $C_{1-6}$ alkyl, which is unsubstituted or substituted with 1-6 halo, and
(iv) nitro;
d is 0, 1, or 2; or
an individual enantiomer, diastereomer, pharmaceutically acceptable salt or prodrug thereof.

In some embodiments of Formula (I),
X is O or S;
$R_1$ is selected from:
(1) hydrogen,
(2) $C_{1-6}$ alkyl, which is unsubstituted or substituted with 1-5 substituents each independently selected from:
(a) halo,
(b) $C_{3-6}$ cycloalkyl,
(c) $CF_3$,
(d) $OR^a$
(3) $C_{3-6}$ cycloalkyl,
(4) araalkyl, and
(5) phenyl;
wherein:
Y and Z are each independently selected from one of the following:

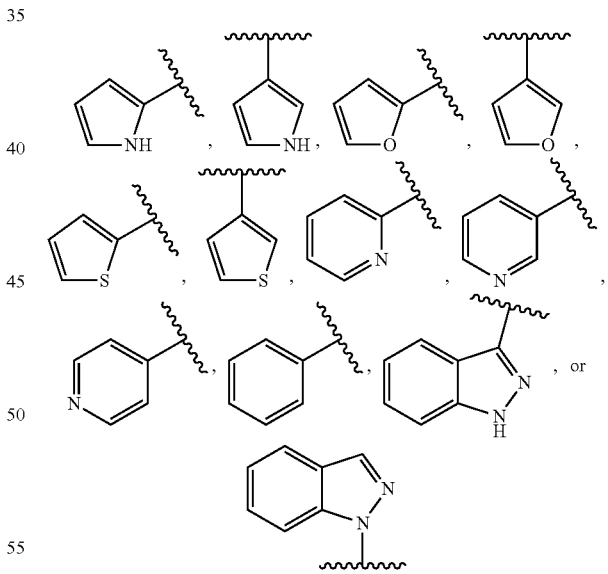

wherein Y and Z are each independently unsubstituted or substituted with 1-5 substituents each independently selected from:
(a) halo,
(b) $C_{1-6}$ alkyl, which is unsubstituted or substituted with 1-5 halo,
(c) $OR^a$,
(d) $NO_2$,
(e) CN,
(f) $NR^bR^c$, (g) $OCO_2R^e$,
(h) $CO_2R^a$,
(i) $C(=O)R^a$,
(j) $C(=O)NR^bR^c$,
(k) $S(O)_dR^e$,
(m) $N(R^b)SO_2R^e$,
(n) $N(R^b)CO_2R^a$,
(o) $N(R^b)C(=O)R^a$, and
(p) $OCOR^e$, wherein:
$R^a$ is independently selected from:
(1) hydrogen, or
(2) $C_{1-6}$ alkyl, which is unsubstituted or substituted with 1-7 substituents each independently selected from:
 (a) halo,
 (b) O—$C_{1-6}$ alkyl, which is unsubstituted or substituted with 1-6 halo,
 (c) hydroxyl,
 (d) CN, and
 (e) aryl or heterocycle wherein heterocycle is selected from pyridyl, pyrimidinyl, thienyl, pyridazinyl, piperidinyl, azetidinyl, (uranyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
  (i) halo,
  (ii) O—$C_{1-6}$ alkyl, which is unsubstituted or substituted with 1-6 halo,
  (iii) CN,
  (iv) nitro,
  (v) hydroxyl, and
  (vi) $C_{1-6}$alkyl, which is unsubstituted or substituted with 1-6 halo;
$R^1$) and $R^e$ are independently selected from:
(1) hydrogen, or
(2) $C_{1-6}$ alkyl, which is unsubstituted or substituted with 1-7 substituents each independently selected from:
 (a) halo,
 (b) $OR^a$,
 (c) CN,
 (d) $CO_2R^a$,
 (e) aryl or heterocycle, wherein heterocycle is selected from pyridyl, pyrimidinyl, thienyl, pyridazinyl, piperidinyl, azetidinyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
  (i) halo,
  (ii) $OR^a$,
  (iii) $C_{1-6}$alkyl, which is unsubstituted or substituted with 1-6 halo, and
  (iv) nitro;
$R^e$ is independently selected from:
(1) $C_{1-6}$ alkyl, which is unsubstituted or substituted with 1-4 substituents each independently selected from:
 (a) halo,
 (b) $OR^a$,
 (c) $CO_2R^a$,
 (d) CN, and
 (e) aryl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
  (i) halo,
  (ii) $OR^a$,
  (iii) $C_{1-6}$ alkyl, which is unsubstituted or substituted with 1-6 halo, and
  (iv) nitro;
d is 0, 1, or 2; or
an individual enantiomer, diastereomer, pharmaceutically acceptable salt or prodrug thereof.

Also provided are compounds of Formula (II):

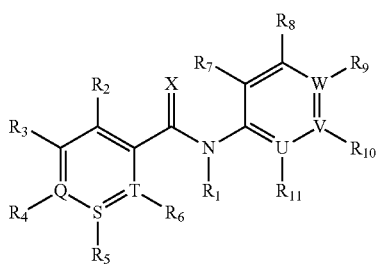

(II)

wherein:
X is O or S;
Q, S, T, U, V, and W are CH or N;
$R_1$ is selected from:
(1) hydrogen,
(2) $C_{1-6}$ alkyl, which is unsubstituted or substituted with 1-5 substituents each independently selected from:
 (a) halo,
 (b) $C_{3-6}$ cycloalkyl,
 (c) $CF_3$,
 (d) $OR^a$
(3) $C_{3-6}$ cycloalkyl,
(4) araalkyl, and
(5) phenyl;
$R_2$, $R_4$, $R_5$, $R_7$, $R_8$, and $R_{10}$ are H;
$R_3$ is selected from the group consisting of hydrogen, $C_{1-6}$ alkyl, which is unsubstituted or substituted with 1-5 halo, halo, and $OR^a$;
$R_6$ is selected from the group consisting of hydrogen, $OR^a$, $NO_2$, and $OC(O)R^e$;
$R_9$ is selected from the group consisting of hydrogen, $C_{1-6}$ alkyl, which is unsubstituted or substituted with 1-5 halo; $CO_2R^a$, $C(=O)NR^bR^c$, $NO_2$, $OR^a$, halo, and CN;
$R_{11}$ is selected from the group consisting of hydrogen, halo, $OR^a$, and $C_{1-6}$ alkyl, which is unsubstituted or substituted with 1-5 halo;
wherein:
$R^a$ is independently selected from:
(1) hydrogen, or
(2) $C_{1-6}$ alkyl, which is unsubstituted or substituted with 1-7 substituents each independently selected from:
 (a) halo,
 (b) O—$C_{1-6}$ alkyl, which is unsubstituted or substituted with 1-6 halo,
 (c) hydroxyl,
 (d) CN, and
 (e) aryl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
    (i) halo,
    (ii) O—$C_{1-6}$ alkyl, which is unsubstituted or substituted with 1-6 halo,
    (iii) CN,
    (iv) nitro,
    (v) hydroxyl, and
    (vi) $C_{1-6}$ alkyl, which is unsubstituted or substituted with 1-6 halo;
$R^b$ and $R^c$ are independently selected from:
    (1) hydrogen, or
    (2) $C_{1-6}$ alkyl, which is unsubstituted or substituted with 1-7 substituents each independently selected from:
        (a) halo,
        (b) $OR^a$,
        (e) CN,
        (d) $CO_2R^a$,
        (e) aryl or heterocycle, wherein heterocycle is selected from pyridyl, pyrimidinyl, thienyl, pyridazinyl, piperidinyl, azetidinyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
            (i) halo,
            (ii)
            (iii) $C_{1-6}$ alkyl, which is unsubstituted or substituted with 1-6 halo, and
            (iv) nitro;
$R^e$ is independently selected from:
    (1) $C_{1-6}$ alkyl, which is unsubstituted or substituted with 1-4 substituents each independently selected from:
        (a) halo,
        (b) $OR^a$,
        (c) $CO_2R^a$,
        (d) CN, and
        (e) aryl or heterocycle, wherein heterocycle is selected from pyridyl, pyrimidinyl, thienyl, pyridazinyl, piperidinyl, azetidinyl, (uranyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
            (i) halo,
            (ii) $OR^a$,
            (iii) $C_{1-6}$alkyl, which is unsubstituted or substituted with 1-6 halo, and
            (iv) nitro; or an individual enantiomer, diastereomer, pharmaceutically acceptable salt or prodrug thereof.

In some embodiments of Formula (II),
X is O;
Q, S, T, U, V, and W are CH or N;
$R_1$ is selected from:
    (1) hydrogen,
    (2) $C_{1-6}$ alkyl, which is unsubstituted or substituted with 1-5 substituents each independently selected from:
        (a) halo,
        (b) $C_{3-6}$ cycloalkyl,
        (c) $CF_3$,
        (d) OR (3) $C_{3-6}$ cycloalkyl,
    (4) araalkyl, and
    (5) phenyl;
$R_2$, $R_4$, $R_5$, $R_7$, $R_8$, and $R_{10}$ are H;
$R_3$ is selected from the group consisting of hydrogen, $C_{1-6}$ alkyl, which is unsubstituted or substituted with 1-5 halo, halo, and $OR^a$;
$R_6$ is selected from the group consisting of hydrogen, $OR^a$, $NO_2$, and $OC(O)R^e$;
$R_9$ is selected from the group consisting of hydrogen, $C_{1-6}$ alkyl, which is unsubstituted or substituted with 1-5 halo; $CO_2R^a$, $C(=O)NR^bR^c$, $NO_2$, $OR^a$, halo, and CN;
$R_{11}$ is selected from the group consisting of hydrogen, halo, $OR^a$, and $C_{1-6}$alkyl, which is unsubstituted or substituted with 1-5 halo;
wherein:
$R^a$ is independently selected from:
    (1) hydrogen, or
    (2) $C_{1-6}$ alkyl, which is unsubstituted or substituted with 1-7 substituents each independently selected from:
        (a) halo,
        (b) O—$C_{1-6}$alkyl, which is unsubstituted or substituted with 1-6 halo,
        (c) hydroxyl,
        (d) CN, and
        (e) aryl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
            (i) halo,
            (ii) O—$C_{1-6}$ alkyl, which is unsubstituted or substituted with 1-6 halo,
            (iii) CN,
            (iv) nitro,
            (v) hydroxyl, and
            (vi) $C_{1-6}$ alkyl, which is unsubstituted or substituted with 1-6 halo;
$R^b$ and $R^c$ are independently selected from:
    (1) hydrogen, or
    (2) $C_{1-6}$ alkyl, which is unsubstituted or substituted with 1-7 substituents each independently selected from:
        (a) halo,
        (b) $OR^a$,
        (c) CN,
        (d) $CO_2R^a$,
        (e) aryl or heterocycle, wherein heterocycle is selected from pyridyl, pyrimidinyl, thienyl, pyridazinyl, piperidinyl, azetidinyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
            (i) halo,
            (ii) $OR^a$,
            (iii) $C_{1-6}$ alkyl, which is unsubstituted or substituted with 1-6 halo, and
            (iv) nitro;
$R^e$ is independently selected from:
    (1) $C_{1-6}$alkyl, which is unsubstituted or substituted with 1-4 substituents each independently selected from:
        (a) halo,
        (b) $OR^a$,
        (c) $CO_2R^a$,
        (d) CN, and (e) aryl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) $OR^a$,
(iii) $C_{1-6}$ alkyl, which is unsubstituted or substituted with 1-6 halo, and
(iv) nitro; or
an individual enantiomer, diastereomer, pharmaceutically acceptable salt or prodrug thereof.

In some embodiments of Formula (II),
X is O;
Q, S, T, U, V, and W are CH or N;
$R_1$, $R_2$, $R_4$, $R_5$, $R_7$, $R_8$, and $R_{10}$ are H;
$R_3$ is selected from the group consisting of hydrogen, $C_{1-6}$ alkyl, which is unsubstituted or substituted with 1-5 halo, halo, and $OR^a$;
$R_6$ is selected from the group consisting of hydrogen, $OR^a$, $NO_2$, and $OC(O)R^e$;
$R_9$ is selected from the group consisting of hydrogen, $C_{1-6}$alkyl, which is unsubstituted or substituted with 1-5 halo; $CO_2R^a$, $C(=O)NR^bR^c$, $NO_2$, $OR^a$, halo, and CN;
$R_{11}$ is selected from the group consisting of hydrogen, halo, $OR^a$, and $C_{1-6}$ alkyl, which is unsubstituted or substituted with 1-5 halo;
wherein:
$R^a$ is independently selected from:
(1) hydrogen, or
(2) $C_{1-6}$ alkyl, which is unsubstituted or substituted with 1-7 substituents each independently selected from:
(a) halo,
(b) O—$C_{1-6}$ alkyl, which is unsubstituted or substituted with 1-6 halo,
(c) hydroxyl,
(d) CN, and
(e) aryl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) O—$C_{1-6}$ alkyl, which is unsubstituted or substituted with 1-6 halo,
(iii) CN,
(iv) nitro,
(v) hydroxyl, and
(vi) $C_{1-6}$ alkyl, which is unsubstituted or substituted with 1-6 halo;
$R^b$ and $R^c$ are independently selected from:
(1) hydrogen, or
(2) $C_{1-6}$ alkyl, which is unsubstituted or substituted with 1-7 substituents each independently selected from:
(a) halo,
(b) $OR^a$,
(c) CN,
(d) $CO_2R^a$,
(e) aryl or heterocycle, wherein heterocycle is selected from pyridyl, pyrimidinyl, thienyl, pyridazinyl, piperidinyl, azetidinyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) $OR^a$,
(iii) $C_{1-6}$alkyl, which is unsubstituted or substituted with 1-6 halo, and
(iv) nitro;
$R^e$ is independently selected from:
(1) $C_{1-6}$alkyl, which is unsubstituted or substituted with 1-4 substituents each independently selected from:
(a) halo,
(b) $OR^a$,
(c) $CO_2R^a$,
(d) CN, and
(e) aryl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuryl, tetrahydropyranyl, triazine and pyrazinyl, which aryl or heterocycle is unsubstituted or substituted with 1-7 substituents each independently selected from:
(i) halo,
(ii) $OR^a$,
(iii) $C_{1-6}$ alkyl, which is unsubstituted or substituted with 1-6 halo, and
(iv) nitro; or
an individual enantiomer, diastereomer, pharmaceutically acceptable salt or prodrug thereof.

Also provided are compounds of Formula (III):

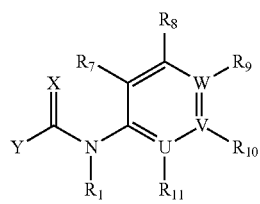

(III)

wherein:
X is O or S;
Y is pyrrole;
wherein:
said pyrrole is unsubstituted or substituted with one to four substituents each independently selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol; and wherein the substituent can be optionally substituted with one to five substituents selected from the group consisting of H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol;
U, V, and W are CH or N;
$R_7$, $R_8$, and $R_{10}$ are H;
$R_9$ is selected from the group consisting of hydrogen, $C_{1-6}$ alkyl, which is unsubstituted or substituted with 1-5 halo; $CO_2R^a$, $C(=O)NR^bR^c$, $NO_2$, $OR^a$, halo, and CN;
$R_{11}$ is selected from the group consisting of hydrogen, halo, $OR^a$, and $C_{1-6}$ alkyl, which is unsubstituted or substituted with 1-5 halo;

$R_1$, $R^a$, $R^b$ and $R^c$ are as defined above; or an individual enantiomer, diastereomer, pharmaceutically acceptable salt or prodrug thereof, Also provided are compounds of Formula (IV):

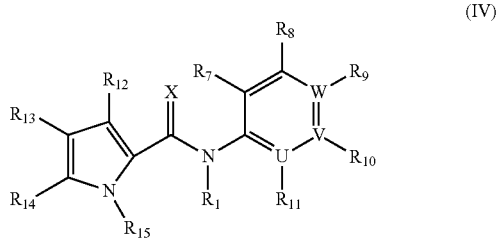

(IV)

wherein:
X is O or S;
U, V, and W are CH or N;
$R_7$, $R_8$, and $R_{10}$ are H;
$R_9$ is selected from the group consisting of hydrogen, $C_{1-6}$ alkyl, which is unsubstituted or substituted with 1-5 halo; $CO_2R^a$, $C(=O)NR^bR^c$, $NO_2$, $OR^a$, halo, and CN;
$R_{11}$ is selected from the group consisting of hydrogen, halo, $OR^a$, and $C_{1-6}$ alkyl, which is unsubstituted or substituted with 1-5 halo;
$R_{12}$, $R_{13}$, $R_{14}$ is selected from the group consisting of hydrogen, halo, $C_{1-6}$ alkyl, $NO_2$, CN, $NR^bR^c$, $OCO_2R^e$, $CO_2R^a$, $C(=O)R^a$, $C(=O)NR^bR^c$, $S(O)_dR^e$, $N(R^b)SO_2R^e$, $N(R^b)CO_2R^a$, $N(R^b)C(=O)R^a$, and $OCOR^e$;
$R_{15}$ is selected from:
(1) hydrogen,
(2) $C_{1-6}$ alkyl, which is unsubstituted or substituted with 1-5 substituents each independently selected from:
  (a) halo,
  (b) $C_{3-6}$ cycloalkyl,
  (c) $CF_3$,
  (d) $OR^a$
(3) $C_{3-6}$ cycloalkyl,
(4) araalkyl, and
(5) phenyl;
wherein:
$R_1$, $R^a$, $R^b$, $R^c$, d and $R^e$ are as defined above.
In some embodiments of Formula IV, X is O.

A. DEFINITIONS

Compounds as active agents of this invention include those described generally above, and are further illustrated by the embodiments, sub-embodiments, and species disclosed herein. As used herein, the following definitions shall apply unless otherwise indicated.

As described herein, compounds of the invention may optionally be substituted with one or more substituents, such as those illustrated generally above, or as exemplified by particular classes, subclasses, and species of the invention. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

As used herein, "a," "an" or "the" can mean one or more than one. Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a compound) and the like, is meant to encompass variations of ±20%, ±10%, ±5%, ±1%, ±0.5%, or even ±0.1% of the specified amount.

"Isomers" refer to compounds having the same number and kind of atoms and hence the same molecular weight, but differing with respect to the arrangement or configuration of the atoms.

"Stereoisomers" refer to isomers that differ only in the arrangement of the atoms in space.

"Diastereoisomers" refer to stereoisomers that are not mirror images of each other.

"Enantiomers" refers to stereoisomers that are non-superimposable mirror images of one another.

Enantiomers include "enantiomerically pure" isomers that comprise substantially a single enantiomer, for example, greater than or equal to about 90%, 92%, 95%, 98%, or 99%, or equal to about 100% of a single enantiomer.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the opposite enantiomer, of the compound. A typical stereomerically pure compound comprises greater than about 80% by weight of one stereoisomer of the compound and less than about 20% by weight of the other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Enantiomeric excess" (ee) of an enantiomer is [(the mole fraction of the major enantiomer) minus (the mole fraction of the minor enantiomer)]×100.

"Stable", as used herein, refers to compounds that are not substantially altered when subjected to conditions to allow for the production, detection, and preferably the recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

"H" refers to a hydrogen atom. "C" refers to a carbon atom. "N" refers to a nitrogen atom. "O" refers to an oxygen atom. "S" refers to a sulfur atom.

"F" refers to a fluorine atom. "Cl" refers to a chlorine atom. "Br" refers to a bromine atom. "I" refers to an iodine atom.

"Alkyl", as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). In some embodiments the alkyl can be a lower alkyl. "Lower alkyl" refers to straight or branched chain alkyl having from 1 to 3, or from 1 to 5, or from 1 to 8 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. In some embodiments, alkyl groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocycle, heteroaryl, hydroxy, nitro, oxo, oxy, peptide, sulfone, sulfoxide, and thiol.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

"Alkenyl", as used herein, refers to a straight or branched chain hydrocarbon containing from 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. In some embodiments, alkenyl groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Alkynyl", as used herein, refers to a straight or branched chain hydrocarbon group containing from 2 to 10 or 20 or more carbon atoms, and containing at least one carbon-carbon triple bond. Representative examples of alkynyl include, but are not limited, to acetylenyl, 1-propynyl, 2-propynyl, 1-butynyl, 2-butynyl, 2-pentynyl, and the like.

In some embodiments, alkynyl groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

The term "cycloalkyl", as used herein, refers to a saturated or unsaturated cyclic hydrocarbon group containing from 3 to 8 carbons or more. Representative examples of cycloalkyl include cyclopropyl, cyclobutyl, cyclobutenyl, cyclopentyl, cyclohexyl, cycloheptyl, and cyclooctyl. In some embodiments, cycloalkyl groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Heterocyclo", "heterocyclic" and "heterocycle" as used herein, refers to a monocyclic, bicyclic or tricyclic ring system. Monocyclic heterocycle ring systems are exemplified by any 3, 4, 5 or 6 membered ring containing 1, 2, 3, or 4 heteroatoms independently selected from the group consisting of O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiomorpholine sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. In some embodiments, heterocyclo groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Aryl" as used herein refers to a ring system having one or more aromatic rings. Representative examples of aryl include azulenyl, indanyl, indenyl, naphthyl, phenyl, tetrahydronaphthyl, and the like. The aryl groups of this invention can be optionally substituted with 1, 2, 3, 4, 5, 6 or 7 substituents independently selected from, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolinyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O. In some embodiments, heteroaryl groups as described herein are optionally substituted (e.g., from 1 to 3 or 4 times) with independently selected H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

An "acid" is a compound that can act as a proton donor or electron pair acceptor, and thus can react with a base. The strength of an acid corresponds to its ability or tendency to lose a proton. A "strong acid" is one that completely dissociates in water. Examples of strong acids include, but are not limited to, hydrochloric acid (HCl), hydroiodic acid (HI), hydrobromic acid (HBr), perchloric acid (HClO$_4$), nitric acid (HNO$_3$), sulfuric acid (H$_2$SO$_4$), etc. A "weak" or "mild" acid, by contrast, only partially dissociates, with both the acid and the conjugate base in solution at equilibrium. Examples of mild acids include, but are not limited to, carboxylic acids such as acetic acid, citric acid, formic acid, gluconic acid, lactic acid, oxalic acid, tartaric acid, ethylenediaminetetraacetic acid (EDTA), etc.

An "acid halide" as used herein refers to an organic functional group having a carbonyl group (C=O) linked to a halogen.

An "acyl group" is intended to mean a group —C(O)R, where R is a suitable substituent (for example, an acyl group may be an acetyl group (—C(O)CH$_3$), a propionyl group, a butyroyl group, a benzoyl group, or an alkylbenzoyl group).

"Aliphatic" is an acyclic or cyclic, non-aromatic carbon compound.

"Alkoxy", as used herein, refers to an alkyl, alkenyl, alkynyl, aryl, cycloalkyl, heterocyclo, or heteroaryl group, as defined herein, appended to the parent molecular moiety through an oxy group, as defined herein. Representative examples of alkoxy include, but are not limited to, methoxy, ethoxy, propoxy, phenoxy, 2-propoxy, butoxy, tert-butoxy, pentyloxy, hexyloxy and the like. In some embodiments, alkoxy groups as described herein are optionally substituted (e.g., from 1 to 3 or 5 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Amidino" as used herein, refers to the C(=NH)NH$_2$ moiety. "Optionally substituted" amidino refers to the NH and NH$_2$ groups wherein none, one, two or three of the hydrogens is replaced by a suitable substituent as described herein, such as alkyl, alkenyl, alkynyl, cycloalkyl, heterocyclo, aryl, heteroaryl, alkoxy, carbonyl, carboxy, etc.

An "amine" or "amino" is intended to mean the group —NH$_2$. "Optionally substituted" amines refers to —NH$_2$ groups wherein none, one or two of the hydrogens is replaced by a suitable substituent as described herein, such as alkyl, alkenyl, alkynyl, cycloalkyl, heterocyclo, aryl, heteroaryl, alkoxy, carbonyl, carboxy, etc. In some embodiments, one or two of the hydrogens are optionally substituted with independently selected, but not limited to, halo, hydroxy, acyl, alkyl, alkenyl, alkynyl, cycloalkyl, heterocyclo, aryl, heteroaryl, alkoxy, amino, amide, thiol, ester, sulfone, sulfoxide, oxo, oxy, nitro, carbonyl, carboxy, amino acid and peptide. Disubstituted amines may have substituents that are bridging, i.e., form a heterocyclic ring structure that includes the amine nitrogen.

An "amine", "organic amine", "amine base" or "organic amine base" as used herein refers to an organic compound having a basic nitrogen atom (R—NR'R"), and may be a primary (R—NH$_2$), secondary (R—NHR') or tertiary (R—NR'R") amine. R, R' and R" may be independently selected from the group consisting of alkyl (e.g., cycloalkyl), aryl and heteroaryl, which groups may be optionally substituted, or R and R', R and R" and/or R' and R", when present, may also combine to form cyclic or heteroalicyclic ring. In some embodiments the amine is aromatic. Examples of aromatic amines include, but are not limited to, pyridine, pyrimidine, quinoline, isoquinolines, purine, pyrrole, imidazole, and indole. The aromatic amines may be substituted or unsubstituted. Examples of amines include, but are not limited to, triethylamine, pyridine, dimethylaminopyridine, N-methylmorpholine, Hunig's base (N,N-diisopropylethylamine), and 1,8-diazabicyclo[5.4.0]undec-7-ene (DBU).

An "amide" as used herein refers to an organic functional group having a carbonyl group (C=O) linked to a nitrogen atom (N), or a compound that contains this group, generally depicted as:

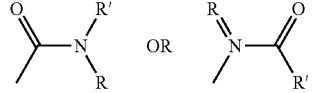

wherein, R and R' can independently be any covalently-linked atom or atoms, for example, H, halo, hydroxy, acyl, alkyl, alkenyl, alkynyl, cycloalkyl, heterocyclo, aryl, heteroaryl, alkoxy, amino, amide, sulfone, sulfoxide, carboxy, amino acid and peptide.

An "amide coupling agent" is an agent that may be used to couple a nitrogen and carboxyl group to form an amide, typically by activating the carboxyl group. Examples of amide coupling agents include, but are not limited to, carbodiimides such as N,N-dicyclohexylcarbodiimide (DCC), N-(3-dimethylaminopropyl)-N'-ethylcarbodiimide (EDC) or N-(3-dimethylaminopropyl)-N-ethylcarbodiimide hydrochloride (EDAC), N,N'-diisopropylcarbodiimide (DIC); imidazoliums such as 1,1'-carbonyldiimidazole (CDI), 1,1'-carbonyl-di-(1,2,4-triazole) (CDT); uronium or guanidinium salts such as O-(7-azabenzotriazol-1-yl)-N,N, N',N'-tetramethyluronium hexafluorophosphate (HATU), O-(benzotriazol-1-yl)-N,N,N',N'-tetramethyluronium hexafluorophosphate (HBTU), and O-(benzotriazol-1-yl)-N,N,N',N'-tetramethyluronium tetrafluoroborate (TBTU); phosphonium salts such as benzotriazol-1-yloxy)tris(dimethylamino)phosphonium hexafluorophosphate (BOP or Castro's reagent), (benzotriazol-1-yloxy)tripyrrol idinophosphonium hexafluorophosphate (PyBOP®, Merck KGaA, Germany), 7-azabenxotriazol-1-yloxy)tripyrrolidinophosphonium hexafluorophosphate (PyAOP); alkyl phosphonic acid anhydrides such as T3P® (Archirnica, Germany), etc. In another embodiment the carboxyl group may be activated by forming an acid halide or acid anhydride with an agent including but not limited to thionyl chloride, phosphorus pentachloride, and phosphorus trichloride.

"Amino acid sidechain" as used herein refers to any of the 20 commonly known groups associated with naturally-occurring amino acids, or any natural or synthetic homologue thereof. An "amino acid" includes the sidechain group, the amino group, alpha-carbon atom, and carboxy groups, as commonly described in the art. Examples of amino acids include glycine, and glycine that is substituted with a suitable substituent as described herein, such as alkyl, alkenyl, alkynyl, cycloalkyl, heterocyclo, aryl, heteroaryl, alkoxy, carbonyl, carboxy, etc., or a pharmaceutically acceptable salt or prodrug thereof. For example, "Histidine" is one of the 20 most commonly known amino acids found naturally in proteins. It contains a —(CH$_2$)-imidazole side chain substituent. Other examples of naturally-occurring amino acids include lysine, arginine, aspartic acid, glutamic acid, asparagine, glutamine, serine, threonine, tyrosine, alanine, valine, leucine, isoleucine, phenylalanine, methionine, tryptophan, and cysteine. Also included in the definitions of "amino acid sidechain" and "amino acid" is proline, which is commonly included in the definition of an amino acid, but is technically an imino acid. As used in this application, both the naturally-occurring L- and the non-natural D-amino acid enantiomers are included. The single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr).

"Aqueous" is a solution in which water is the dissolving medium, or solvent. An "aqueous base" is a base in water, An "aqueous acid" is an acid in water.

"Araalkyl", as used herein, refers to an alkyl group that has an aryl group appended thereto, for example benzyl and naphthylmethyl groups.

"Azido", as used herein, refers to the N$_3$ functional group.

A "base" is a compound that can accept a proton (hydrogen ion) or donate an electron pair. A base may be organic (e.g., DBU, cesium carbonate, etc.) or inorganic. A "strong base" as used herein is a compound that is capable of deprotonating very weak acids. Examples of strong bases include, but are not limited to, hydroxides, alkoxides, and ammonia.

"Carbonate", as used herein refers to a —O(CO$_2$)R functional group wherein R is for example, alkyl, alkenyl, alkynyl, cycloalkyl, heterocyclo, aryl and heteroaryl that may be optimally substituted.

"Carbonyl" is a functional group having a carbon atom double-bonded to an oxygen atom (C=O).

"Carboxy" and "carboxylic acid" as used herein refers to a —COOH functional group, also written as CO$_2$H or —(C=O)—OH.

"Cyano" refers to the group —C≡N, or —CN.

"Ester" as used herein refers to a —COOR functional group, also written as —CO$_2$R or —(C=O)—OR wherein, R is for example, alkyl, alkenyl, alkynyl, cycloalkyl, heterocyclo, aryl and heteroaryl that may be optimally substituted.

"Form a ring" as used herein with respect to two substituents, e.g., R$^7$ and R$^8$ together forming a ring, refers to the two groups being linked together via one or more atoms (e.g., carbon) to form ring atoms making up a cycloalkyl, heterocyclo, aryl or heteroaryl as described herein. Rings may be part of a monocyclic, bicyclic or tricyclic moiety, each of such ring(s) being a saturated or unsaturated member of the monocyclic, bicyclic or tricyclic moiety.

"Formylated", as used herein, refers to a chemical reaction that introduces a formyl group (methanoyl, CHO) into an organic molecule, "Formyl" or "formyl group", as used herein, refers to a CHO moiety.

"Halo" refers to F, Cl, Br or I.

"Hydroxy", as used herein, refers to an HO— moiety.

A "hydroxide" is the commonly known anion HO$^-$, or a salt thereof (typically an alkali metal or alkaline earth metal salt thereof). Examples of hydroxides include, but are not limited to, sodium hydroxide (NaOH), potassium hydroxide (KOH), lithium hydroxide (LiOH), and calcium hydroxide (Ca(OH)$_2$).

An "inorganic" compound is a compound not containing carbon.

The term "oxo", as used herein, refers to a =O moiety.

The term "oxy", as used herein, refers to a —O— moiety.

"Nitro" refers to the organic compound functional group NO$_2$,

A "thiol" or "mercapto" refers to an —SH group, its tautomer =S or —SR wherein, R is for example alkyl, alkenyl, alkynyl, cycloalkyl, heterocyclo, aryl and heteroaryl that may be optimally substituted.

A "sulfone" as used herein refers to a sulfonyl functional group, generally depicted as:

wherein, R can be any covalently-linked atom or atoms, for example, H, halo, hydroxy, alkyl, alkenyl, alkynyl, cycloalkyl, heterocyclo, aryl, heteroaryl, alkoxy, amino, amino acid and peptide.

A "sulfoxide" as used herein refers to a sulfinyl functional group, generally depicted as:

wherein, R can be any covalently-linked atom or atoms, for example, H, halo, hydroxy, alkyl, alkenyl, alkynyl, cycloalkyl, heterocyclo, aryl, heteroaryl, alkoxy, amino, amino acid and peptide.

The term "optionally substituted" indicates that the specified group is either unsubstituted or substituted by one or more suitable substituents. A "substituent" is an atom or group which takes the place of a hydrogen atom on the parent chain or cycle of an organic molecule, examples include, but are not limited to, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol. In some embodiments, the substituent may be further substituted. For example, an atom or group which takes the place of a hydrogen atom on the substituent; examples include, but are not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

An "organic" compound as used herein is a compound that contains carbon.

An "organic solvent" is a compound containing carbon that is useful as a solvent. Examples of organic solvents include, but are not limited to, acid amides such as N,N-dimethylformamide and N,N-dimethylacetamide; alcohols such as ethanol, methanol, isopropanol, amyl alcohol, ethylene glycol, propylene glycol, 1-butanol, butyl carbitol acetate and glycerin; aliphatic hydrocarbons such as hexane and octane; aromatic hydrocarbons such as toluene, xylenes and benzene; ketones such as acetone, methyl ethyl ketone and cyclohexanone; halogenated hydrocarbons such as dichloromethane, chlorobenzene and chloroform; esters such as ethyl acetate, amyl acetate and butyl acetate; ethers such as tetrahydrofuran, 2-methyltetrahydrofuran, 1,4-dioxane, tert-butyl methyl ether, diethyl ether and ethylene glycol dimethyl ether; nitriles such as acetonitrile; and sulfoxides such as dimethylsulfoxide.

An "oxidizing agent" is an agent useful to oxidize a compound, whereby the compound loses electrons or increases its oxidation state. Examples include, but are not limited to, oxygen, ozone, organic peroxides such as hydrogen peroxide, halogens such as fluorine or chlorine, or halogen compounds such as chlorite, chlorate or perchlorate, nitrate compounds such as nitric acid, a sulfuric acid or persulfuric acid, hypohalite compounds such as hypochlorite and sodium hypochlorite (NaOCl), hexavalent chromium compounds such as chromic and dichromic acids and chromium trioxide, pyridinium chlorochromate and chromate/dichromate compounds, permanganate compounds, sodium perborate, nitrous oxide, silver oxide, osmium tetroxide, Tollens' reagent, and 2,2'-dipyridyldisulfide.

A "peptide" is a linear chain of amino acids covalently linked together, typically through an amide linkage, and contains from 1 or 2 to 10 or 20 or more amino acids, and is also optionally substituted and/or branched.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propionates, oxalates, malonates, succinates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entirety, "Protecting group" as used herein, is meant that a particular functional moiety, e.g., O, S, or N, is temporarily blocked so that a reaction can be carried out selectively at another reactive site in a multifunctional compound. For example, in certain embodiments, as detailed herein, certain exemplary oxygen protecting groups are utilized. Oxygen protecting groups include, but are not limited to, groups bonded to the oxygen to form an ether, such as methyl, substituted methyl (e.g., Trt (triphenylmethyl), MOM (methoxymethyl), MTM (methylthiomethyl), BOM (benzyloxymethyl), PMBM or MPM (p-methoxybenzyloxymethyl)), substituted ethyl (e.g., 2-(trimethylsilyl)ethyl), benzyl, substituted benzyl (e.g., para-methoxybenzyl), silyl (e.g., TMS (trimethylsilyl), TES (triethylsilyl), TIPS (triisopropylsilyl), TBDMS (t-butyldimethylsilyl), TBDPS (t-butyldiphenylsilyl), 2-trimethylsilylprop-2-enyl, t-butyl, tetrahydropyranyl, allyl, etc.

B. METHODS OF TREATMENT

A subject of this invention is any subject in whom prevention and/or treatment of a metabolic disorder is needed or desired, as well as any subject prone to a metabolic disorder. In some embodiments, the subject is a human; however, a subject of this invention can include an animal subject, particularly mammalian subjects such as canines, felines, bovines, caprines, equines, ovines, porcines, rodents (e.g. rats and mice), lagomorphs, primates (including non-human primates), etc., for veterinary medicine or pharmaceutical drug development purposes.

The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric.

As used herein, a "metabolic disease" or "metabolic disorder" (wherein disease and disorder can be used interchangeably) refers to a condition caused by an abnormal metabolic process. Common metabolic disorders include, but are not limited to, diabetes, insulin resistance, obesity, dyslipidemia, lypolipedemia, hyperthyroidism, hypothyroidism, galaetosemia and phenylketonuria. "Diabetes" can refer to a disease diagnosed as diabetes according to the diagnostic standard, for example, of WHO (World Health Organization), Japan Diabetes Society, American Diabetes Association or European Association for the Study of Diabetes and includes Type 1 diabetes, Type 2 diabetes, gestational or pregnancy diabetes, and the like. Type 2 diabetes can be characterized by its resistance to the action of insulin, i.e., "insulin resistance." "Insulin resistance" can mean a disease diagnosed as insulin resistance, based on the insulin resistance index (fasting blood sugar (mg/dL)×fasting insulin (microU/mL)÷405) or on the results obtained by examination by glucose clamp method or the like and includes syndrome X additionally. In addition to Type 2 diabetes, diseases with "insulin resistance" include, for example, fatty liver, particularly NAFLD (non-alcoholic fatty liver disease), NASH (non-alcoholic steatohepatitis), coronary heart diseases (CHDs), arteriosclerotic diseases, hyperglycemia, lipodosis, impaired glucose tolerance, hypertension, hyperlipemia, diabetes complications, pregnancy diabetes, polycystic ovary syndrome and the like.

The term "dyslipidemia" means a disease diagnosed as dyslipidemia according to the diagnostic standard, for example, by the WHO or Japan Atherosclerosis Society and includes hyperlipemia, hypercholestrolemia, hyper-LDL-eholestrolemia, hypo-HDL-cholestrolemia, hypertriglyceridemia and the like.

The term "obesity" means a disease diagnosed as obesity according to the diagnostic standard, for example, of WHO or Japan Society for the Study of Obesity and include "overweight" and others.

The term "metabolic syndrome" means a disease diagnosed as metabolic syndrome according to the diagnostic standard, for example, by the WHO, NCEP, IDF or the Committee for Diagnostic Standard of Metabolic Syndrome in the Japan Atherosclerosis Society.

However, in any circumstance, a diagnosis may be made by clinical observation and assessment and/or through diagnostic testing recognized as acceptable by those skilled in the art for determining the amount and/or duration of therapy.

"Effective amount" as used herein refers to an amount of a compound, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent," "preventing," or "prevention of" (and grammatical variations thereof) refer to prevention and/or delay of the onset and/or progression of a metabolic disease in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

C. PHARMACEUTICAL FORMULATIONS

The active compounds described herein may be formulated for administration in a pharmaceutical carrier in accordance with known techniques. See, e.g., Remington, *The Science And Practice of Pharmacy* ($9^{th}$ Ed. 1995). In particular, active compounds of the present invention can be combined with a pharmaceutically acceptable carrier to provide pharmaceutical formulations thereof. The particular choice of carrier and formulation will depend upon the particular route of administration for which the composition is intended.

The compositions of the present invention may be suitable for parenteral, oral, inhalation spray, topical, rectal, nasal, buccal, vaginal or implanted reservoir administration, etc. The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration.

For oral administration, the active compounds may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Formulations suitable for buccal (sub-lingual) administration include lozenges comprising the active compound in a flavoured base, usually sucrose and *acacia* or tragacanth; and pastilles comprising the compound in an inert base such as gelatin and glycerin or sucrose and *acacia*.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The amount of the compounds of the present invention that may be combined with the carrier materials to produce a composition in a single dosage form will vary depending upon the subject treated and the particular route of administration. Preferably, the compositions should be formulated so that a dosage of between 0.01-100 mg/kg body weight/day of the active agent can be administered to a patient receiving these compositions. In certain embodiments, the compositions of the present invention provide a dosage of between 0.01 mg and 50 mg is provided. In other embodiments, a dosage of between 0.1 and 25 mg or between 5 mg and 40 mg is provided.

In an attempt to enhance the action (e.g., therapeutic effect for metabolic disorders) of the compound of the present invention and/or decrease the amount of the compound of the present invention to be used and the like, as well as prevent or treat complications and improve prognosis, for example, the compound of the present invention can be used in combination with a concomitant drug that does not adversely influence the compound of the present invention. Examples of such concomitant drug include an "agent for treating diabetes", "therapeutic drug for diabetic complications", "anti-obesity agent", "therapeutic drug for hypertension", "therapeutic drug for hyperlipidemia", "antiarteriosclerotic drug", "antithrombotic", "diuretic", "therapeutic drug for arthritis", "antianxiety drug", "antidepressant", "psychoneurotic agent", "sleep-inducing drug" and the like. These concomitant drugs may be low-molecular-weight compounds, or high-molecular-weight proteins, polypeptides, antibodies, vaccines or the like. In addition, two or more kinds of these concomitant drugs may be used in combination at an appropriate ratio.

Examples of the above-mentioned "agent for treating diabetes" include insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably, benzoate), Vildagliptin, Sitagliptin, Saxagliptin, B11356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), 133 agonists (e.g., N-5984), GPR40 agonists (e.g., compound described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, Liraglutide, Exenatide, AVE-0010, BIM-51077, Aib(8,35)hGLP-1(7,37) $NH_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance-improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF2 1, FGF analogue and the like.

Examples of the above-mentioned "therapeutic drug for diabetic complications" include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF and neurotrophin production/secretion promoting agents described in WO01/14372 (e.g., 4-(4-chlorophenyl)-2-(2-methyl-1-imidazolyl)-5-[3-(2-methylphenoxy)propyl]oxazole), the compounds described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin-norepinephrine reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitor and the like.

Examples of the above-mentioned "anti-obesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA-modulating agents (e.g., topiramate), neuropeptide γ antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NFic inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like-peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide γ agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), anorexigenic agents (e.g., P-57) and the like.

Examples of the above-mentioned "therapeutic drug for hypertension" include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine), β blockers (e.g., metoprolol, atenolol, propranolol, carvedilol, pindolol), clonidine and the like.

Examples of the above-mentioned "therapeutic drug for hyperlipidemia" include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., the compounds described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), librate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., zetia), CETP inhibitors (e.g., dalcetrapib, anacetrapib), ω-3 fatty acid preparations (e.g., ω-3-acid ethyl esters 90) and the like.

Examples of the above-mentioned "antiarteriosclerotic drug" include acyl coenzyme A cholesterol acyltransferase (ACAT) inhibitors (e.g., K-604), LpPLA2 inhibitors (e.g., darapladib, rilapladib), FLAP inhibitors (e.g., AM103, AM803 and the like), 5LO inhibitors (e.g., VIA-2291), sPLA2 inhibitors (e.g., A-002), apoAI mimetic peptides (e.g., D4F), HDL preparations (e.g., CSL-111) and the like.

Examples of the above-mentioned "antithrombotic" include heparin (e.g., heparin sodium, heparin calcium, enoxaparin sodium, dalteparin sodium), warfarin (e.g., warfarin potassium), anti-thrombin drugs (e.g., aragatroban, dabigatran), FXa inhibitors (e.g., rivaroxaban, apixaban, edoxaban, YM150, the compounds described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the above-mentioned "diuretic agent" include xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, bentylhydrochlorothiazide, penflutiazide, polythiazide, methyclothiazide), antialdosterone preparations (e.g., spironolactone, triamterene), carbonic anhydrase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like.

Examples of the above-mentioned "therapeutic drug for arthritis" include ibuprofen and the like.

Examples of the above-mentioned "antianxiety drug" include alprazolam, etizolam, oxazolam, tandospirone, cloxazolam, clotiazepam, clorazepate dipotassium, chlordiazepoxide, diazepam, fludiazepam, flutazolam, flutoprazepam, prazepam, bromazepam, prazepam, bromazepam, mexazolam, medazepam, ethyl loflazepate, lorazepam and the like.

Examples of the above-mentioned "antidepressant" include tricyclic antidepressants (e.g., imipramine, trimipramine, clomipramine, amitriptyline, nortriptyline, amoxapine, lofepramine, dosulepin, desipramine), tetracyclic antidepressants (e.g., maprotiline, mianserin, Japanese parsley purine), selective serotonin uptake inhibitors (e.g., fluoxetine, fluvoxamine, paroxetine, sertraline, escitalopram), serotonin noradrenaline uptake inhibitors (e.g., milnaeipran, duloxetine, venlafaxine), trazodone, mirtazapine, moclobemide and the like.

Examples of the above-mentioned "psychoneurotic agent" include conventional antipsychotic agents (e.g., clocapramine, chlorpromazine, phenobarbital, sultopride, tiapride, thioridazine, floropipamide, mosapramine, moperone, oxypertine, carpipramine, spiperone, sulpiride, zotepine, timiperone, nemonapride, haloperidol, pimozide, prochlorperazine, propericiazine, bromperidol, perphenazine, fluphenazine maleate, mizoribine, levomepromazine), atypical antipsychotic agents (e.g., perospirone, olanzapine, quetiapine, risperidone, clozapine, aripiprazole, ziprasidone, blonanserin, lurasidone) and the like.

Examples of the above-mentioned "sleep-inducing drug" include Ramelteon, GABAergic hypnotics brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol); non-GABAergic hypnotics (e.g., eplivanserin, pruvanserin, diphenhydramine, trazodone, doxepin) and the like.

The administration time of the aforementioned concomitant drug is not limited, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The compounding ratio of the compound of the present invention to the concomitant drug can be appropriately selected depending on the administration subject, administration route, diseases and the like.

D. SYNTHESIS OF COMPOUNDS

The compounds of the present invention can be prepared readily according to the following schemes and specific examples, or modifications thereof, using readily available staring materials, reagents and conventional synthesis procedures. In these reactions, it is possible to make use of variants which are themselves known to those of ordinary skill in this art but not mentioned in greater detail. The general procedure for making the compounds claimed in this invention can be readily understood and appreciated by one skilled in the art from viewing the following Schemes.

The synthesis of some amides may be conducted as described in Scheme 1.

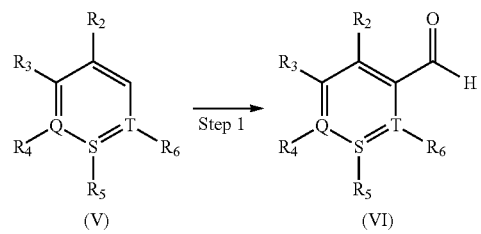

Scheme 1

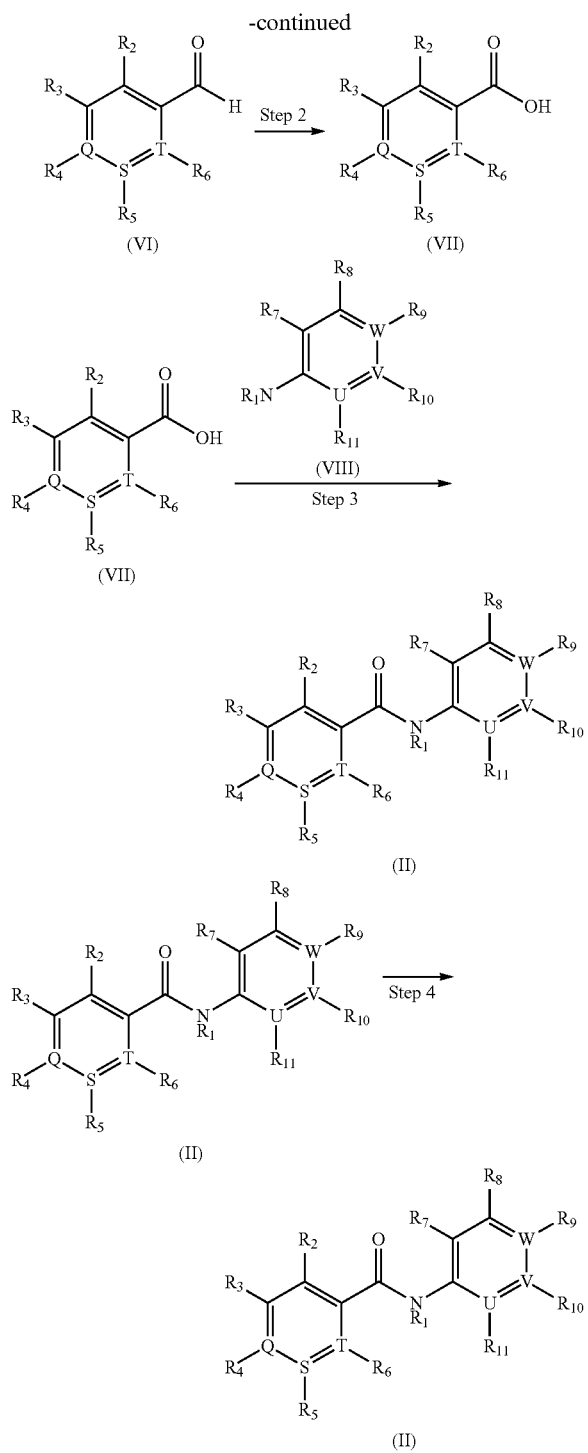

invention. Methodologies for the synthesis of such aldehydes may be found in the following publication: J. Organometallic Chem., Vol. 683, 103-113, 2003. This reference is included as an illustrative example only and should not be interpreted as exhaustive or limiting the invention in any way.

In Step 2, an aldehyde of General Formula (VI) is treated with an oxidizing agent to give a carboxylic acid of General Formula (VII) by means well known in the art such as, for example, treatment with sodium chlorite may be employed. There are many known examples of aldehydes that may be used to make the carboxylic acids of the present invention. Methodologies for the synthesis of such acids may be found in the following publication: WO2005/110996A1. This reference is included as an illustrative example only and should not be interpreted as exhaustive or limiting the invention in any way. Most of the carboxylic acids used to prepare the compounds of the present invention are readily available from commercial sources.

Step 3, illustrates a general strategy for the synthesis of compounds of the present invention via coupling of a carboxylic acid of the General Formula (VII) with an amine of the General Formula (VIII) to give amide of General Formula (II). The amine derivative represented by General Formula (VIII) can be obtained from commercial sources or prepared by methods well known in the art. Methodologies for the synthesis of such amines may be found in the following publications: US20090186879; and Med. Chem. Lett., Vol 2, 402-406, 2011. These references are included as illustrative examples only and should not be interpreted as exhaustive or limiting the invention in any way. Amino acids can be treated with a preformed solution of thionyl chloride and methanol to generate amino acid esters as described in J. Med. Chem., 54, 7815-7833 (2011).

Amide coupling agents may be successfully employed in this reaction. For example, carboxylic acid of General Formula (VII) can be treated with phosphorus trichloride, in the presence of the amine of General Formula (VIII) and an organic solvent, such as, but not limited to, xylenes. Alternatively, carboxylic acid of General Formula (VII) can be treated with HOBt, an organic base, a carbodiimide and amine of General Formula (VIII) with an organic solvent such as, but not limited to dichloromethane. Methodologies for the synthesis of such amides may be found in the following publication: WO2010/101648A1. This reference is included as an illustrative example only and should not be interpreted as exhaustive or limiting the invention in any way.

Step 4, illustrates a general strategy for the synthesis of compounds of the present invention via saponification of ester of General Formula (II) with hydroxide and water/ethanol as solvent to give carboxylic acid of General Formula (II).

Scheme 1 illustrates a general strategy for the preparation of compounds of General Formulas (I) and (II) of the present invention. As will be readily appreciated by those skilled in the art, there are many variations of the routes shown in Scheme 1 that may be useful for synthesizing compounds of the General Formula (II).

In Step 1, a compound of General Formula (V) is formylated to give an aldehyde of General Formula (VI). Standard formylating conditions may be successfully employed in this reaction. There are many known examples of compounds that may be used to make the compounds of the present

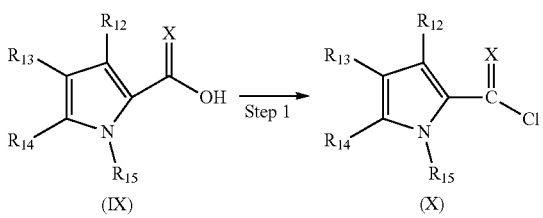

-continued

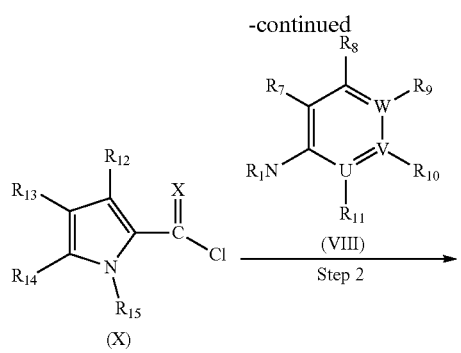

(X)

(IV)

Scheme 2 illustrates a general strategy for the synthesis of the compounds of General Formula (IV). As will be readily appreciated by those skilled in the art, there are many variations of the routes shown in Scheme 2 that may be useful for synthesizing compounds of the General Formula (IV). In Step 1, the acid chloride of General Formula (X) may prepared from the carboxylic acid of General Formula (IX) using literature procedures well known to those skilled in the art, such as for example, heating with excess thionyl chloride. In Step 2, the acid chloride is treated with an amine of the General Formula (VIII) in the presence of an organic base and an organic solvent such as, but not limited to, dichloromethane.

In some embodiments, one or more isotopes may be incorporated into a compound of the present invention. The present invention includes all pharmaceutically acceptable isotopically-labeled compounds of Formula (I)-(X) wherein at least one atom in the compound is replaced with an atom having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$ and sulphur, such as $^{35}S$.

Certain isotopically-labeled compounds of Formula (I)-(X), for example, those incorporating a radioactive isotope, may be useful in drug and/or substrate tissue distribution studies. In some embodiments, the radioactive isotopes tritium, i.e. $^3H$, and carbon-14, i.e. $^{14}C$, may be useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, may be useful in Positron Emission Topography (PET) studies for examining substrate receptor occupancy.

Isotopically-labeled compounds of Formula (I)-(X) can generally be prepared by conventional techniques known to those skilled in the art or by processes analogous to those described in the accompanying Examples using an appropriate isotopically-labeled reagent in place of the non-labeled reagent previously employed.

In some cases the final product may be further modified, for example, by manipulation of substituents. These manipulations may include, but are not limited to, reduction, oxidation, alkylation, and acylation reactions which are commonly known to those skilled in the art.

Simple modifications of these routes, including different protecting group strategies may be employed. Application of well-precedented methodologies, and the use of starting materials and reagents other than those described in the foregoing schemes, may be used to provide other compounds of interest, such as those detailed in Examples 1-94.

EXAMPLES

Some aspects of the present invention are described in more detail in the following non-limiting Examples. These are not intended to restrict the present invention, and may be modified within the range not deviating from the scope of this invention.

The "room temperature" in the following Examples and Experimental Examples means a temperature of about 15° C. to 30° C. For drying an organic layer, anhydrous magnesium sulfate or anhydrous sodium sulfate was employed. Unless otherwise specifically indicated, "%" means percent by weight. In the following examples all chromatography was performed on a Teledyne-ISCO Combiflash $R_f$ system unless otherwise noted.

Abbreviations used in the present specification mean the following: Ac=acetyl, Me=methyl, s=singlet, d=doublet, t=triplet, q=quartet, dd=double doublet, dt=double triplet, m=multiplet, br=broad, T=coupling constant, Hz=Hertz, CDCl$_3$=deuterated chloroform, DMSO-d6=deuterated dimethyl sulfoxide, DMA=dimethylacetamide, THF=tetrahydrofuran, NMP: 1-methyl-2-pyrrolidone, DMF=N,N-dimethylformamide, DMSO: dimethyl sulfoxide, $^1$H-NMR=proton nuclear magnetic resonance, FABMS (pos)=mass spectrum measured by the (+) method in the Fast Atom Bombardment Mass Spectrometry.

Precursor compounds may be obtained from the following commercial suppliers: Areas Organics—distributor: Fischer Scientific, 2000 Park Lane Dr., Pittsburgh, Pa. 15275; Activate Scientific GmbH, Am Mitterweg 12 Prien, D-83209 Germany; Alfa Aesar, 26 Parkridge Road Ward Hill, Mass. 01835 USA; Fluka—distributor—Sigma Aldrich, P.O. Box 14508, St. Louis, Mo.; Matrix Scientific, PO BOX 25067, Columbia, S.C. 29224-5067; Maybridge—distributor Fisher Scientific, 2000 Park Lane Dr., Pittsburgh, Pa.; MP Biomedicals, LLC, 29525 Fountain Pkwy. Solon, Ohio 44139, USA; Oakwood Products, 1741 Old Dunbar Rd. West Columbia, S.C. 29172 USA; Sigma Aldrich, P O Box 14508, St. Louis, Mo. 63178, USA; and TCI America, 9211 N. Harborgate St., Portland, Oreg. 97203, USA.

SYNTHETIC EXAMPLES

Example 1: Methyl 3-chloro-4-{[2-hydroxy-5-trifluoromethyl)benzene]amido}benzoate

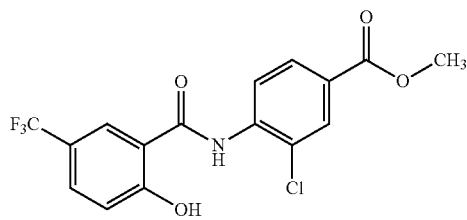 [SMILES: COC(=O)c1ccc(NC(=O)c2cc(C(F)(F)F)ccc2O)c(Cl)c1]

Step 1: 2-hydroxy-5-(trifluoromethyl)benzaldehyde

The following procedure was adapted from that described in *J Organometallic Chem* 683 2003 103-113. To a solution of 4-trifluoromethylphenol (5.0 g, 0.31 mol) [Activate Scientific GmbH] in acetonitrile (140 mL) at ambient temperature was added triethylamine (11.4 g, 0.113 mol) followed by $MgCl_2$ (4.5 g, 0.47 mol). The resulting mixture was stirred at ambient temperature for 15 min. during which a slight exotherm was observed. Paraformaldehyde (6.2 g, 0.206 mol) was added and the mixture was heated at reflux for 3 h. Let cool to ambient temperature and poured the mixture into 10% aqueous HCl (260 mL). The mixture was stirred for 30 min. at ambient temperature, then extracted several times with diethyl ether. The combined organic phase was washed with brine and dried over $MgSO_4$. The mixture was filtered and silica gel was added to the filtrate. This was concentrated in vacuo, transferred to a pre-column, and purified by chromatography using a gradient as follows: initially hexane (20 min.), then the eluent was modified to 10% EtOAc/hexane over a 10 min. period and kept at 10% EtOAc/hexane for the remainder of the purification. The fractions containing the pure fastest eluting main component were combined and concentrated in vacuo to get 1.77 g (30% yield) of 2-hydroxy-5-(trifluoromethyl)-benzaldehyde as a white solid.

MS: m/z 189 ($MH^-$).

$^1H$ NMR (500 MHz, DMSO-$d_6$): δ 7.196 (d, 1H), 7.848 (dd, 1H), 7.922 (br d, 1H), 10.312 (s, 1H), 11.555 (br s, 1H).

Step 2: 2-hydroxy-5-(trifluoromethyl)benzoic acid

The following procedure was adapted from that described in WO2005110996A1: To a flask charged with 2-hydroxy-5-(trifluoromethyl)benzaldehyde (1.6 g, 0.008 mol) was added 2-methyl-2-butene (40 mL, 0.08 mol) as a 2M solution in THF. Tert-butanol (40 mL) was added. While vigorously stirring the resulting mixture, a solution of sodium dihydrogen phosphate (3.0 g, 0.025 mol) and sodium chlorite (1.53 g, 0.017 mol) in 16 mL of water was added dropwise. After the addition was complete, the mixture was stirred at ambient temperature for 2.5 h. The mixture was diluted with ethyl acetate (150 mL) and washed with 1N aqueous HCl (200 mL). The aqueous phase was back extracted with ethyl acetate and the combined organic phase was washed with a saturated aqueous solution of sodium thiosulfate (150 mL), then brine. The solution was dried over MgSO4, filtered and concentrated in vacuo to give 2.02 g of 2-hydroxy-5 (trifluoromethyl)-benzoic acid as a white solid, MS: m/z 205 ($MH^-$).

$^1H$ NMR (500 MHz, DMSO-$d_6$): δ 7.146 (d, 1H), 7.827 (dd, 1H), 8.089 (br d, 1H), 11.109 (br s, 1H), 13.671 (br s, 1H). NMR indicated the presence of a small amount of the aldehyde and 2-methyl-2-butene. This material was used without further purification.

Step 3: Methyl 3-chloro-4-{[2-hydroxy-5-(trifluoromethyl)benzene]amido}benzoate

This procedure was adopted from a procedure described in WO2010101648A1 with some modifications. A mixture of 5-trifluoromethylsalicylic acid (0.49 g, 0.0024 mol) and methyl 4-amino-3-chlorobenzoate (0.45 g, 0.0024 mol)[Acros Organics] in Xylenes (15 mL) was heated to 100° C. $PCl_3$ (0.54 mL, 0.0011 mol) as a 2M solution in dichloromethane was added dropwise via syringe. The mixture was heated at 130° C. for 5 hr. The temperature was reduced to 100° C. and the hot solution was pipetted into an Erlenmeyer flask. The hot solution was stirred vigorously while cooling to room temperature. The resulting solid was filtered, washed several times with hexane and air dried to 0.359 g of crude product as a white solid. The solid was dissolved in ethyl acetate, silica gel was added and the mixture was concentrated in vacuo. The residue was transferred to a pre-column and purified by chromatography using a gradient as follows: initially hexane (1 min.), then the eluent was modified to 30% ethyl acetate/hexane over a 12 min. period and then kept at 30% ethyl acetate/hexane for the remainder of the purification. The fractions containing the pure major component were combined and concentrated in vacuo to give 0.297 g (33%) of methyl 3-chloro-4-{[2-hydroxy-5-(trifluoromethyl)benzene]amido}benzoate as a white solid.

MS: m/z 372 ($MH^-$).

$^1H$ NMR (500 MHz, DMSO-$d_6$): δ 3.873 (s, 3H), 7.257 (d, 1H), 7.841 (dd, 1H), 7.996 (dd, 1H), 8.066 (d, 1H), 8.317 (br d, 1H), 8.697 (d, 1H), 11.179 (s, 1H), 13.036 (br s, 1H).

Example 2: 3-Chloro-4-{[2-hydroxy-5-(trifluoromethyl)benzene]amido}benzoic acid

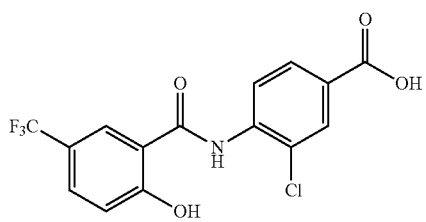 [SMILES: O=C(O)c1ccc(NC(=O)c2cc(C(F)(F)F)ccc2O)c(Cl)c1]

Methyl 3-chloro-4-{[2-hydroxy-5-(trifluoromethyl)benzene]amido}benzoate [Example 1] (0.13 g, 0.35 mmol) was placed in ethanol (4.2 mL) at ambient temperature. Aqueous sodium hydroxide (4.2 mL, 0.42 mmol) as a 1M solution was added in one portion and the mixture was stirred at ambient temperature for 4 h. The pH was adjusted to ~1 with 1N HCl (aq.) and the mixture was concentrated in vacuo to remove the ethanol. To the aqueous residue was added ethyl acetate and water. The phases were separated and the aqueous phase was extracted with ethyl acetate. The combined organic phase was washed with water, then brine and dried over sodium sulfate. The mixture was filtered and concentrated in vacuo to give a quantitative yield of 3-Chloro-4-{[2-hydroxy-5-(trifluoromethyl)-benzene]amido}benzoic acid as a white solid.

MS: m/z 358 (MH⁻).

¹H NMR (500 MHz, DMSO-d₆): δ 7.310 (d, 1H), 7.895 (dd, 1H), 8.028 (dd, 1H), 8.096 (d, 1H), 8.379 (d, 1H), 8.721 (d, 1H), 11.223 (s, 1H), 13.078 (br s, 1H), 13.233 (br s, 1H).

Example 3: Methyl 4[(5-tert-butyl-2-hydroxybenzene)amido]-3-chlorobenzoate

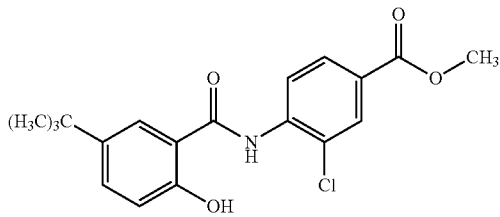

Methyl 4-[(5-tert-butyl-2-hydroxybenzene)amido]-3-chlorobenzoate was prepared in a similar manner as described in Example 1, step 3 using 5-tert-butyl-2-hydroxybenzoic acid [prepared as described in WO2005110996A1] in place of 2-hydroxy-5-(trifluoromethyl)benzoic acid to obtain methyl 4-[(5-tert-butyl-2-hydroxybenzene)amido]-3-chlorobenzoate as a white solid in a 38% yield.

MS: m/z 360 (MH⁻) and m/z 362 (MH⁺).

¹H NMR (500 MHz, DMSO-d₆): δ 1.287 (s, 9H), 3.64 (s, 3H), 7.010 (d, 1H), 7.531 (dd, 1H), 7.970 (dd, 1H), 8.045 (br s, 1H), 8.050 (br d, 1H), 8.727 (d, 1H), 11.233 (s, 1H), 11.826 (br s, 1H).

Example 4: 4-[(5-tert-butyl-2-hydroxybenzene)amido]-3-chlorobenzoic acid

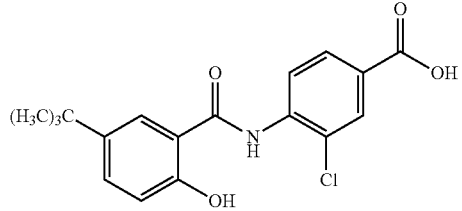

4-[(5-tert-butyl-2-hydroxybenzene)amido]-3-chlorobenzoic acid was prepared in a similar manner as described in Example 2 substituting methyl 4-[(5-tert-butyl-2-hydroxybenzene)amido]-3-chlorobenzoate [Example 3] for methyl 3-chloro-4-{[2-hydroxy-5-(trifluoromethyl)benzene]amido}benzoate to give 4-[(5-tert-butyl-2-hydroxybenzene)amido]-3-chlorobenzoic acid as a white solid in a quantitative yield.

MS: m/z 346 (MH⁻) and m/z 348 (MH⁺).

¹H NMR (500 MHz, DMSO-d₆): δ 1.288 (s, 9H), 7.008 (d, 1H), 7.529 (dd, 1H), 7.945 (dd, 1H), 8.019 (d, 1H), 8.051 (d, 1H), 8.691 (d, 1H), 11.207 (s, 1H), 11.812 (br s, 1H), 13.117 (br s, 1H).

Example 5: Methyl 3-chloro-4-[(5-chloro-2-hydroxybenzene)amido]benzoate

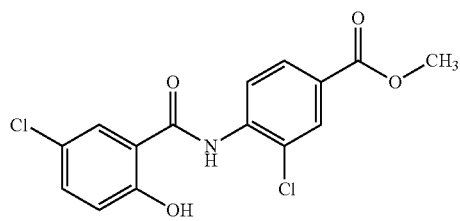 [SMILES: COC(=O)c1ccc(NC(=O)c2cc(Cl)ccc2O)c(Cl)c1]

Methyl 3-chloro-4-[(5-chloro-2-hydroxybenzene)amido]benzoate was prepared in a similar manner as described in Example 1, step 3 using 5-chloro-2-hydroxybenzoic [MP Biomedicals, LLC] in place of 2-hydroxy-5-(trifluoromethyl)benzoic acid. The initial crude solid was triturated with a hot ethyl acetate/MeOH mixture and filtered to get a first crop of solid. A second crop of solid was obtained by adding hexanes to the filtrate from the first crop to give methyl 3-chloro-4-[(5-chloro-2-hydroxybenzene)amido]benzoate both as white solids in a 34% total yield.

MS: m/z 338 (MH⁻) and m/z 340 (MH⁺).

¹H NMR (500 MHz, DMSO-d₆): δ 3.866 (s, 3H), 7.097 (d, 1H), 7.531 (dd, 1H), 7.981 (m, 2H), 8.051 (br d, 1H), 8.690 (d, 1H), 11.117 (s, 1H), 12.398 (s, 1H).

Example 6: 3-chloro-4-[(5-chloro-2-hydroxy benzene)amido]benzoic acid

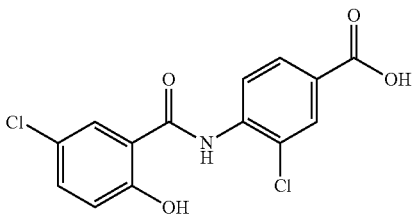 [SMILES: O=C(O)c1ccc(NC(=O)c2cc(Cl)ccc2O)c(Cl)c1]

3-chloro-4-[(5-chloro-2-hydroxy benzene)amido]benzoic acid was prepared in a similar manner as described in Example 2 substituting methyl 3-chloro-4-[(5-chloro-2-hydroxybenzene)amido]-benzoate [Example 5] for methyl 3-chloro-4-{[2-hydroxy-5-(trifluoromethyl)benzene]amido}benzoate to give 3-chloro-4-[(5-chloro-2-hydroxy benzene)amido]benzoic acid as a white solid in a quantitative yield.

MS: m/z 324 (MH⁻).

¹H NMR (500 MHz, DMSO-d₆): δ 7.094 (d, 1H), 7.527 (dd, 1H), 7.956 (dd, 1H), 7.980 (d, 1H), 8.025 (d, 1H), 8.656 (d, 1H), 11.170 (s, 1H), 12.399 (br s, 1H), 13.149 (br s, 1H).

Example 7: Methyl 3-chloro-4-[(5-fluoro-2-hydroxybenzene)amido]benzoate

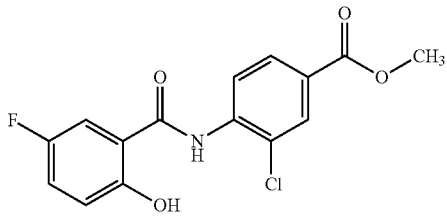 [SMILES: COC(=O)c1ccc(NC(=O)c2cc(F)ccc2O)c(Cl)c1]

Methyl 3-chloro-4-[(5-fluoro-2-hydroxybenzene)amido]benzoate was prepared in a similar manner as described in Example 1, step 3 using 5-fluoro-2-hydroxybenzoic [Matrix Scientific] in place of 2-hydroxy-5-(trifluoromethyl)benzoic acid to obtain methyl 3-chloro-4-[(5-fluoro-2-hydroxybenzene)-amido]benzoate as an off-white solid in a 64% yield.

MS: m/z 322 (MH$^-$) and m/z 324 (MH$^+$).

$^1$H NMR (500 MHz, DMSO-d$_6$): δ 3.865 (s, 3H), 7.087 (dd, 1H), 7.365 (m, 1H), 7.736 (dd, 1H), 7.978 (d, 1H), 8.050 (d, 1H), 8.703 (d, 1H), 11.259 (br s, 1H), 12.111 (br s, 1H).

Example 8: 3-chloro-4-[(5-fluoro-2-hydroxybenzene)amido]benzoic acid

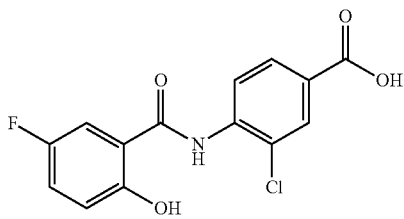 [SMILES: O=C(O)c1ccc(NC(=O)c2cc(F)ccc2O)c(Cl)c1]

3-chloro-4-[(5-fluoro-2-hydroxybenzene)amido]benzoic acid was prepared in a similar manner as described in Example 2 substituting methyl 3-chloro-4-[(5-fluoro-2-hydroxybenzene)amido]benzoate [Example 7] for methyl 3-chloro-4-{[2-hydroxy-5-(trifluoromethyl)benzene]amido}benzoate to give 3-chloro-4-[(5-fluoro-2-hydroxybenzene)amido]benzoic acid as a white solid in a quantitative yield.

MS: m/z 308 (MH$^-$).

$^1$H NMR (500 MHz, DMSO-d$_6$): δ 7.145 (dd, 1H), 7.424 (m, 1H), 7.802 (dd, 1H), 8.015 (m, 1H), 8.087 (d, 1H), 8.732 (d, 1H), 11.301 (s, 1H), 12.155 (br s, 1H), 13.203 (br s, 1H).

Example 9: Methyl 3-chloro-4-[(2-hydroxy-5-methoxybenzene)amido]benzoate

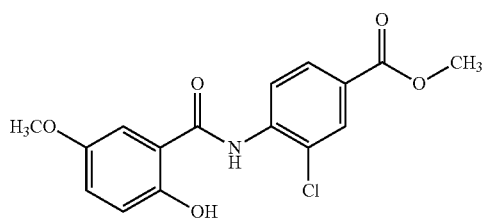 [SMILES: COC(=O)c1ccc(NC(=O)c2cc(OC)ccc2O)c(Cl)c1]

Methyl 3-chloro-4-[(2-hydroxy-5-methoxybenzene)amido]benzoate was prepared in a similar manner as described in Example 1, step 3 using 2-hydroxy-5-methoxybenzoic acid [Aldrich] in place of 2-hydroxy-5-(trifluoromethyl)benzoic acid to obtain methyl 3-chloro-4-[(2-hydroxy-5-methoxybenzene)-amido]benzoate as an off-white solid in a 35% yield.

MS: m/z 334 (MH$^-$) and m/z 336 (MH$^+$).

$^1$H NMR (500 MHz, DMSO-d$_6$): δ 3.758 (s, 3H), 3.863 (s, 3H), 7.010 (d, 1H), 7.107 (dd, 1H), 7.543 (d, 1H), 7.971 (dd, 1H), 8.043 (d, 1H), 8.726 (d, 1H), 11.319 (br s, 1H), 11.612 (br s, 1H).

Example 10: 3-chloro-4-[(2-hydroxy-5-methoxybenzene)amido]benzoic acid

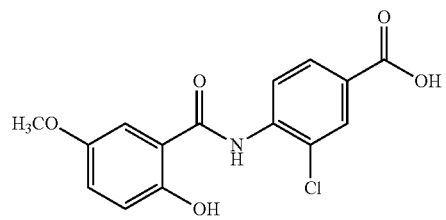 [SMILES: COc1ccc(O)c(C(=O)Nc2ccc(C(=O)O)cc2Cl)c1]

3-chloro-4-[(2-hydroxy-5-methoxybenzene)amido]benzoic acid was prepared in a similar manner as described in Example 2 substituting methyl 3-chloro-4-[(2-hydroxy-5-methoxybenzene)amido]benzoate [Example 9] for methyl 3-chloro-4-{[2-hydroxy-5-(trifluoromethyl)benzene]amido}benzoate to give 3-chloro-4-[(2-hydroxy-5-methoxybenzene)amido]benzoic acid as an off-white solid in a 45% yield. Note: This material was triturated with hexanes and filtered to obtain the final product.

MS: m/z 320 (MH$^-$) and m/z 322 (MH$^+$).

$^1$H NMR (500 MHz, DMSO-d$_6$): δ 3.759 (s, 3H), 7.009 (d, 1H), 7.106 (dd, 1H), 7.549 (d, 1H), 7.948 (m, 1H), 8.021 (d, 1H), 8.697 (d, 1H), 11.308 (s, 1H), 11.619 (br s, 1H), 13.131 (br s, 1H).

Example 11: Methyl 3-chloro-4-[(2-hydroxy-5-methylbenzene)amido]benzoate

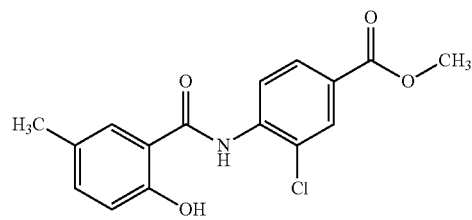

Methyl 3-chloro-4-[(2-hydroxy-5-methylbenzene)amido]benzoate was prepared in a similar manner as described in Example 1, step 3 using 2-hydroxy-5-methylbenzoic acid [Aldrich] in place of 2-hydroxy-5-(trifluoromethyl)benzoic acid to obtain methyl 3-chloro-4-[(2-hydroxy-5-methylbenzene)-amido]benzoate as a white solid in a 45% yield.

MS: m/z 318 (MH$^-$) and m/z 320 (MH$^+$).

$^1$H NMR (500 MHz, DMSO-d$_6$): δ 2.284 (s, 3H), 3.864 (s, 3H), 6.968 (d, 1H), 7.288 (dd, 1H), 7.844 (d, 1H), 7.974 (dd, 1H), 8.045 (d, 1H), 8.722 (d, 1H), 11.243 (br s, 1H), 11.786 (br s, 1H).

Example 12: 3-chloro-4-[(2-hydroxy-5-methylbenzene)amido]benzoic acid

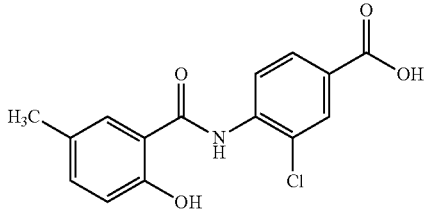 [SMILES: Cc1ccc(O)c(C(=O)Nc2ccc(C(=O)O)cc2Cl)c1]

3-Chloro-4-[(2-hydroxy-5-methylbenzene)amido]benzoic acid was prepared in a similar manner as described in Example 2 substituting methyl 3-chloro-4-[(2-hydroxy-5-methyl benzene)amido]benzoate [Example 11] for methyl 3-chloro-4-{[2-hydroxy-5-(trifluoromethyl)benzene]amido}benzoate to give 3-chloro-4-[(2-hydroxy-5-methylbenzene)amido]benzoic acid as an off-white solid in a 95% yield. Note: This material was triturated with hexanes and filtered to obtain the final product.

MS: m/z 304 (MH$^-$) and m/z 306 (MH$^+$).

$^1$H NMR (500 MHz, DMSO-d$_6$): δ 2.285 (s, 3H), 6.965 (d, 1H), 7.285 (dd, 1H), 7.847 (d, 1H), 7.946 (dd, 1H), 8.016 (d, 1H), 8.687 (d, 1H), 11.217 (s, 1H), 11.779 (br s, 1H), 13.119 (br s, 1H).

Example 13: Methyl 4-[(5-tert-butyl-2-hydroxybenzene)amido]-3-fluorobenzoate

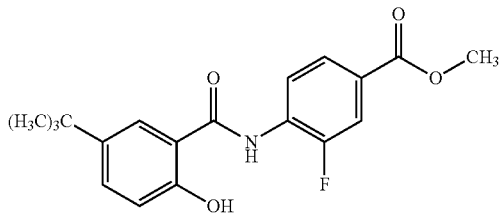 [SMILES: COC(=O)c1ccc(NC(=O)c2cc(C(C)(C)C)ccc2O)c(F)c1]

Methyl 4-[(5-tert-butyl-2-hydroxybenzene)amido]-3-fluorobenzoate was prepared in a similar manner as described in Example 1, step 3 using 5-tert-butyl-2-hydroxy benzoic acid in place of 2-hydroxy-5-(trifluoromethyl)benzoic acid and methyl 4-amino-3-fluorobenzoate (Oakwood Products, Inc.) in place of methyl 4-amino-3-chlorobenzoate to obtain methyl 4-[(5-tert-butyl-2-hydroxybenzene)amido]-3-fluorobenzoate as a white solid in a total yield of 33%. NOTE: The product was isolated in two batches. The first by recrystallization of the initial crude material from ethanol and the second by chromatography in a similar manner as described in Example 1, step 3.

MS: m/z 344 (MH$^-$) and m/z 346 (MH$^+$).

$^1$H NMR (500 MHz, DMSO-d$_6$): δ 1.280 (s, 9H), 3.855 (s, 3H), 6.983 (d, 1H), 7.516 (dd, 1H), 7.803 (dd, 1H), 7.848 (dd, 1H), 8.016 (d, 1H), 8.557 (t, 1H), 11.015 (br d, 1H), 11.735 (s, 1H).

Example 14: 4-[(5-tert-butyl-2-hydroxybenzene)amido]-3-fluorobenzoic acid

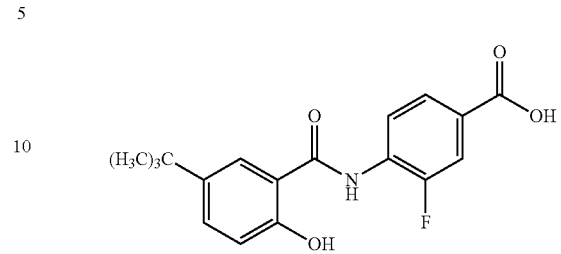

The compound 4-[(5-tert-butyl-2-hydroxybenzene)amido]-3-fluorobenzoic acid was prepared in a similar manner as described in Example 2 substituting methyl 4-[(5-tert-butyl-2-hydroxybenzene)amido]-3-fluorobenzoate [Example 13] for methyl 3-chloro-4-{[2-hydroxy-5-(trifluoromethyl)benzene]-amido}benzoate to give 4-[(5-tert-butyl-2-hydroxybenzene)amido]-3-fluorobenzoic acid as a white solid in a quantitative yield.

MS: m/z 330 (MH$^-$) and m/z 332 (MH$^+$).

$^1$H NMR (500 MHz, DMSO-d$_6$): δ 1.281 (s, 9H), 6.981 (d, 1H), 7.515 (dd, 1H), 7.765 (dd, 1H), 7.821, (dd, 1H), 8.019 (d, 1H), 8.519 (t, 1H), 10.992 (br d, 1H), 11.737 (s, 1H), 13.067 (br s, 1H).

Example 15: Methyl 4-[(5-tert-butyl-2-hydroxybenzene)amido]-3-methylbenzoate

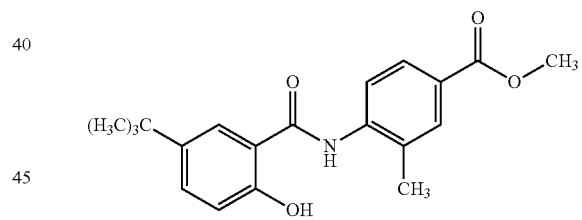

Methyl 4-[(5-tert-butyl-2-hydroxybenzene)amido]-3-methylbenzoate was prepared in a similar manner as described in Example 1, step 3 using 5-tert butyl-2-hydroxy benzoic acid in place of 2-hydroxy-5-(trifluoromethyl)benzoic acid and methyl 4-amino-3-methylbenzoate (Maybridge) in place of methyl 4-amino-3-chlorobenzoate to obtain methyl 4-[(5-tert-butyl-2-hydroxybenzene)amido]-3-methylbenzoate as a white solid in a total yield of 53%. NOTE: The product was isolated in two batches. The first by recrystallization of the initial crude material from ethanol and the second by chromatography in a similar manner as described in Example 1, step 1

MS: m/z 340 (MH$^-$) and m/z 342 (MH$^+$).

$^1$H NMR (500 MHz, DMSO-d$_6$): δ 1.284 (s, 9H), 2.365 (s, 3H), 3.836 (s, 3H), 6.980 (d, 1H), 7.494 (dd, 1H), 7.839 (dd, 1H), 7.875 (br d, 1H), 8.025 (d, 1H), 8.323 (d, 1H), 10.583 (s, 1H), 11.731 (s, 1H).

Example 16: 4-[(5-tert-butyl-2-hydroxybenzene)amido]-3-methylbenzoic acid

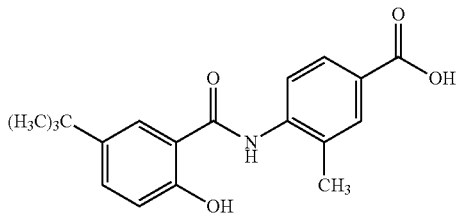 [SMILES: Cc1cc(C(=O)O)ccc1NC(=O)c1cc(C(C)(C)C)ccc1O]

The compound 4-[(5-tert-butyl-2-hydroxybenzene)amido]-3-methylbenzoic acid was prepared in a similar manner as described in Example 2 substituting methyl 4-[(5-tert-butyl-2-hydroxybenzene)-amido]-3-methylbenzoate [Example 15] for methyl 3-chloro-4-{[2-hydroxy-5-(trifluoromethyl)-benzene]amido}benzoate to give 4-[(5-tert-butyl-2-hydroxybenzene)amido]-3-methylbenzoic acid as a white solid in a 95% yield.

MS: m/z 326 (MH$^-$) and m/z 328 (MH$^+$).

$^1$H NMR (500 MHz, DMSO-d$_6$): δ 1.353 (s, 9H), 2.423 (s, 3H), 7.044 (d, 1H), 7.560 (dd, 1H), 7.879 (dd, 1H), 7.919, (br d, 1H), 8.095 (d, 1H), 8.334 (d, 1H), 10.630 (s, 1H), 11.809 (br s, 1H), 12.780 (br s, 1H).

Example 17: 3-Chloro-4-[(2-hydroxybenzene)amido]-N,N-dioxoanilinium

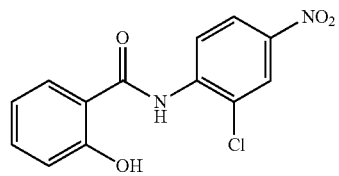 [SMILES: O=C(Nc1ccc([N+](=O)[O-])cc1Cl)c1ccccc1O]

3-Chloro-4-[(2-hydroxybenzene)amido]-N,N-dioxoanilinium was prepared in a similar manner as described in WO/2010/101648A1 from salicylic acid (Aldrich) and 2-chloro-4-nitroaniline (MP Biomedicals, LLC) to give a 43% yield of 3-chloro-4-[(2-hydroxybenzene)amido]-N,N-dioxoanilinium as an off-white solid.

MS: m/z 291 (MH$^-$).

$^1$H NMR (500 MHz, DMSO-d$_6$): δ 7.067 (m, 2H), 7.500 (m, 1H), 8.058 (dd, 1H), 8.302 (dd, 1H), 8.440 (d, 1H), 8.860 (d, 1H), 11.402 (s, 1H), 12.141 (s, 1H).

Example 18: 3-Chloro-4-[(2-hydroxy-5-methylbenzene)amido]-N,N-dioxoanilinium

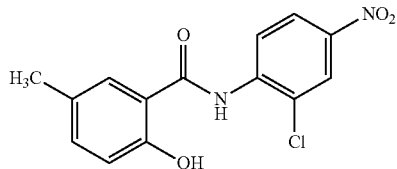 [SMILES: Cc1ccc(O)c(C(=O)Nc2ccc([N+](=O)[O-])cc2Cl)c1]

3-Chloro-4-[(2-hydroxy-5-methylbenzene)amido]-N,N-dioxoanilinium was prepared in a similar manner as described in WO/2010/101648A1 from 2-hydroxy-5-methylbenzoic acid and 2-chloro-4-nitroaniline to give a 33% yield of 3-Chloro-4-[(2-hydroxy-5-methylbenzene)amido]-N,N-dioxoanilinium as an off-white solid.

MS: m/z 305 (MH$^-$).

$^1$H NMR (500 MHz, DMSO-d$_6$): δ 2.286 (s, 3H), 6.995 (d, 1H), 7.302 (m, 1H), 7.844 (d, 1H), 8.294 (dd, 1H), 8.425 (d, 1H), 8.852 (d, 1H), 11.410 (s, 1H), 11.887 (s, 1H).

Example 19: 3-Chloro-4-[(2-hydroxy-5-methoxybenzene)amido]-N,N-dioxoanilinium

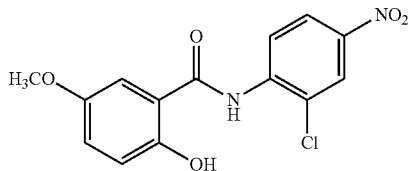 [SMILES: COc1ccc(O)c(C(=O)Nc2ccc([N+](=O)[O-])cc2Cl)c1]

3-Chloro-4-[(2-hydroxy-5-methoxybenzene)amido]-N,N-dioxoanilinium was prepared in a similar manner as described in WO/2010/101648A1 from 2-hydroxy-5-methoxybenzoic acid and 2-chloro-4-nitroaniline to give a 17% yield of 3-Chloro-4-[(2-hydroxy-5-methoxybenzene)amido]-N,N-dioxoanilinium as a tan solid.

MS: m/z 321 (MH$^-$).

$^1$H NMR (500 MHz, DMSO-d$_6$): δ 3.761 (s, 3H), 7.021 (d, 1H), 7.125 (dd, 1H), 7.537 (d, 1H), 8.296 (dd, 1H), 8.432 (d, 1H), 8.855 (d, 1H), 11.491 (s, 1H), 11.719 (s, 1H).

Example 20: 5-Chloro-N-(2-chlorophenyl)-2-hydroxybenzamide

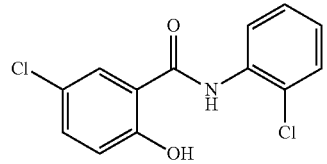 [SMILES: O=C(Nc1ccccc1Cl)c1cc(Cl)ccc1O]

5-Chloro-N-(2-chlorophenyl)-2-hydroxybenzamide was prepared in a similar manner as described in WO/2010/101648A1 from 5-chloro-2-hydroxybenzoic acid and 2-chloroaniline (Fluka) to give an 8% yield of 5-Chloro-N-(2-chlorophenyl)-2-hydroxybenzamide as a white solid.

MS: m/z 280 (MH$^-$).

$^1$H NMR (500 MHz, DMSO-d$_6$): δ 7.077 (d, 1H), 7.199 (m, 1H), 7.401 (m, 1H), 7.511 (dd, 1H), 7.568 (dd, 1H), 7.997 (d, 1H), 8.390 (dd, 1H), 10.879 (s, 1H), 12.248 (s, 1H).

Example 21: 5-Chloro-N-(2-chloro-4-methylphenyl)-2-hydroxybenzamide

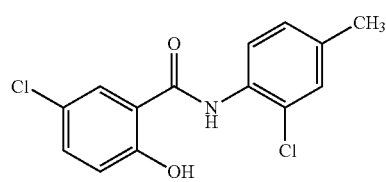 [SMILES: Cc1ccc(NC(=O)c2cc(Cl)ccc2O)c(Cl)c1]

5-Chloro-N-(2-chloro-4-methylphenyl)-2-hydroxybenzamide was prepared in a similar manner as described in WO/2010/101648A1 from 5-chloro-2-hydroxybenzoic acid and 2-chloro-4-methylaniline (Aldrich) to give a 39% yield of 5-chloro-N-(2-chloro-4-methylphenyl)-2-hydroxybenzamide as a white solid.

MS: m/z 294 (MH$^-$) and m/z 296 (MH$^+$).

$^1$H NMR (500 MHz, DMSO-d$_6$): δ 2.307 (s, 3H), 7.064 (d, 1H), 7.203 (dd, 1H), 7.394 (d, 1H), 7.501 (dd, 1H), 7.992 (d, 1H), 8.213 (d, 1H), 10.776 (s, 1H), 12.220 (s, 1H).

Example 22: 3-Chloro-4-[(3-chlorobenzene)amido]-N,N-dioxoanilinium

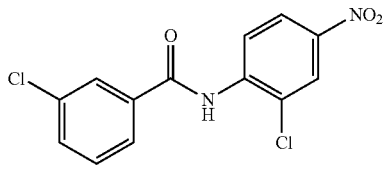 [SMILES: O=C(Nc1ccc([N+](=O)[O-])cc1Cl)c1cccc(Cl)c1]

3-Chloro-4-[(3-chlorobenzene)amido]-N,N-dioxoanilinium was prepared in a similar manner as described in WO/2010/101648A1 from 3-chlorobenzoic acid (ACROS) and 2-chloro-4-nitroaniline to give a 12% yield of 3-chloro-4-[(3-chlorobenzene)amido]-N,N-dioxoanilinium as a pale yellow solid.

MS: m/z 309 (MH$^-$).

$^1$H NMR (500 MHz, DMSO-d$_6$): δ 7.614 (t, 1H), 7.733 (dg, HA 7.958 (dt, 1H), 8.011 (d, 1H), 8.044 (t, 1H), 8.274 (dd, 1H), 8.427 (d, 1H), 10.481 (s, 1H).

Example 23: 5-Chloro-N-(2-chloro-4-methoxyphenyl)-2-hydroxybenzamide

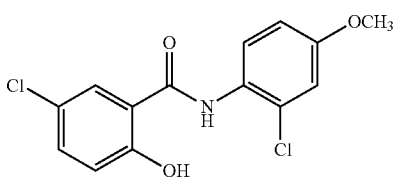 [SMILES: COc1ccc(NC(=O)c2cc(Cl)ccc2O)c(Cl)c1]

Step 1: 2-Chloro-4-methoxyaniline

This compound was prepared in a similar manner as described in US20090186879 from 4-bromo-2-chloroaniline (ACROS) and sodium methoxide to give a 49% yield of 2-Chloro-4-methoxyaniline as a red oil.

MS: m/z 158 (MH$^+$), $^1$H NMR (500 MHz, DMSO-d$_6$): δ 3.644 (s, 3H), 4.825 (s, 2H), 6.686 (dd, 1H), 6.747 (d, 1H), 6.822 (d, 1H).

Step 2, 5-Chloro-N-(2-chloro-4-methoxyphenyl)-2-hydroxybenzamide

This compound was prepared in a similar manner as described in WO/2010/101648A1 from 5-chloro-2-hydroxybenzoic acid and 2-chloro-4-methoxyaniline (Example 23, step 1) to give a 26% yield of 5-chloro-N-(2-chloro-4-methoxyphenyl)-2-hydroxybenzamide as a white solid.

MS: m/z 310 (MH$^-$) and m/z 312 (MH$^+$).

$^1$H NMR (500 MHz, DMSO-d$_6$): δ 3.790 (s, 3H), 6.993 (dd, 1H), 7.053 (d, 1H), 7.165 (d, 1H), 7.498 (dd, 1H), 8.005 (d, 1H), 8.095 (d, 1H), 10.634 (s, 1H), 12.202 (s, 1H).

Example 24: 5-tert-Butyl-N-(2-chloro-4-nitrophenyl)-2-hydroxybenzamide

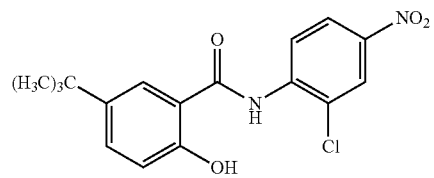 [SMILES: CC(C)(C)c1ccc(O)c(C(=O)Nc2ccc([N+](=O)[O-])cc2Cl)c1]

5-tert-Butyl-N-(2-chloro-4-nitrophenyl)-2-hydroxybenzamide was prepared in a similar manner as described in Example 1, Step 3 from 5-tert-butyl-2-hydroxybenzoic acid [prepared as described in WO2005110996A1] and 2-chloro-4-nitroaniline to give a 16% yield of 5-tert-butyl-N-(2-chloro-4-nitrophenyl)-2-hydroxybenzamide as an off-white solid. (NOTE this exception: this reaction was run for 4 h and worked up in the normal manner to get very little product. The reaction was recombined and a second equivalent of PCl$_3$ was added and the mixture was heated overnight at reflux and the product was isolated in a similar manner as described in Example 1, Step 3).

MS: m/z 347 (MH$^-$) and m/z 349 (MH$^+$).

$^1$H NMR (500 MHz, DMSO-d$_6$): δ 1289 (s, 9H), 7.022 (d, 1H), 7.552 (dd, 1H), 8.049 (d, 1H), 8.299 (dd, 1H), 8.437 (dd, 1H), 8.862 (d, 1H), 11.440 (s, 1H), 11.953 (s, 1H).

Example 25: 5-fluoro-N-(2-chloro-4-nitrophenyl)-2-hydroxybenzamide

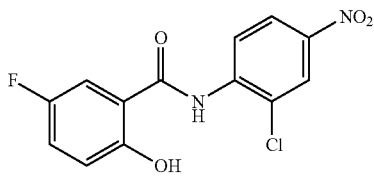 [SMILES: O=C(Nc1ccc([N+](=O)[O-])cc1Cl)c1cc(F)ccc1O]

5-Fluoro-N-(2-chloro-4-nitrophenyl)-2-hydroxybenzamide was prepared in a similar manner as described in Example 1, Step 3 from 5-fluoro-2-hydroxybenzoic acid and 2-chloro-4-nitroaniline to give a 25% yield of 5-fluoro-N-(2-chloro-4-nitrophenyl)-2-hydroxybenzamide as a pale yellow solid.

MS: m/z 309 (MH$^-$), $^1$H NMR (500 MHz, DMSO-d$_6$): δ 7.160 (dd, 1H), 7.448 (qd, 1H), 7.801 (dd, 1H), 8.366 (dd, 1H), 8.506 (d, 1H), 8.894 (d, 1H), 11.495 (s, 1H), 12.295 (s, 1H).

Example 26: N-(4-bromo-2-chlorophenyl)-5-chloro-2-hydroxybenzamide

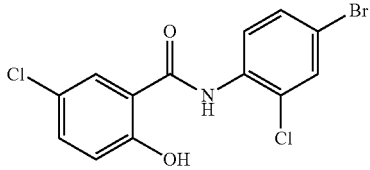 [SMILES: O=C(Nc1ccc(Br)cc1Cl)c1cc(Cl)ccc1O]

N-(4-bromo-2-chlorophenyl)-5-chloro-2-hydroxybenzamide was prepared in a similar manner as described in Example 1, Step 3 from 5-chloro-2-hydroxybenzoic acid and 4-bromo-2-chloroaniline (ACROS) to give a 52% yield of N-(4-bromo-2-chlorophenyl)-5-chloro-2-hydroxybenzamide as a white solid.

MS: m/z 358 (MH$^-$) and m/z 360 (MH$^+$).
$^1$H NMR (500 MHz, DMSO-d$_6$): δ 7.077 (d, 1H), 7.516 (dd, 1H), 7.609 (dd, 1H), 7.849 (d, 1H), 7.972 (d, 1H), 8.383 (d, 1H), 10.920 (s, 1H), 12.288 (s, 1H).

Example 27: 3-Chloro-N,N-dioxo-4-(1H-pyrrole-2-amido)anilinium

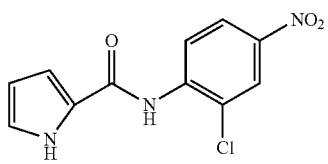 [SMILES: O=C(Nc1ccc([N+](=O)[O-])cc1Cl)c1ccc[nH]1]

To 1H-pyrrole-2-carboxylic acid (0.3 g, 2.7 mmol) was added in one portion thionyl chloride (10 mL). The mixture was heated at reflux for 2.5 h. The reaction mixture was cooled to ambient temperature and concentrated in vacuo. The residue was dissolved in dichloromethane (5 mL) and placed under a N$_2$ atmosphere. A solution of 2-chloro-4-nitroaniline (0.52 g, 3 mmol) and triethylamine (0.3 g, 3 mmol) in dichloromethane (15 mL) was added dropwise at ambient temperature. The resulting mixture was stirred at ambient temperature for 18 h. To the reaction mixture was added water (50 mL) and dichloromethane (50 mL) and the mixture was stirred at ambient temperature for 15 min. The phases were separated. To the aqueous phase was added water (50 mL) and this was extracted twice with dichloromethane. The combined organic phase was dried over MgSO$_4$, filtered and concentrated to a small volume. Silica gel was added and the mixture was concentrated in vacuo. The residue was transferred to a pre-column and purified by chromatography using a gradient as follows: initially hexanes, then the eluent was modified to 30% hexane in dichloromethane over a 10 min. period, and kept at 30% hexane in dichloromethane for the remainder of the separation. Fractions containing the pure component at R$_f$=0.17 (TLC-silica gel-30% hexane/dichloromethane) were combined and concentrated in vacuo to yield 102 mg of a pale yellow solid. The crude product was dissolved is hot MeOH (75 mL), diluted with water slowly until turbid (~30 mL) and let stand at ambient temperature. The resulting solid was filtered, washed with water and air dried to give 70.2 mg (9.8%) of 3-chloro-N,N-dioxo-4-(1H-pyrrole-2-amido)anilinium as an off-white solid.

MS: m/z 264 (MH$^-$) and m/z 366 (MH$^+$).
$^1$H NMR (500 MHz, DMSO-d$_6$): δ 6.599 (m, 1H), 7.437 (s, 1H), 7.503 (s, 1H), 8.501 (d, 1H), 8.628 (dd, 1H), 8.778 (d, 1H), 9.998 (s, 1H), 12.281 (br s, 1H).

Example 28: 5-Chloro-N-(2-chloro-4-cyanophenyl)-2-hydroxybenzamide

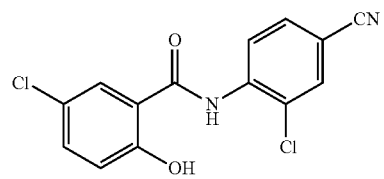 [SMILES: N#Cc1ccc(NC(=O)c2cc(Cl)ccc2O)c(Cl)c1]

To a mixture of 5-chloro-2-hydroxybenzoic acid (0.35 g, 0.002 mol) and 4-amino-3-chlorobenzonitrile (0.31 g, 0.002 mol) in xylenes (10 mL) at ambient temperature was added phosphorous oxychloride (0.068 g, 0.56 mmol) in one portion. The mixture was refluxed for 17.5 h. The mixture was cooled to ambient temperature and the resulting orange solid was filtered and washed several times with hexanes to give 265 mg of crude product. The orange solid was placed in hot acetic acid (45 mL) and an insoluble orange solid (B) was filtered off. The filtrate was allowed to cool to ambient temperature and stand for 3 days. The resulting light orange solid (A) was filtered and washed with hexanes. After air drying both solids, B amounted to 33.8 mg and A amounted to 92.8 mg. Total yield was 126.6 mg (21% yield) of 5-chloro-N-(2-chloro-4-cyanophenyl)-2-hydroxybenzamide. Both solids gave similar MS and NMR results. The following MS and NMR results are for A.

MS: m/z 305 (MH$^-$).
$^1$H NMR (500 MHz, DMSO-d$_6$): δ 7.097 (d, 1H), 7.538 (dd, 1H), 7.884 (dd, 1H), 7.967 (d, 1H), 8.190 (d, 1H), 8.714 (d, 1H), 11.220 (s, 1H), 12.450 (s, 1H).

Example 29: 4-chloro-2-{[2-chloro-(4-methoxycarbonyl)phenyl]carbamoyl}-N,N-dioxoanilinium

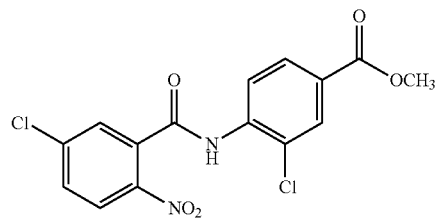 [SMILES: COC(=O)c1ccc(NC(=O)c2cc(Cl)ccc2[N+](=O)[O-])c(Cl)c1]

The compound 4-chloro-2-{[2-chloro-(4-methoxycarbonyl)phenyl]carbamoyl}-N,N-dioxoanilinium was prepared in a similar manner as described in Example 1, Step 3 from 5-chloro-2-nitrobenzoic acid (ACROS) and methyl 4-amino-3-chlorobenzoate to give a 43% yield of 4-chloro-2-{[2-chloro-(4-methoxycarbonyl)phenyl]carbamoyl}-N,N-dioxoanilinium as a tan solid.

MS: m/z 367 (MH$^-$).
$^1$H NMR (500 MHz, DMSO-d$_6$): δ 3.879 (s, 3H), 7.869 (dd, 1H), 7.940 (d, 1H), 8.002 (dd, 1H), 8.036 (d, 1H), 8.099 (d, 1H), 8.236 (d, 1H), 10.636 (s, 1H).

Example 30: Methyl 4-[(5-tert-butyl-2-hydroxybenzene)amido]-3-bromobenzoate

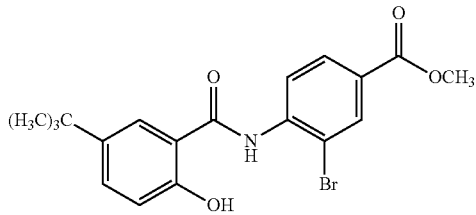 [SMILES: COC(=O)c1ccc(NC(=O)c2cc(C(C)(C)C)ccc2O)c(Br)c1]

Methyl 4-[(5-tert-butyl-2-hydroxybenzene)amido]-3-bromobenzoate was prepared in a similar manner as described in Example 1, step 3 using 5-tert-butyl-2-hydroxybenzoic acid [prepared as described in WO2005110996A1] in place of 2-hydroxy-5-(trifluoromethyl)benzoic acid and methyl 4-amino-3-bromobenzoate (Acros Organics) in place of methyl 4-amino-3-chlorobenzoate to obtain methyl 4-[(5-tert-butyl-2-hydroxybenzene)amido]-3-bromobenzoate as a white solid. This product was obtained in three fractions. Fraction A was obtained by filtering a precipitate that formed in several of the fractions from the original chromatography (using a gradient as follows: initially hexane, then the eluent was modified to 20% EtOAc/hexanes over a 17 min. period) to yield the product in 33.5%. The filtrate from Fraction A and the remaining fractions containing slightly impure product were combined and concentrated in vacuo and re-chromatographed using a gradient as follows: initially hexane, then the eluent was modified to 70% dichloromethane/hexane over a 5 min. period to give 4.8% yield of product as Fraction C. The impure fractions from Fraction C were concentrated in vacuo and recrystallized from EtOAc/hexanes mixtures to give 8.5% of product as Fraction D. The total yield was 46.8%. The data below is for Fraction A. The LC/MS data for Fractions C and D were identical with Fraction A.

MS: m/z 404 (MH$^-$) and m/z 406 (MH$^+$).

$^1$H NMR (500 MHz, DMSO-d$_6$): δ 1.280 (s, 9H), 3.857 (s, 3H), 7.004 (d, 1H), 7.522 (dd, 1H), 7.990 (dd, 1H), 8.038 (d, 1H), 8.189 (d, 1H), 8.657 (d, 1H), 11.094 (s, 1H), 11.793 (s, 1H).

Example 31: 4-[(5-tert-butyl-2-hydroxybenzene)amido]-3-bromobenzoic acid

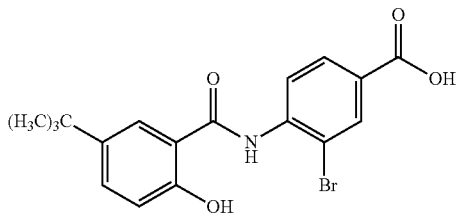 [SMILES: CC(C)(C)c1ccc(O)c(C(=O)Nc2ccc(C(=O)O)cc2Br)c1]

The compound 4-[(5-tert-butyl-2-hydroxybenzene)amido]-3-bromobenzoic acid was prepared in a similar manner as described in Example 2 substituting methyl 4-[(5-tert-butyl-2-hydroxybenzene)amido]-3-bromobenzoate [Example 30] for methyl 3-chloro-4-{[2-hydroxy-5-(trifluoromethyl)benzene]amido}benzoate to give 4-[(5-tert-butyl-2-hydroxybenzene)amido]-3-bromobenzoic acid as a white solid in a quantitative yield.

MS: m/z 390 (MH$^-$) and m/z 392 (MH$^+$).

$^1$H NMR (500 MHz, DMSO-d$_6$): δ 1.346 (s, 9H), 7.066 (d, 1H), 7.580 (dd, 1H), 8.029 (dd, 1H), 8.104 (d, 1H), 8.228 (d, 1H), 8.683 (d, 1H), 11.175 (s, 1H), 11.953 (br s, 1H), 13.150 (hr s, 1H).

Example 32: Methyl 4-[(5-isopropyl-2-hydroxybenzene)amido]-3-chlorobenzoate

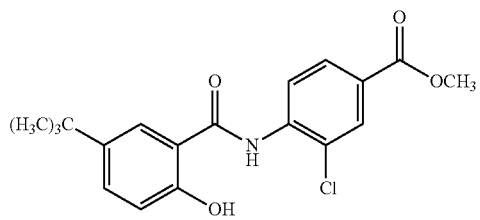

Methyl 4-[(5-isopropyl-2-hydroxybenzene)amido]-3-chlorobenzoate was prepared in a similar manner as described in Example 1, step 3 using 5-isopropyl-2-hydroxybenzoic acid [prepared as described for 2-hydroxy-5-(trifluoromethyl)benzoic acid in Example 1, steps 1 and 2 substituting 4-isopropylphenol for 4-(trifluoromethyl)phenol] in place of 2-hydroxy-5-(trifluoromethyl)benzoic acid to obtain methyl 4-[(5-isopropyl-2-hydroxybenzene)amido]-3-chlorobenzoate as a white solid. Before chromatography, this material was dissolved in EtOAc and washed with saturated NaHCO$_3$ aq., 1 N HCl aq., brine and then dried over sodium sulfate. The product was obtained in two fractions. Fraction A was obtained by recrystallization of the solid obtained from chromatography (using a gradient as follows: initially hexane, then the eluent was modified to 20% EtOAc/hexanes over a 17 min. period) from xylenes to give a 25.7% yield of the title compound. Fraction B was obtained by filtration of the solid formed in the filtrate from Fraction A plus hexanes washes to give a 3.8% yield of the title compound. The total yield was 29.5%. The data given below is for Fraction A. The LC/MS for Fraction B was identical to that of Fraction A.

MS: m/z 346.1 (MH$^-$) and m/z 348.1 (MH$^+$).

$^1$H NMR (500 MHz, DMSO-d$_6$): δ 1.193 (d, 6H), 3.856 (s, 3H), 6.992 (d, 1H), 7.362 (dd, 1H), 7.893 (d, 1H), 7.916 (dd, 1H), 8.039 (d, 1H), 8.713 (d, 1H), 11.228 (s, 1H), 11.803 (s, 1H).

Example 33: 4-[(5-isopropyl-2-hydroxybenzene)amido]-3-chlorobenzoic acid

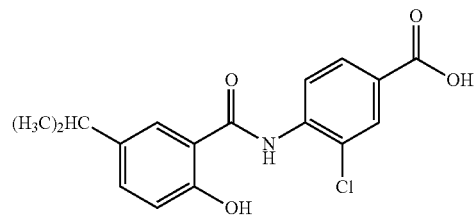

The compound 4-[(5-isopropyl-2-hydroxybenzene)amido]-3-chlorobenzoic acid was prepared in a similar manner as described in Example 2 substituting methyl 4-[(5-isopropyl-2-hydroxybenzene)amido]-3-chlorobenzoate [Example 32] for methyl 3-chloro-4-{[2-hydroxy-5-(trifluoromethyl)benzene]amido}benzoate to give 4-[(5-isopropyl-2-hydroxybenzene)amido]-3-chlorobenzoic acid as a white solid in a quantitative yield.

MS: m/z 332.1 (MH$^-$) and m/z 334 (MH$^+$).

$^1$H NMR (500 MHz, DMSO-d$_6$): δ 1.193 (d, 6H), 6.990 (d, 1H), 7.359 (dd, 1H), 7.895 (d, 1H), 7.938 (dd, 1H), 8.010 (d, 1H), 8.678 (d, 1H), 11.201 (s, 1H), 11.792 (br s, 1H), 13.116 (br s, 1H).

Example 34: Methyl 3-chloro-4-[(2-hydroxy-5-iodobenzene)amido]benzoate

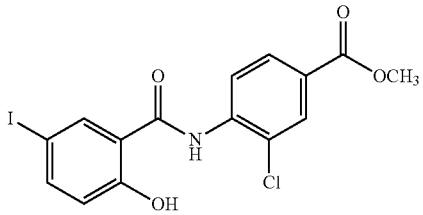 [SMILES: COC(=O)c1ccc(NC(=O)c2cc(I)ccc2O)c(Cl)c1]

Methyl 3-chloro-4-[(2-hydroxy-5-iodobenzene)amido]benzoate was prepared in a similar manner as described in Example 1, step 3 using 2-hydroxy-5-iodobenzoic acid [ACROS Chemicals] in place of 2-hydroxy-5-(trifluoromethyl)benzoic acid to obtain methyl 4-[(2-hydroxy-5-iodobenzene)amido]-3-chlorobenzoate as a white solid. The product was obtained in two fractions. Fraction A was obtained by chromatography (30% EtOAc/hexanes) to give a 36.6% yield of the title compound (minor impurities-will use without further purification). Fraction. B also from the chromatography generated a 25.3% yield of the title compound (very, very minor impurities). The total yield was 61.9%. The data given below is for Fraction B. The LC/MS and NMR for Fraction A was identical to that of Fraction B, however the NMR showed more of the minor impurities. The LC/MS of both fractions showed them to be 100% pure.

MS: m/z 429.9 (MH$^-$).

$^1$H NMR (500 MHz, DMSO-d$_6$): δ 3.925 (s, 3H), 6.969 (d, 1H), 7.827 (dd, 1H), 8.041 (dm, 1H), 8.110 (m, 1H), 8.334 (d, 1H), 8.738 (d, 1H), 11.204 (s, 1H), 12.437 (s, 1H).

Example 35: 3-Chloro-4-[(2-hydroxy-5-iodobenzene)amido]benzoic acid

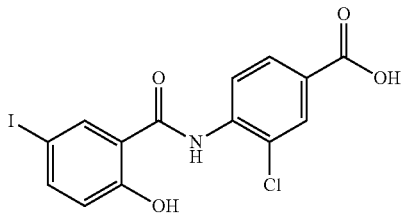 [SMILES: O=C(O)c1ccc(NC(=O)c2cc(I)ccc2O)c(Cl)c1]

The compound 3-chloro-4-[(2-hydroxy-5-iodobenzene)amido]benzoic acid was prepared in a similar manner as described in Example 2 substituting methyl 4-[(2-hydroxy-5-iodobenzene)amido]-3-chlorobenzoate [Example 34] for methyl 3-chloro-4-{[2-hydroxy-5-(trifluoromethyl)benzene]-amido}benzoate to give 4-[(2-hydroxy-5-iodobenzene)amido]-3-chlorobenzoic acid as a white solid in a 87% yield.

MS: m/z 415.9 (MH$^-$) and m/z 417.9 (MH$^+$).

$^1$H NMR (500 MHz, DMSO-d$_6$): δ 6.968 (d, 1H), 7.826 (dd, 1H), 8.015 (dd, 1H), 8.083 (d, 1H), 8.339 (d, 1H), 8.705 (d, 1H), 11.187 (s, 1H), 12.424 (br s, 1H), 13.210 (br s, 1H),

Example 36: Methyl 3-chloro-4-(2-hydroxypyridine-3-amido)benzoate

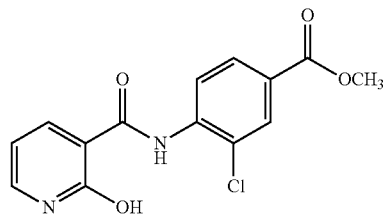 [SMILES: COC(=O)c1ccc(NC(=O)c2cccnc2O)c(Cl)c1]

To a solution of methyl 4-amino-3-chlorobenzoate (0.37 g, 0.002 mol) and diisopropylethylamine (0.39 g, 0.003 mole) in dioxane at ambient temperature was added in one portion 2-oxo-1,2-dihydro-3-pyridinecarbonyl chloride (0.4 g, 0.002 mol) [prepared as described in WO/2011/088201 A1]. The mixture was heated at reflux for 24 h. after which it was cooled to ambient temperature and partitioned between EtOAc and water. The two phase material was filtered and the solid was washed with water, then EtOAc and air dried to obtain a 25% yield of the title compound as an off-white solid.

MS: m/z 305 (MH$^-$) and m/z 307 (MH$^+$).

$^1$H NMR (500 MHz, DMSO-d$_6$): δ 3.848 (s, 3H), 6.604 (t, 1H), 7.878 (qd, 1H), 7.942 (dd, 1H), 8.015 (d, 1H), 8.504 (dd, 1H), 8.744 (d, 1H), 12.787 (br s, 1H), 12.893 (s, 1H).

Example 37: 3-Chloro-4-(2-hydroxypyridine-3-amido)benzoic acid

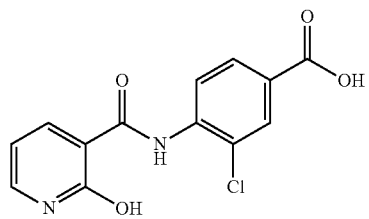 [SMILES: O=C(O)c1ccc(NC(=O)c2cccnc2O)c(Cl)c1]

To a suspension of methyl 3-chloro-4-(2-hydroxypyridine-3-amido)benzoate [Example 36] (0.077 g, 0.25 mmol) in ethanol (2.9 mL) at ambient temperature was added 1M NaOH aq. (2.9 mL, 2.9 mmol) in one portion and the mixture was stirred at ambient temperature for 3 h. The pH of the reaction mixture was adjusted to ~2 by addition of 1N HCl aq. and the mixture was concentrated in vacuo to remove the ethanol. The aqueous residue was partitioned between a mixture of EtOAc/dichloromethane and water.

The two phase material was filtered and the solid was washed several times with water and air dried to give a 42.5% yield of the title compound as an off-white solid. This was labeled component A.

The two phase filtrate was separated and the organic phase was washed with water, then brine and dried over sodium sulfate. The mixture was filtered and concentrated in vacuo to give a 47.8% yield of the title compound as a white solid. This was labeled component B. The LC/MS and NMR were identical to component A. The data given below is for component A.

MS: m/z 291 (MH$^-$) and m/z 293 (MH$^+$).

$^1$H NMR (500 MHz, DMSO-d$_6$): δ 6.601 (t, 1H), 7.874 (br m, 1H), 7.915 (dd, 1H), 7.986 (d, 1H), 8.505 (dd, 1H), 8.716 (d, 1H), 12.780 (br s, 1H), 12.855 (s, 1H), 13.084 (br s, 1H).

Example 38: Methyl 4-[(5-tert-butyl-2-hydroxybenzene)amido]benzoate

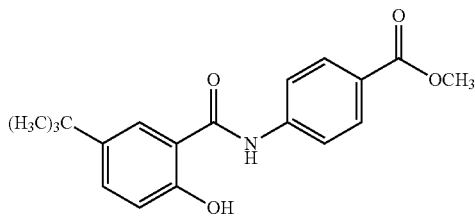 [SMILES: COC(=O)c1ccc(NC(=O)c2cc(C(C)(C)C)ccc2O)cc1]

Methyl 4-[(5-tert-butyl-2-hydroxybenzene)amido]benzoate was prepared in a similar manner as described in Example 1, Step 3 using 5-tert-butyl-2-hydroxybenzoic acid [prepared as described in WO2005110996A1] in place of 2-hydroxy-5-(trifluoromethyl)benzoic acid and methyl 4-aminobenzoate [Alfa Aesar] in place of methyl 4-amino-3-chlorobenzoate to give a 60% yield of methyl 4-[(5-tert-butyl-2-hydroxybenzene)amido]benzoate as a white solid.

MS: m/z 326.1 (MH$^-$) and m/z 328.2 (MH$^+$).

$^1$H NMR (500 MHz, DMSO-d$_6$): δ 1.285 (2, 9H), 3.838 (s, 3H), 6.938 (d, 1H), 7.474 (dd, 1H), 7.846 (s, 1H), 7.850 (s, 1H), 7.864 (m, 1H), 7.958 (m, 1H), 7.976 (m, 1H), 10.603 (s, 1H), 11.291 (s, 1H).

Example 39: 4-[(5-tert-butyl-2-hydroxybenzene)amido]benzoic acid

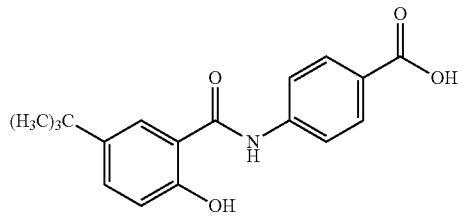 [SMILES: CC(C)(C)c1ccc(O)c(C(=O)Nc2ccc(C(=O)O)cc2)c1]

The compound 4-[(5-tert-butyl-2-hydroxybenzene)amido]benzoic acid was prepared in a similar manner as described in Example 2 substituting methyl 4-[(5-tert-butyl-2-hydroxybenzene)amido]benzoate [Example 38] for methyl 4-{[2-hydroxy-5-(trifluoromethyl) benzene]amido}benzoate to give 4-[(5-tert-butyl-2-hydroxybenzene)amido]benzoic acid as a white solid in a quantitative yield.

MS: m/z 312.1 (MH$^-$) and m/z 314.1 (MH$^+$).

$^1$H NMR (500 MHz, DMSO-d$_6$): δ 1.287 (s, 9H), 6.936 (d, 1H), 7.473 (dd, 1H), 7.814 (m, 1H), 7.832 (m, 1H), 7.858 (d, 1H), 7.933 (m, 1H), 7.951 (m, 1H), 10.583 (s, 1H), 11.325 (br s, 1H), 12.758 (br s, 1H).

Example 40: Methyl 4-[(5-tert-butyl-2-hydroxybenzene)amido]-3-iodobenzoate

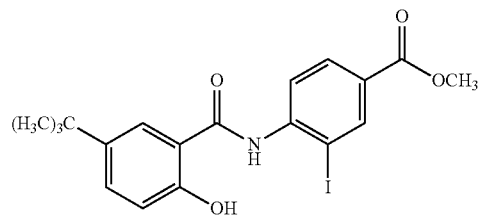 [SMILES: COC(=O)c1ccc(NC(=O)c2cc(C(C)(C)C)ccc2O)c(I)c1]

Methyl 4-[(5-tert-butyl-2-hydroxybenzene)amido]-3-iodobenzoate was prepared in a similar manner as described in WO/2010/101648A1 from 5-tert-butyl-2-hydroxybenzoic acid [prepared as described in WO2005110996A1] and methyl 4-amino-3-iodobenzoate [ACROS Chemicals] except the xylenes solution was chilled in an ice bath and vigorously stirred before the product was filtered to give a 33% yield of methyl 4-[(5-tert-butyl-2-hydroxybenzene)amido]-3-iodobenzoate as an off-white solid.

MS: m/z, 452 (MH$^-$) and m/z 454 (MH$^+$).

$^1$H NMR (500 MHz, DMSO-d$_6$): δ 1.280 (s, 9H), 3.850 (s, 3H), 7.006 (d, 1H), 7.517 (dd, 1H), 7.989 (dd, 1H), 8.028 (d, 1H), 8.408 (d, 1H), 8.419 (d, 1H), 10.764 (s, 1H), 11.775 (s, 1H).

Example 41: 4-[(5-tert-butyl-2-hydroxybenzene)amido]-3-iodobenzoic acid

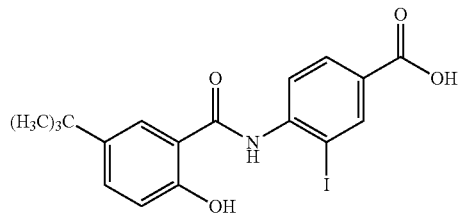

The compound 4-[(5-tert-butyl-2-hydroxybenzene)amido]-3-iodobenzoic acid was prepared in a similar manner as described in Example 2 substituting methyl 4-[(5-tert-butyl-2-hydroxybenzene)amido]-3-iodobenzoate [Example 40] for methyl 3-chloro-4-{[2-hydroxy-5-(trifluoromethyl)-benzene]amido}benzoate to give 4-[(5-tert-butyl-2-hydroxybenzene)amido]-3-iodobenzoic acid as an off-white white solid in a 80% yield.

MS: m/z 438 (MH$^-$) and m/z 440 (MH$^+$).

$^1$H NMR (500 MHz, DMSO-d$_6$): δ 1.348 (s, 9H), 7.068 (d, 1H), 7.580 (dd, 1H), 8.028 (dd, 1H), 8.091 (d, 1H), 8.433 (d, 1H), 8.463 (d, 1H), 10.807 (s, 1H), 11.836 (br s, 1H), 13.040 (br s, 1H).

Example 42: Methyl 4-[(5-tert-butyl-2-hydroxyben-zene)amido]-3-methoxybenzoate

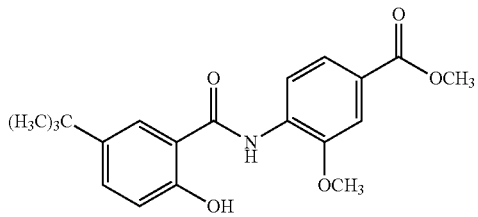 [SMILES: COC(=O)c1ccc(NC(=O)c2cc(C(C)(C)C)ccc2O)c(OC)c1]

Step 1: Methyl 4-amino-3-methoxybenzoate

This procedure was adopted from a procedure reported in J. Med. Chem., 54, 7815-7833 (2011). Thionyl chloride (1.78 g, 0.015 mal) was added dropwise to methanol (8 mL) at 0° C. over a 25 min. period keeping the temperature at or below 0.7° C. The resulting mixture was stirred at 0° C. for 1 hr., then 4-amino-3-methoxybenzoic acid (0.5 g, 0.003 mol) [ACROS Chemicals] was added in one portion. The reaction mixture was stirred at ambient temperature for 3 days after which the mixture was concentrated in vacuo. Water (5 mL) was added to the residue and sodium bicarbonate (0.3 g, 3.6 mmol) was added in one portion and the mixture was stirred at ambient temperature for 30 min. The mixture was extracted several times with ethyl acetate. The combined organic phase was dried over sodium sulfate, filtered and concentrated in vacuo to give 0.5 g (92%) of methyl 4-amino-3-methoxybenzoate as a brown solid.

MS: m/z 182.1 (MH$^+$).

$^1$H NMR (500 MHz, DMSO-d$_6$): δ 3.741 (s, 3H), 3.797 (s, 3H), 5.608 (s, 2H), 6.630 (d, 1H), 7.281 (d, 1H), 7.375 (dd, 1H).

Step 2: Methyl 4-[(5-tert-butyl-2-hydroxybenzene)amido]-3-methoxybenzoate

This compound was prepared in a similar manner as described in Example 1, Step 3 from 5-tert-butyl-2-hydroxybenzoic acid [prepared as described in WO2005110996A1] and methyl 4-amino-3-methoxybenzoate (step 1) to obtain methyl 4-[(5-tert-butyl-2-hydroxybenzene)amido]-3-methoxybenzoate as a light tan solid. Before chromatography, the cooled reaction mixture was dissolved in ethyl acetate and washed with saturated sodium bicarbonate (aq.), 1N hydrogen chloride (aq.), brine and dried over sodium sulfate. The preabsorbed (on silica gel) material was divided into 2 parts. For part one, the material was purified by chromatography using a gradient as follows: initially hexane for 1 min., then the eluent was modified to 15% ethyl acetate/hexane over a 13.5 min. period, then kept at 15% ethyl acetate/hexane for 8.5 min., then the eluent was modified to 30% ethyl acetate/hexane over a 1 min. period and kept at 30% ethyl acetate/hexane for the remainder of the separation. For part two, the following gradient was used: initially hexane for 1 min., then the eluent was modified to 20% ethyl acetate/hexane over a 12 min. period, kept at 20% ethyl acetate/hexane for 4 min., then modified to 30% ethyl acetate/hexane over a 2 min. period and kept at 30% ethyl acetate/hexanes for the remainder of the separation. The fractions containing pure product from both chromatographic runs were combined and concentrated in vacuo to give (68% yield) of a light tan solid.

MS: m/z 356.1 (MH$^-$) and m/z 358.1 (MH$^+$).

$^1$H NMR (500 MHz, DMSO-d$_6$): δ 1.275 (s, 9H), 3.847 (s, 3H), 3.968 (s, 3H), 6.981 (d, 1H), 7.481 (dd, 1H), 7.565 (d, 1H), 7.638 (dd, 1H), 8.032 (d, 1H), 8.620 (d, 1H), 11.146 (s, 1H), 11.537 (s, 1H).

Example 43: 4-[(5-tert-butyl-2-hydroxybenzene)amido]-3-methoxybenzoic acid

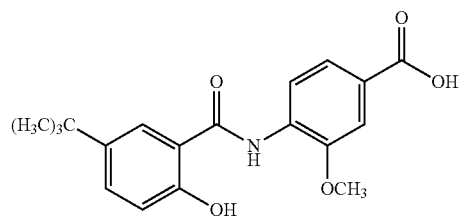 [SMILES: COc1cc(C(=O)O)ccc1NC(=O)c1cc(C(C)(C)C)ccc1O]

The compound 4-[(5-tert-butyl-2-hydroxybenzene)amido]-3-methoxybenzoic acid was prepared in a similar manner as described in Example 2 substituting methyl 4-[(5-tert-butyl-2-hydroxy)amido]-3-methoxybenzoate [Example 42] for methyl 3-chloro-4-{[2-hydroxy-5-(trifluoromethyl)benzene]amido}benzoate to give 4-[(5-tert-butyl-2-hydroxybenzene)amido]-3-methoxybenzoic acid as an off-white to white solid in a quantitative yield.

MS: m/z 342.1 (MW) and m/z 344.1 (MH$^+$).

$^1$H NMR (500 MHz, DMSO-d$_6$): δ 1.283 (s, 9H), 3.964 (s, 3H), 6.985 (d, 1H), 7.485 (dd, 1H), 7.566 (d, 1H), 7.616 (dd, 1H), 8.040 (d, 1H), 8.595 (d, 1H), 11.127 (s, 1H), 11.532 (s, 1H), 12.800 (br s, 1H).

Example 44: Methyl 4-[(5-tert-butyl-2-hydroxybenzene)amido]-3-(trifluoromethyl)benzoate

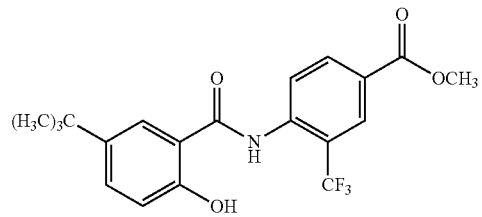

Step 1: Methyl 4-amino-3-(trifluoromethyl)benzoate

Thionyl chloride (1.43 g, 0.012 mol) was added dropwise to methanol (8 mL) chilled to −0.6° C. at a rate that did not allow the temperature to exceed 0.7° C. The resulting mixture was stirred at 0° C. for 45 min., then 4-amino-3-(trifluoromethyl)benzoic acid (0.5 g, 0.0024 mol) [Matrix Scientific] was added in one portion. The reaction mixture was stirred at 0° C. for one hr., allowed to come to ambient temperature and was stirred for 3 days. The mixture was concentrated in vacuo. Water (10 mL) was added to the residue and sodium bicarbonate (0.3 g, 3.6 mmol) was added in one portion and the mixture was stirred at ambient temperature for 45 min. The mixture was extracted several times with ethyl acetate. The combined organic phase was dried over sodium sulfate, filtered and concentrated in vacuo to give 0.49 g (93%) of methyl 4-amino-3-(trifluoromethyl) benzoate as a pinkish-tan colored solid.

MS: m/z 220.1 (MH⁺).

¹H NMR (500 MHz, DMSO-d₆): δ 3.762 (s, 3H), 6.469 (s, 2H), 6.847 (d, 1H), 7.803 (dd, 1H), 7.882 (d, 1H).

Step 2: Methyl 4-[(5-tert-butyl-2-hydroxybenzene) amido]-3-(trifluoromethyl)benzoate This compound was prepared in a similar manner as described in Example 1, step 3 from 5-tert-butyl-2-hydroxybenzoic acid [prepared as described in WO2005110996A1] and methyl 4-amino-3-methoxybenzoate (step 1) to obtain methyl 4-[(5-tert-butyl-2-hydroxybenzene)amido]-3(trifluoromethyl)benzoate as a light tan solid. Before chromatography, the cooled reaction mixture was dissolved in ethyl acetate and washed with 1N hydrogen chloride (aq.), saturated sodium bicarbonate (aq.), brine and dried over sodium sulfate. The preabsorbed (on silica gel) material was purified by chromatography using a gradient as follows: initially hexane for 1 min., then the eluent was modified to 10% ethyl acetate/hexane over a 19 min. period and kept at 10% ethyl acetate/hexane for the remainder of the separation. The fractions containing pure product were combined and concentrated in vacuo to give 0.163 g (27.5% yield) of a white solid.

MS: m/z 394.1 (MH⁻) and m/z 396.1 (MH⁺).

¹H NMR (500 MHz, DMSO-d₆): δ 1.286 (s, 9H), 3.898 (s, 3H), 7.000 (d, 1H), 7.538 (dd, 1H), 8.045 (d, 1H), 8.221 (d, 1H), 8.268 (dd, 1H), 8.647 (d, 1H), 11.154 (s, 1H), 11.825 (s, 1H).

Example 45: 4-[(5-tert-butyl-2-hydroxybenzene) amido]-3-(trifluoromethyl)benzoic acid

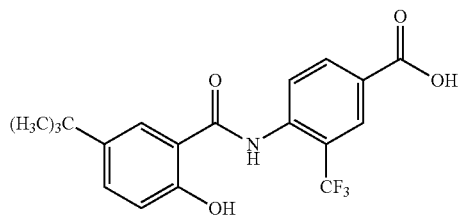

The compound 4-[(5-tert-butyl-2-hydroxybenzene) amido]-3-(trifluoromethyl)benzoic acid was prepared in a similar manner as described in Example 2 substituting methyl 4-[(5-tert-butyl-2-hydroxybenzene)amido]-3-(trifluoromethyl)benzoate [Example 44] for methyl 3-chloro-4-{[2-hydroxy-5-(trifluoromethyl)benzene]-amido}benzoate to give 4-[(5-tert-butyl-2-hydroxybenzene)amido]-3-(trifluoromethyl)benzoic acid as a white solid in a 95.8% yield.

MS: m/z 380.1 (MH⁻) and m/z 382.1 (MH⁺).

¹H NMR (500 MHz, DMSO-d₆): δ 1.344 (s, 9H), 7.056 (d, 1H), 7.593 (dd, 1H), 8.103 (d, 1H), 8.270 (d, 1H), 8.298 (dd, 1H), 8.655 (d, 1H), 11.180 (s, 1H), 11.866 (br s, 1H), 13.386 (br s, 1H).

Example 46: Methyl 4-[(5-sec-butyl-2-hydroxybenzene)amido]-3-chlorobenzoate

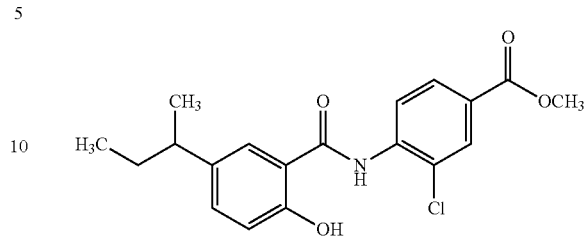

Step 1: 5-sec-Butyl-2-hydroxybenzaldehyde

This compound was prepared in a similar manner as described in Example 1, step 1 by substituting 4-sec-butylphenol [TCI America] for 4-(trifluoromethyl)phenol except hexane was used as the eluent for column chromatography to give a 85% yield of 5-sec-butyl-2-hydroxybenzaldehyde as a very pale yellow oil.

MS: m/z 179.1 (MH⁺) and m/z 177.1 (MH⁻).

¹H NMR (500 MHz, DMSO-d₆): δ 0.743 (t, 3H), 1.149 (d, 3H), 1.510 (m, 2H), 2.557 (m, 1H), 6.924 (d, 1H), 7.367 (dd, 1H), 7.455 (d, 1H), 10.220 (s, 1H), 10.489 (s, 1H).

Step 2: 5-sec-Butyl-2-hydroxybenzoic acid

This compound was prepared in a similar manner as described in Example 1, step 2 substituting 5-sec-butyl-2-hydroxybenzaldhyde (Example 46, step 1) for 2-hydroxy-5-(trifluoromethyl)benzaldehyde to give 5-sec-butyl-2-hydroxybenzoic acid as an orangish-yellow semi-solid.

MS: m/z 195.1 (MH⁻) and m/z 193.1 (MH⁻).

¹H NMR (500 MHz, DMSO-d₆): δ 0.734 (t, 3H), 1.139 (d, 3H), 1.496 (m, 2H), 2.540 (m, 1H), 6.853 (d, 1H), 7.325 (dd, 1H), 7.562 (d, 1H), 10.220 (s, 1H), 12.400 (br s, 1H). NMR indicated the presence of a small amount of the aldehyde and other minor impurities. This material was used without further purification.

Step 3: Methyl 4-[(5-sec-butyl-2-hydroxybenzene) amido]-3-chlorobenzoate

This compound was prepared in a similar manner as described in Example 1, step 3 from 5-sec-butyl-2-hydroxybenzoic acid (Example 46, steps 1 and 2) [prepared as described in WO2005110996A1] and methyl 4-amino-3-chlorobenzoate to obtain methyl 4-[(5-sec-butyl-2-hydroxybenzene)amido]-3-chlorobenzoate as a white solid. Before chromatography, the cooled reaction mixture was dissolved in ethyl acetate and washed with 1N hydrogen chloride (aq.), saturated sodium bicarbonate (aq.), brine and dried over sodium sulfate. The preabsorbed (on silica gel) material was purified by chromatography using a gradient as follows: initially hexane for 1 min., then the eluent was modified to 10% ethyl acetate/hexane over a 14 min. period and kept at 10% ethyl acetate/hexane for the remainder of the separation. The fractions containing pure product were combined and concentrated in vacuo to give a 59.8% yield of a tan solid. This solid was recrystallized from MeOH/water to give a 39.5% yield of methyl 4-[(5-sec-butyl-2-hydroxy) benzeneamido]-3-chlorobenzoate as a white solid.

MS: m/z 360.1 (MH⁻) and m/z 362.1 (MH⁺).

¹H NMR (500 MHz, DMSO-d₆): δ 0.759 (t, 3H), 1.173 (d, 3H), 1.530 (m, 2H), 2.591 (m, 1H), 3.853 (s, 3H), 6.992 (d, 1H), 7.312 (dd, 1H), 7.844 (d, 1H), 7.962 (dd, 1H), 8.036 (d, 1H), 8.706 (d, 1H), 11.225 (s, 1H), 11.794 (s, 1H).

Example 47: 4-[(5-sec-butyl-2-hydroxybenzene)amido]-3-chlorobenzoic acid

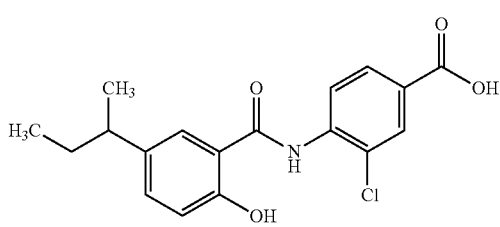 [SMILES: CCC(C)c1ccc(O)c(C(=O)Nc2ccc(C(=O)O)cc2Cl)c1]

The compound 4-[(5-sec-butyl-2-hydroxybenzene)amido]-3-chlorobenzoic acid was prepared in a similar manner as described in Example 2 substituting methyl 4-[(5-sec-butyl-2-hydroxybenzene)amido]-3-chlorobenzoate [Example 46] for methyl 3-chloro-4-{[2-hydroxy-5-(trifluoromethyl)benzene]-amido}benzoate to give 4-[(5-sec-butyl-2-hydroxybenzene)amido]-3-chlorobenzoic acid as a white solid in a 95.7% yield.

MS: m/z 346 (MH⁻) and m/z 348.1 (MH⁺).

¹H NMR (500 MHz, DMSO-d₆): δ 0.756 (t, 3H), 1.171 (d, 3H), 1.529 (m, 2H), 2.589 (m, 1H), 6.987 (d, 1H), 7.307 (dd, 1H), 7.844 (d, 1H), 7.933 (dd, 1H), 8.005 (d, 1H), 8.671 (d, 1H), 11.205 (s, 1H), 11.803 (br s, 1H), 13.116 (br s, 1H).

Example 48: 5-tert-Butyl-N-[2-chloro-4-(trifluoromethyl)phenyl]-2-hydroxybenzamide

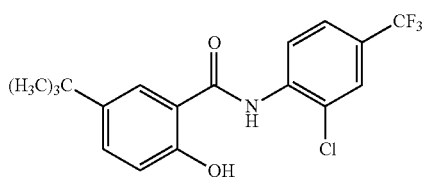 [SMILES: CC(C)(C)c1ccc(O)c(C(=O)Nc2ccc(C(F)(F)F)cc2Cl)c1]

The compound 5-tert-butyl-N-[2-chloro-4-(trifluoromethyl)phenyl]-2-hydroxybenzamide was prepared in a similar manner as described in Example 1, step 3 from 5-tert-butyl-2-hydroxybenzoic acid [prepared as described in WO2005110996A1] and 4-amino-3-chlorobenzotrifluoride [ACROS Chemicals] to obtain 5-tert-butyl-N-[2-chloro-4-(trifluoromethyl)phenyl]-2-hydroxybenzamide as a white solid. Before chromatography, the cooled reaction mixture was dissolved in ethyl acetate, silica gel was added and the mixture was concentrated in vacuo. The residue was transferred to a pre-column and purified by chromatography using a gradient as follows: initially hexane (1 min.), then the eluent was modified to 10% ethyl acetate/hexane over a 19 min. period and kept at 10% ethyl acetate/hexane for the remainder of the purification. The fractions containing the pure major component were combined and concentrated in vacuo to give a 61.5% yield of 5-tert-butyl-N-[2-chloro-4-(trifluoromethyl)phenyl]-2-hydroxybenzamide as a white solid.

MS: m/z 370 (MH⁻) and m/z 372.1 (MH⁺).

¹H NMR (500 MHz, DMSO-d₆): δ 1,275 (s, 9H), 6.998 (d, 1H), 7.522 (dd, 1H), 7.770 (br dd, 1H), 7.969 (br d, 1H), 8.036 (d, 1H), 8.755 (d, 1H), 11.208 (s, 1H), 11.818 (s, 1H).

Example 49: Isopropyl 4-[(5-tert-butyl-2-hydroxybenzene)amido]-3-chlorobenzoate

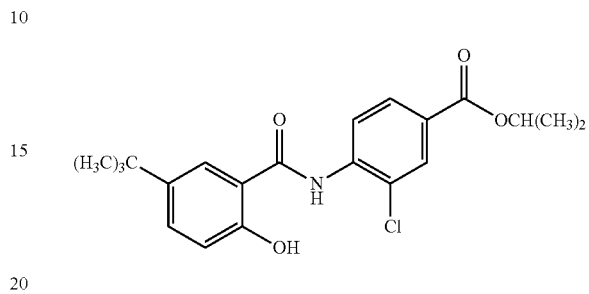

Step 1: Isopropyl 4-amino-3-chlorobenzoate

This compound was prepared as described in PCT Int. Appl., 2010116270 (14 Oct. 2010) with minor modifications. Thionyl chloride (5.7 g, 0.048 mol) was added dropwise to a solution of 4-amino-3-chlorobenzoic acid (1.0 g, 0.006 mol) in isopropanol (35 mL) at 0° C. The resulting mixture was stirred at 0° C. for 15 min., then allowed to come to ambient temperature and stirred for 2 days. The mixture was then heated at reflux for 21 hr. After cooling to ambient temperature, saturated aqueous sodium bicarbonate solution (~40 mL) was added carefully until a pH of 7 was obtained. The mixture was extracted several times with ethyl acetate. The combined organic phase was washed with saturated aqueous sodium bicarbonate, water and brine. The organic phase was dried over sodium sulfate, filtered and concentrated in vacuo to give 1.23 g (96%) of isopropyl 4-amino-3-chlorobenzoate as a pinkish-tan colored solid.

MS: m/z 214.1 (MH⁺).

¹H NMR (500 MHz, DMSO-d₆): δ 1.257 (d, 6H), 5.030 (m, 1H), 6.185 (s, 2H), 6.784 (d, 1H), 7.582 (dd, 1H), 7.693 (d, 1H).

Step 2: Isopropyl 4-[(5-tert-butyl-2-hydroxybenzene)amido]-3-chlorobenzoate

This compound was prepared in a similar manner as described in Example 1, step 3 from 5-tert-butyl-2-hydroxybenzoic acid [prepared as described in WO2005110996A1] and isopropyl 4-amino-3-chlorobenzoate (step 1) to obtain isopropyl 4-[(5-tert-butyl-2-hydroxybenzene)amido]-3-chlorobenzoate as a white solid. Before chromatography, the cooled reaction mixture was dissolved in ethyl acetate and washed with saturated sodium bicarbonate (aq.), 1N hydrogen chloride (aq.), brine and dried over sodium sulfate. The preabsorbed (on silica gel) material was purified by chromatography using a gradient as follows: initially hexane for 1 min., then the eluent was modified to 20% ethyl acetate/hexane over a 24 min. period, and kept at 20% ethyl acetate/hexane for the remainder of the separation. The fractions containing pure product were combined and concentrated in vacuo to give a 46.5% yield of isopropyl 4-[(5-tert-butyl-2-hydroxybenzene)amido]-3-chlorobenzoate as a white solid.

MS: m/z 388.1 (MH⁻) and m/z 390.2 (MH⁺).

¹H NMR (500 MHz, DMSO-d₆): δ 1.289 (s, 9H), 1.334 (d, 6H), 5.139 (m, 1H), 7.012 (d, 1H), 7.533 (dd, 1H), 7.953 (dd, 1H), 8.039 (dd, 1H), 8.720 (d, 1H), 11.229 (s, 1H), 11.821 (s, 1H).

Example 50: 4-{[2-(Acetyloxy)-5-chlorobenzene]amido}-3-chlorobenzoic acid

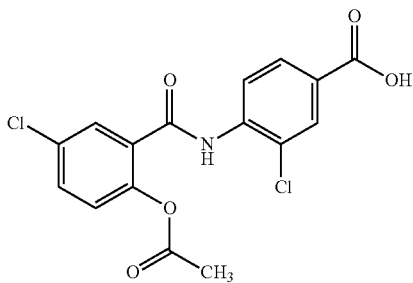 [SMILES: CC(=O)Oc1ccc(Cl)cc1C(=O)Nc1ccc(C(=O)O)cc1Cl]

3-chloro-4-[(5-chloro-2-hydroxy benzene)amido]benzoic acid (Example 6) [0.5 g, 0.0015 mol] was suspended in acetic anhydride (4.5 mL) at ambient temperature. Concentrated sulfuric acid (1 μL) was added and the mixture was stirred at ambient temperature for 24 hr. The reaction mixture was poured into an ice/water mixture (150 mL) and the mixture was stirred at ambient temperature until all of the ice had melted. The resulting solid was filtered and washed several times with water and air dried. The crude product was dissolved in ethyl acetate, silica gel was added and the mixture was concentrated in vacuo. The residue was transferred to a pre-column and purified by chromatography using a gradient as follows: initially hexane (1 min.), then the eluent was modified to 30% ethyl acetate/hexane over a 14 min. period, then kept at 30% ethyl acetate/hexane for 10 min., then the eluent was modified to 50% ethyl acetate/hexane over a 4 min. period and kept at 50% ethyl acetate/hexane for the remainder of the separation. The fractions containing the pure major component were combined and concentrated in vacuo to give a 0.255 g (46.3%) yield of 4-{[2-(acetyloxy)-5-chlorobenzene]amido}-3-chlorobenzoic acid as a white solid.

MS: m/z 366 (MH⁻) and m/z 368 (MH⁺).

¹H NMR (500 MHz, DMSO-d₆): δ 2.249 (s, 3H), 7.349 (d, 1H), 7.691 (dd, 1H), 7.821 (d, 1H), 7.879 (d, 1H), 7.936 (dd, 1H), 8.009 (d, 1H), 10.279 (s, 1H), 13.264 (s, 1H).

Example 51: 5-Chloro-N-(3-chloropyridin-4-yl)-2-hydroxybenzamide

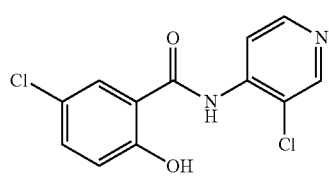 [SMILES: O=C(Nc1ccncc1Cl)c1cc(Cl)ccc1O]

Step 1: 2-Acetoxy-5-chlorobenzoyl chloride

To acetoxy-5-chlorosalicylic acid (1.43 g, 0.0067 mol) [prepared as described in Bioorg. Med. Chem. 19 (2001) 2030-2045] in a dichloromethane/dimethylformamide (45 mL/2 drops) mixture at ambient temperature was added dropwise oxalyl chloride (1.40 g, 0.011 mol). The heterogeneous mixture was stirred at ambient temperature for 3 hr. during which time it became homogeneous and gas evolution ceased. The reaction mixture was concentrated in vacuo, dichloromethane was added to the residue and the mixture was concentrated in vacuo. Repeated the dichloromethane treatment three more times to give a clear yellow oil that solidified to a tan solid overnight. This material was used without further purification.

¹H NMR (500 MHz, DMSO-d₆): δ 2.236 (s, 3H), 7.257 (d, 1H), 7.706 (dd, 1H), 7.874 (d, 1H).

Step 2: 5-Chloro-N-(3-chloropyridin-4-yl)-2-hydroxybenzamide

To a solution of 2-acetoxy-5-chlorobenzoyl chloride [Example 51, step 1] (0.65 g, 0.0028 mol) in chloroform (15 mL) was added triethylamine (0.27 g, 0.0027 mol) and the mixture was chilled to 0° C. 4-Amino-3-chloropyridine (0.35 g, 0.0027 mol) was added portionwise over 5 min. The resulting mixture was stirred at 0° C. until all of the 4-amino-3-chloropyridine had dissolved. The mixture was allowed to warm to ambient temperature and stirred overnight. The reaction was quenched by addition of 2M aqueous hydrogen chloride (1 mL). The mixture was stirred for 30 min., then extracted with 10% aqueous hydrogen chloride (2×50 mL). The pH of the combined aqueous extracts was adjusted to 8 with saturated aqueous sodium bicarbonate solution and the mixture was stirred for several hours at ambient temperature. The resulting solid was filtered, washed several times with water and air dried to give 46.6 mgs of crude product. Attempts to recrystallize the product from ethanol failed. The recovered crude product was dissolved in a dichloromethane/MeOH mixture, silica gel was added and the mixture was concentrated in vacuo. The residue was transferred to a pre-column and purified by chromatography using a gradient as follows: initially dichloromethane (1 min.), then the eluent was modified to 2% MeOH/dichloromethane over a 15 min. period and kept at 2% MeOH/dichloromethane for the remainder of the purification. The fractions containing the pure major component were combined and concentrated in vacuo to give 22.5 mg (2.9% yield) of 5-chloro-N-(3-chloropyridin-4-yl)-2-hydroxybenzamide as an off-white solid.

MS: m/z 281.1 (MH⁻) and m/z 283 (MH⁺).

¹H NMR (500 MHz, DMSO-d₆): δ 7.109 (d, 1H), 7.552 (dd, 1H), 7.970 (d, 1H), 8.512 (m, 2H), 8.671 (s, 1H).

Examples 52 and 53: 5-tert-Butyl-N-(4-carbamoyl-2-chlorophenyl)-2-hydroxybenzamide (52) and 5-tert-Butyl-N-(2-chloro-4-cyanophenyl)-2-hydroxybenzamide (53)

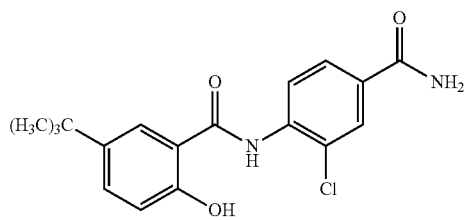

52

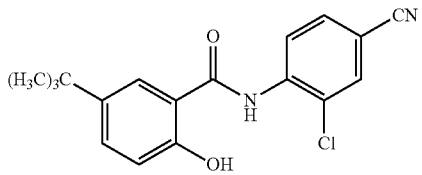

To a solution of 5-tert-butylsalicylic acid (0.191 g, 0.98 mmol) [prepared as described in WO2005110996A1] and 4-amino-3-chlorobenzamide (0.168 g, 0.98 mmol) [Prepared as described in Med Chem Lett 2011 (2) 402-406] in xylenes (5 mL) at 100° C. was added dropwise via syringe phosphorous trichloride (0.28 mL, 0.56 mmol as a 2M solution in dichloromethane). After the addition was complete, the temperature was raised to 130° C. for 4 hr. The reaction mixture was cooled to 100° C. and the hot solution was pipetted into an Erlenmeyer flask leaving an orange oily residue stuck to the sides of the reaction flask. The hot solution was stirred vigorously while cooling to ambient temperature; to produce an oily-solid residue. The residue was dissolved in ethyl acetate and washed with 1 N HCl aqueous, saturated aqueous sodium bicarbonate and brine. Silica gel was added to the organic phase and the mixture was concentrated in vacuo. The residue was transferred to a pre-column and purified by chromatography using a gradient as follows: initially hexane (1 min.), then the eluent was modified to 30% ethyl acetate/hexane over a 30 min. period and kept at 30% ethyl acetate/hexane for 14 min. Finally, the eluent was stepped up to 40% ethyl acetate/hexane and kept at 40% ethyl acetate/hexane for the remainder of the purification. The fractions containing the pure component that eluted at 40% ethyl acetate/hexane (more polar component) were combined and concentrated in vacuo to obtain a 16.4% yield of 52 as a yellow solid.

MS: m/z 345.1 (MH$^-$) and m/z 347.1 (MH$^+$).

$^1$H NMR (500 MHz, DMSO-d$_6$): δ 1.292 (s, 9H), 7.005 (d, 1H), 7.526 (dd, 1H), 7.445 (br s, 1H), 7.093 (dd, 1H), 8.031 (br s, 1H), 8.054 (m, 2H), 8.599 (dd, 1H), 11.121 (s, 1H), 11.782 (s, 1H).

The fractions containing the pure component that eluted during the modification of the eluent to 30% ethyl acetate/hexane (less polar component) were combined and concentrated in vacuo to isolate compound 53 as a pinkish-tan colored solid.

MS: m/z 327.1 (MH$^-$) and m/z 329.1 (MH$^+$).

$^1$H NMR (500 MHz, DMSO-d$_6$): δ 1.286 (s, 9H), 7.014 (d, 1H), 7.542 (dd, 1H), 7.876 (dd, 1H), 8.039 (d, 1H), 8.176 (d, 1H), 8.758 (d, 1H), 11.294 (s, 1H), 11.878 (s, 1H).

Example 54: 5-tert-Butyl-N-[4-(tert-butylcarbamoyl)-2-chlorophenyl]-2-hydroxybenzamide

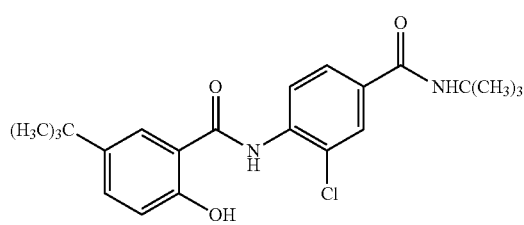

To a mixture of 4-[(5-tert-butyl-2-hydroxybenzene) amido]-3-chlorobenzoic acid [Example 4] (0.3 g, 0.86 mmol) and HOBt (0.127 g, 0.94 mmol) in dichloromethane (10 mL) was added, in one portion, diisopropylethylamine (0.223 g, 1.7 mmol). The solution became homogeneous. 1-Ethyl-3-[3-dimethyl aminopropyl]carbodiimide hydrochloride (0.18 g, 0.94 mmol) was added in one portion and the mixture was stirred at ambient temperature for 5 min. Tert-butylamine (0.063 g, 0.86 mmol) was added dropwise and the mixture was stirred at ambient temperature for 18 hr. The reaction mixture was diluted with dichloromethane and washed with saturated aqueous sodium bicarbonate, water and brine, then dried over sodium sulfate. The mixture was filtered, silica gel was added to the filtrate and the filtrate was concentrated in vacuo. The residue was transferred to a pre-column and purified by chromatography using the following gradient. Initially hexane (1 min.), the eluent was modified to 20% ethyl acetate/hexane over a 20 min. period and kept at 20% ethyl acetate/hexane for the remainder of the purification. The fractions containing the pure component exhibiting the correct mass by LC/MS were combined and concentrated in vacuo to give a glass that slowly crystallized on standing. Hexane was added to the partially crystallized product and the mixture was triturated overnight. The resulting solid was filtered, washed with hexane and air dried to give a 6.9% yield of 5-tert-butyl-N-[4-(tert-butylcarbamoyl)-2-chlorophenyl]-2-hydroxybenzamide as a white solid.

MS: m/z 401.1 (MH$^-$) and m/z 403.1 (MH$^+$).

$^1$H NMR (500 MHz, DMSO-d$_6$): δ 1.294 (s, 9H), 1.391 (s, 9H), 7.006 (d, 1H), 7.526 (dd, 1H), 7.850 (m, 2H), 8.006 (d, 1H), 8.057 (d, 1H), 8.571 (d, 1H), 11.099 (s, 1H), 11.773 (s, 1H).

Example 55: N-[4-(tert-butylcarbamoyl)-2-chlorophenyl]-2-hydroxy-5-methylbenzamide

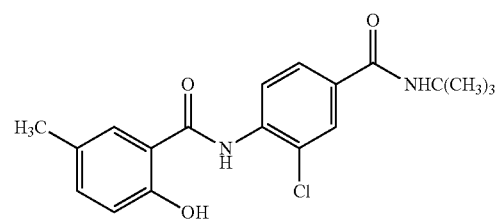

Step 1: 4-Amino-N-tert-butyl-3-chlorobenzamide

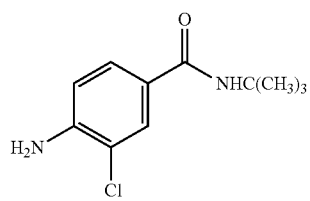

To a suspension of 4-amino-3-chlorobenzoic acid (1Mg, 6.0 mmol) in dichloromethane (20 mL) was added in one portion HOBt (0.81 g, 6.6 mmol). The reaction mixture became almost homogeneous. Diisopropylethylamine (1.55 g, 12.0 mmol) was added in one portion followed by N-(3-Dimethylamino propyl)-M-ethylcarbodiimide hydrochloride (1.27 g, 6.6 mmol) and the mixture was stirred at ambient temperature for 5 min. Tert-butylamine (0.44 g, 6.0 mmol) was added in one portion and the mixture instantaneously became heterogeneous. The mixture was stirred at ambient temperature overnight. The reaction mixture was washed with saturated aqueous sodium carbonate, water and brine and dried over sodium sulfate. The mixture was filtered and the filtrate was evaporated in vacuo to give a quantitative yield of 4-amino-N-tert-butyl-3-chlorobenzamide as a white solid.

MS: m/z 227.1 (MH$^+$).

$^1$H NMR (500 MHz, DMSO-d$_6$): δ 1.345 (s, 9H), 5.785 (s, 2H), 6.747 (d, 1H), 7.421 (s, 1H), 7.527 (dd, 1H), 7.726 (d, 1H).

Step 2: N-[4-(tert-butylcarbamoyl)-2-chlorophenyl]-2-hydroxy-5-methylbenzamide

This compound was prepared in a similar manner as described in Example 1, step 3 using 2-hydroxy-5-methylbenzoic acid in place of 2-hydroxy-5-(trifluoromethyl)benzoic acid and 4-amino-N-(tert-butyl)-3-chlorobenzamide (Example 55, step 1) to obtain N-[4-(tert-butylcarbamoyl)-2-chlorophenyl]-2-hydroxy-5-methylbenzamide as a white solid in a 40.7% yield. The product was isolated by chromatography using a gradient as follows: initially hexane, the eluent was modified to 30% ethyl acetate/hexane over a 20 min. period and kept at 30% ethyl acetate/hexane for the remainder of the purification.

MS: m/z 359.1 (MH$^-$) and m/z 361.1 (MO.

$^1$H NMR (500 MHz, DMSO-d$_6$): δ 1.388 (s, 9H), 2.288 (s, 3H), 6.962 (d, 1H), 7.283 (m, 1H), 7.842 (m, 3H), 8.002 (d, 1H), 8.560 (d, 1H), 11.092 (s, 1H), 11.719 (s, 1H).

Example 56: Methyl 4-[(5-chloro-2-hydroxybenzene)amido]-3-methoxybenzoate

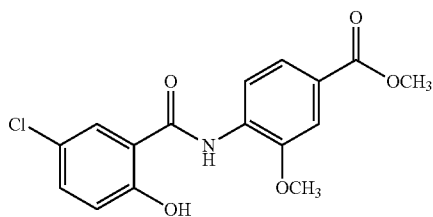 [SMILES: COC(=O)c1ccc(NC(=O)c2cc(Cl)ccc2O)c(OC)c1]

100-75: Methyl 41-[(5-chloro-2-hydroxybenzene)amido]-3-methoxybenzoate

This compound was prepared in a similar manner as described in Example 1, step 3 from 5-chloro-2-hydroxybenzoic acid and methyl 4-amino-3-methoxybenzoate (Example 42, step 1) to obtain methyl 4-[(5-chloro-2-hydroxybenzene)amido]-3-methoxybenzoate as an off-white solid. The crude solid was dissolved in ethyl acetate, silica gel was added and the mixture was concentrated in vacuo. The residue was transferred to a pre-column and purified by chromatography using a gradient as follows: initially hexane for 1 min., then the eluent was modified to 50% ethyl acetate/hexane over a 20 min. period and kept at 50% ethyl acetate/hexane for the remainder of the separation. Fractions containing the pure major component were concentrated in vacuo to give a 55.3% yield of methyl 4-[(5-chloro-2-hydroxybenzene)amido]-3-methoxybenzoate as a white solid MS: m/z 334.0 (MH$^-$) and m/z 336.1 (MH$^+$).

$^1$H NMR (500 MHz, DMSO-d$_6$): δ 3.858 (s, 3H), 3.982 (s, 3H), 7.082 (d, 1H), 7.497 (dd, 1H), 7.582 (d, 1H), 7.655 (dd, 1H), 7.966 (d, 1H), 8.598 (d, 1H), 11.112 (s, 1H), 12.147 (s, 1H).

Example 57: 4-[(5-chloro-2-hydroxybenzene)amido]-3-methoxybenzoic acid

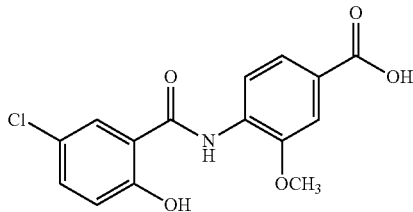 [SMILES: COc1cc(C(=O)O)ccc1NC(=O)c1cc(Cl)ccc1O]

This compound was prepared in a similar manner as described in Example 2 substituting methyl 4-[(5-chloro-2-hydroxybenzene)amido]-3-methoxybenzoate [Example 56] for methyl 3-chloro-4-{[2-hydroxy-5-(trifluoromethyl)benzene]amido}benzoate to give 4-[(5-chloro-2-hydroxybenzene)amido]-3-methoxybenzoic acid as an off-white white solid in a quantitative yield.

MS: m/z 320.0 (MH$^-$) and m/z 322.1 (MH$^+$).

$^1$H NMR (500 MHz, DMSO-d$_6$): δ 4.026 (s, 3H), 7.135 (d, 1H), 7.549 (dd, 1H), 7.632 (d, 1H), 7.681 (dd, 1H), 8.023 (d, 1H), 8.623 (d, 1H), 11.144 (s, 1H), 12.187 (s, 1H), 12.901 (s, 1H).

Example 58: 5-tert-butyl-N-(2,4-dimethoxyphenyl)-2-hydroxybenzamide

100-75: The compound 5-tert-butyl-N-(2,4-dimethoxyphenyl)-2-hydroxybenzamide was prepared in a similar manner as described in Example 1, step 3 from 5-tert-butyl-2-hydroxybenzoic acid [prepared as described in WO2005110996A1] and 2,4-dimethoxyaniline (ACROS Chemicals) to obtain 5-tert-butyl-N-(2,4-dimethoxyphenyl)-2-hydroxybenzamide. The cooled reaction solution was dissolved in ethyl acetate, silica gel was added and the mixture was concentrated in vacuo. The residue was transferred to a pre-column and purified by chromatography using a gradient as follows: initially hexane for 1 min., then the eluent was modified to 10% ethyl acetate/hexane over a 15 min. period and kept at 10% ethyl acetate/hexane for the remainder of the separation. Fractions containing the pure major component were concentrated in vacuo to give a 55.9% yield of 5-tert-butyl-N-(2,4-dimethoxyphenyl)-2-hydroxybenzamide as a tan solid.

MS: m/z 328.1 (MH$^-$) and m/z 330.1 (MH$^+$).

$^1$H NMR (500 MHz, DMSO-d$_6$): δ 1.282 (s, 9H), 3.771 (s, 3H), 3.862 (s, 3H), 6.544 (dd, 1H), 6.678 (d, 1H), 6.931 (d, 1H), 7.443 (dd, 1H), 8.023 (d, 1H), 8.149 (d, 1H), 10.571 (s, 1H), 11.545 (s, 1H).

Example 59: Methyl 4-[(5-tert-butyl-2-hydroxybenzene)amido]-3-(trifluoromethoxy)benzoate

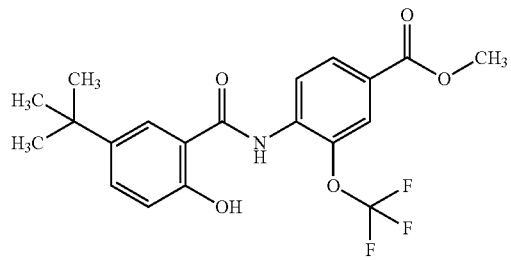 [SMILES: COC(=O)c1ccc(NC(=O)c2cc(C(C)(C)C)ccc2O)c(OC(F)(F)F)c1]

Step 1: Methyl 4-amino-3-(trifluoromethoxy)benzoate

Thionyl chloride (2.68 g, 0.023 mol) was added dropwise to methanol (12 mL) at −5° C. via a syringe keeping the temperature at or below −4° C. The resulting mixture was stirred at or below −5° C. for 1 hr., then 4-amino-3-(trifluoromethoxy)benzoic acid (0.5 g, 0.003 mol) [Alfa Aesar] was added in one portion. The reaction mixture was stirred at ambient temperature for 3 days after which the mixture was concentrated in vacuo. Water (10 mL) was added to the residue and sodium bicarbonate (0.46 g, 5.4 mmol) was added in one portion and the mixture was stirred at ambient temperature for 30 min. The mixture was extracted several times with ethyl acetate. The combined organic phase was dried over sodium sulfate, filtered and concentrated in vacuo to give 1.02 g (96.2%) of methyl 4-amino-3-(trifluoromethoxy)benzoate as a red oil that slowly solidified to a brown solid on cooling.

MS: m/z 236.1 (MH$^+$).
$^1$H NMR (500 MHz, DMSO-d$_6$): δ 3.771 (s, 3H), 6.329 (s, 2H), 6.834 (d, 1H), 7.6181 (s, 1H), 7.655 (dd, 1H).

Step 2: Methyl 4-[(5-tert-butyl-2-hydroxybenzene)amido]3-(trifluoromethoxy)benzoate This compound was prepared in a similar manner as described in Example 1, step 3 from 5-tert-butyl-2-hydroxybenzoic acid and methyl 4-amino-3-(trifluoromethoxy)benzoate (Example 59, step 1) to obtain methyl 4-[(5-tert-butyl-2-hydroxybenzene)amido]-3-(trifluoromethoxy)benzoate as a white solid. The cooled reaction mixture was dissolved in ethyl acetate, silica gel was added and the mixture was concentrated in vacuo. The residue was transferred to a pre-column and purified by chromatography using a gradient as follows: initially hexane for 1 min., then the eluent was modified to 10% ethyl acetate/hexane over a 20 min. period and kept at 10% ethyl acetate/hexane for the remainder of the separation. Two components were obtained as follows: Component A was obtained by combining the fractions containing the pure major component and concentrating in vacuo to give a 30.1% yield of the title compound. Component B was obtained by combining the fractions containing the pure major component and a very minor impurity and concentrating in vacuo to give 8.2% of the title compound containing a minor impurity. The analytical data given below was obtained using Component A, MS: m/z 410.1 (MH$^-$) and m/z 412.1 (MH$^+$).
$^1$H NMR (500 MHz, DMSO-d$_6$): δ 1.287 (s, 9H), 3.878 (s, 3H), 7.044 (d, 1H), 7.538 (dd, 1H), 7.921 (m, 1H), 8.041 (m, 2H), 8.773 (d, 1H), 11.285 (s, 1H), 11.830 (s, 1H).

Example 60: 4-[(5-tert-Butyl-2-hydroxybenzene)amido]-3-(trifluoromethoxy)benzoic acid

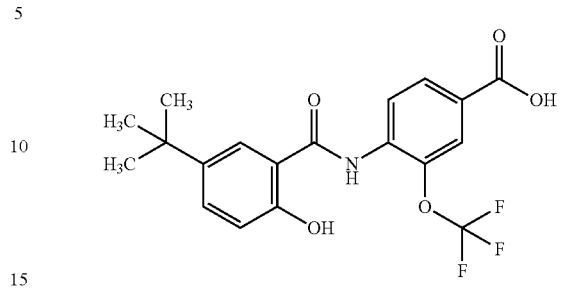

This compound was prepared in a similar manner as described in Example 2 substituting methyl 4-[(5-tert-butyl-2-hydroxybenzene)amido]-3-(trifluoromethoxy)benzoate [Example 59] for methyl 3-chloro-4-{[2-hydroxy-5-(trifluoromethyl)benzene]amido}benzoate to give 4-[(5-tert-Butyl-2-hydroxybenzene)amido]-3-(trifluoromethoxy)benzoic acid as a white white solid in a 98.1% yield.

MS: m/z 396.1 (MH$^-$) and m/z 398.1 (MH$^+$).
$^1$H NMR (500 MHz, DMSO-d$_6$): δ 1.289 (s, 9H), 7.043 (d, 1H), 7.536 (dd, 1H), 7.901 (t, 1H), 8.012 (dd, 1H), 8.046 (d, 1H), 8.741 (d, 1H), 11.258 (s, 1H), 11.814 (s, 1H), 13.237 (s, 1H).

Example 61: Methyl 3-chloro-4-[(5-ethyl-2-hydroxybenzene)amido]benzoate

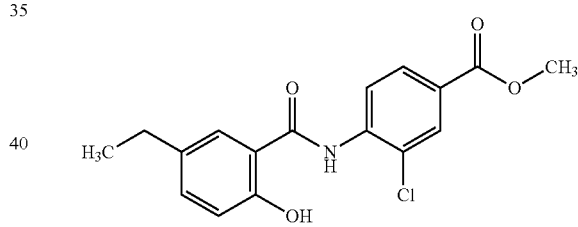

Step 1: 5-Ethyl-2-hydroxybenzaldehyde

This compound was prepared in a similar manner as described in Example 1, step 1 by substituting 4-ethylphenol [ACROS Organics] for 4-trifluoromethyl phenol except for column chromatography, hexane was used as eluent initially for one min., then the eluent was modified to 2% Ethyl Acetate/hexane over a 19 min. period and kept at 2% Ethyl Acetate/hexane for the remainder of the purification to give a 83.6% yield of 5-ethyl-2-hydroxybenzaldehyde as a pale yellow oil.

MS: m/z 151.1 (MH$^+$).
$^1$H NMR (500 MHz, DMSO-d$_6$): δ 1.153 (t, 3H), 2.557 (q, 2H), 6.925 (d, 1H), 7.381 (dd, 1H), 7.481 (d, 1H), 10.229 (s, 1H), 10.491 (s, 1H).

Step 2: 5-Ethyl-2-hydroxybenzoic acid

This compound was prepared in a similar manner as described in Example 1, step 2 substituting 5-ethyl-2-hydroxybenzaldehyde (Example 61, step 1) for 2-hydroxy-5-(trifluoromethyl)benzaldehyde. The crude product was recrystallized from methanol/water mixtures to give a 79.6% yield of 5-ethyl-2-hydroxybenzoic acid as a tan solid (component A). A second crop of product representing an additional 7.2% yield was obtained as a white solid (component B). The LC/MS and NMR for both components were similar. The data reported below was obtained from component A.

MS: m/z 165.2 (MH$^-$).

$^1$H NMR (500 MHz, DMSO-d$_6$): δ 1.148 (t, 3H), 2.552 (q, 2H), 6.877 (d, 1H), 7.368 (dd, 1H), 7.608 (d, 1H), 11.101 (br s, 1H), 13.825 (br s, 1H).

Step 3: Methyl 3-chloro-4-[(5-ethyl-2-hydroxybenzene)amido]benzoate

This compound was prepared in a similar manner as described in Example 1, step 3 from 5-ethyl-2-hydroxybenzoic acid [prepared as described in WO2005110996A1, Example 61 steps 1 and 2] and methyl 4-amino-3-chlorobenzoate to obtain methyl 3-chloro-4-[(5-ethyl-2-hydroxybenzene)amido]benzoate as a white solid. The preabsorbed (on silica gel) material was purified by chromatography using a gradient as follows: initially hexane for 1 min., then the eluent was modified to 15% ethyl acetate/hexane over a 20 min. period and kept at 15% ethyl acetate/hexane for the remainder of the separation. The fractions containing pure product were combined and concentrated in vacuo to give a 39.5% yield of methyl 3-chloro-4-[(5-ethyl-2-hydroxybenzene)amido]benzoate as a white solid.

MS: m/z 332.1 (MH$^-$) and m/z, 334.1 (MH$^+$).

$^1$H NMR (500 MHz, DMSO-d$_6$): δ 1.178 (t, 3H), 2.595 (q, 2H), 3.866 (s, 3H), 6.993 (d, 1H), 7.329 (dd, 1H), 7.872 (d, 1H), 7.976 (dd, 1H), 8.048 (d, 1H), 8.723 (d, 1H), 11.241 (s, 1H), 11.804 (s, 1H).

Example 62: 3-Chloro-4-[(5-ethyl-2-hydroxybenzene)amido]benzoic acid

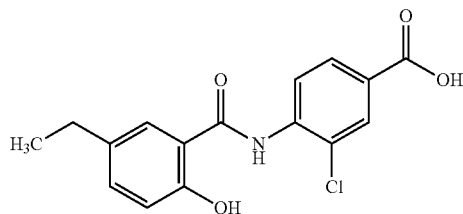 [SMILES: CCc1ccc(O)c(C(=O)Nc2ccc(C(=O)O)cc2Cl)c1]

This compound was prepared in a similar manner as described in Example 2 substituting methyl 3-chloro-4-[(5-ethyl-2-hydroxybenzene)amido]benzoate [Example 61] for methyl 3-chloro-4-{[2-hydroxy-5-(trifluoromethyl)benzene]amido}benzoate to give 3-chloro-4-[(5-ethyl-2-hydroxybenzene)amido]benzoic acid as a pale yellow white solid in a 96.7% yield.

MS: m/z 318.1 (MH$^-$) and m/z 320.1 (MH$^+$).

$^1$H NMR (500 MHz, DMSO-d$_6$): δ 1.178 (t, 3H), 2.595 (q, 2H) 6.990 (d, 1H), 7.325 (dd, 1H), 7.874 (d, 1H), 7.948 (dd, 1H), 8.019 (d, 1H), 8.688 (d, 1H), 11.212 (s, 1H), 11.791 (s, 1H), 13.102 (br s, 1H).

Example 63: Methyl 3-chloro-4-[(5-cyclohexyl-2-hydroxybenzene)amido]benzoate

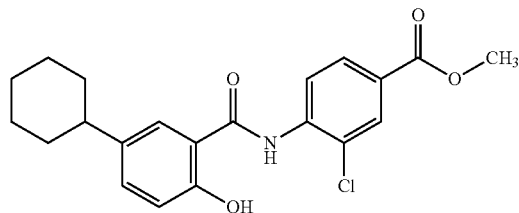 [SMILES: COC(=O)c1ccc(NC(=O)c2cc(C3CCCCC3)ccc2O)c(Cl)c1]

Step 1: 5-Cyclohexyl-2-hydroxybenzaldehyde

This compound was prepared in a similar manner as described in Example 1, step 1 by substituting 4-cyclohexylphenol [TCI] for 4-trifluoromethylphenol except for column chromatography, hexane was used as eluent initially for one min., then the eluent was modified to 2% Ethyl Acetate/hexane over a 20 min. period and kept at 2% Ethyl Acetate/hexane for the remainder of the purification to give a 86.4% yield of 5-cyclohexyl-2-hydroxybenzaldehyde as a pale yellow oil.

MS: m/z 205.1 (MH$^+$).

$^1$H NMR (500 MHz, DMSO-d$_6$): δ 1.214 (m, 1H), 1.347 (m, 4H), 1.684 (m, 1H), 1.768 (m, 4H), 2.457 (m, 1H), 6.917 (d, 1H), 7.397 (dd, 1H), 7.487 (d, 1H), 10.219 (s, 1H), 10.490 (s, 1H).

Step 2: 5-Cyclohexyl-2-hydroxybenzoic acid

This compound was prepared in a similar manner as described in Example 1, step 2 substituting 5-cyclohexyl-2-hydroxybenzaldehyde (Example 63, step 1) for 2-hydroxy-5-(trifluoromethyl)benzaldehyde to give a quantitative yield of 5-cyclohexyl-2-hydroxy benzoic acid as an off-white solid.

MS: m/z 219.1 (MH$^-$).

$^1$H NMR (500 MHz, DMSO-d$_6$): δ 1.208 (m, 1H), 1.361 (m, 4H), 1.690 (m, 1H), 1.772 (br s, 4H), 2.459 (m, 1H), 6.875 (d, 1H), 7.386 (dd, 1H), 7.608 (d, 1H), 11.065 (br s, 1H), 13.859 (br s, 1H),

Step 3: Methyl 3-chloro-4-[(5-cyclohexyl-2-hydroxybenzene)amido]benzoate

This compound was prepared in a similar manner as described in Example 1, step 3 from 5-cyclohexyl-2-hydroxybenzoic acid [prepared as described in WO2005110996A1, Example 63 steps 1 and 2] and methyl 4-amino-3-chlorobenzoate to obtain methyl 3-chloro-4-[(5-cyclohexyl-2-hydroxybenzene)amido]benzoate as a white solid. The preabsorbed (on silica gel) material was purified by chromatography using a gradient as follows: initially hexane for 1 min., then the eluent was modified to 20% ethyl acetate/hexane over a 20 min. period and kept at 20% ethyl acetate/hexane for the remainder of the separation. The fractions containing pure product were combined and concentrated in vacuo to give a 31.8% yield of methyl 3-chloro-4-[(5-cyclohexyl-2-hydroxybenzene)amido]benzoate as a white solid.

MS: m/z 386.1 (MH⁻) and m/z 388.1 (MH⁺).

¹H NMR (500 MHz, DMSO-$d_6$): δ 1.238 (m, 1H), 1.372 (m, 4H), 1.704 (br d, 1H), 1.790 (br d, 4H), 2.494 (m, 1H), 3.864 (s, 3H), 6.987 (d, 1H), 7.343 (dd, 1H), 7.879 (d, 1H), 7.976 (dd, 1H), 8.046 (d, 1H), 8.712 (d, 1H), 11.229 (s, 1H), 11.803 (s, 1H).

Example 64: 3-Chloro-4[(5-cyclohexyl-2-hydroxybenzene)amido]benzoic acid

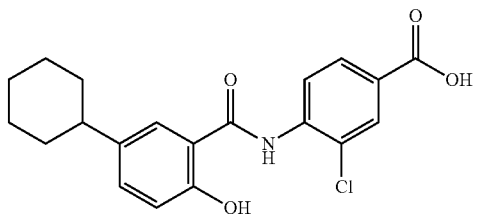 [SMILES: O=C(O)c1ccc(NC(=O)c2cc(C3CCCCC3)ccc2O)c(Cl)c1]

This compound was prepared in a similar manner as described in Example 2 substituting methyl 3-chloro-4-[(5-cyclohexyl-2-hydroxybenzene)amido]benzoate [Example 63] for methyl 3-chloro-4-{[2-hydroxy-5-(trifluoromethyl)benzene]amido}benzoate to give a quantitative yield of 3-chloro-4-[(5-cyclohexyl-2-hydroxybenzene)amido]benzoic acid as a white solid.

MS: m/z 372 (MH⁻) and m/z 374.1 (MH⁺).

¹H NMR (500 MHz, DMSO-$d_6$): δ 1.232 (br m, 1H), 1.377 (br m, 4H) 1.703 (br d, 1H), 1.792 (br d, 4H), 6.986 (d, 1H), 7.341 (dd, 1H), 7.883 (d, 1H), 7.949 (dd, 1H), 8.019 (d, 1H), 8.677 (d, 1H), 11.202 (s, 1H), 11.793 (s, 1H), 13.126 (s, 1H).

Example 65: Methyl 4-[(2-hydroxy-5-trifluoromethylbenzene)amido]-3-methoxybenzoate

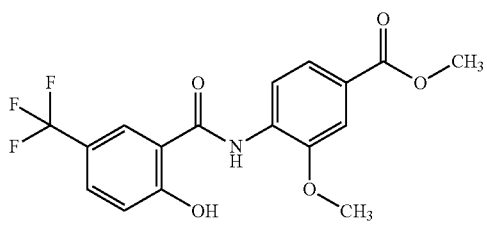 [SMILES: COC(=O)c1ccc(NC(=O)c2cc(C(F)(F)F)ccc2O)c(OC)c1]

Methyl 4-[(2-hydroxy-5-{trifluoromethyl}benzene)amido]-3-methoxybenzoate

This compound was prepared in a similar manner as described in Example 1, step 3 from 2-hydroxy-5-trifluoromethylbenzoic acid [prepared as described Example 1, Steps 1 & 2] and methyl 4-amino-3-methoxybenzoate (Example 42, step 1) to obtain methyl 4-[(2-hydroxy-5-{trifluoromethyl}benzene)amino]-3-methoxybenzoate as an off-white solid. The crude solid was dissolved in ethyl acetate, silica gel was added and the mixture was concentrated in vacuo. The residue was transferred to a pre-column and purified on the Combiflash Rf system using initially hexane for 1 min., then the eluent was modified to 30% ethyl acetate/hexane over a 15 min. period and the eluent was kept at 30% ethyl acetate/hexane for the remainder of the separation. Fractions containing the pure major component were concentrated in vacuo to give a 56.9% yield of methyl 4-[(2-hydroxy-5-{trifluoromethyl}benzene)amido]-3-methoxybenzoate as a white solid MS: m/z 368.1 (MH⁻) and m/z 370.1 (MH⁺).

¹H NMR (500 MHz, DMSO-$d_6$): δ 3.861 (s, 3H), 3.994 (s, 3H), 7.242 (d, 1H), 7.593 (d, 1H), 7.665 (dd, 1H), 7.806 (dd, 1H), 8.311 (d, 1H), 8.608 (d, 1H), 11.109 (s, 1H), 12.793 (s, 1H).

Example 66: 4-[(2-hydroxy-5-{trifluoromethyl}benzene)amido]-3-methoxybenzoic acid

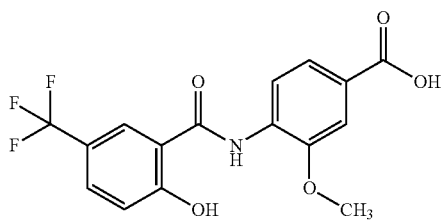

This compound was prepared in a similar manner as described in Example 2 substituting methyl 4-[(2-hydroxy-5-{trifluoromethyl}phenyl)amido]-3-methoxybenzoate [Example 65] for methyl 3-chloro-4-{[2-hydroxy-5-(trifluoromethyl)benzene]amido}benzoate to give 4-[(2-hydroxy-5-{trifluoromethyl}benzene)amido]-3-methoxybenzoic acid as an off-white white solid in a quantitative yield.

MS: m/z 354.1 (MH⁻) and m/z 356.1 (MH⁺).

¹H NMR (500 MHz, DMSO-$d_6$): δ 3.985 (s, 3H), 7.242 (d, 1H), 7.591 (d, 1H), 7.639 (dd, 1H), 7.806 (dd, 1H), 8.316 (d, 1H), 8.579 (d, 1H), 11.092 (s, 1H), 12.782 (s, 1H), 12.863 (s, 1H).

Example 67: Methyl 3-chloro-4-[(5-chloro-2-methoxybenzene)amido]benzoate

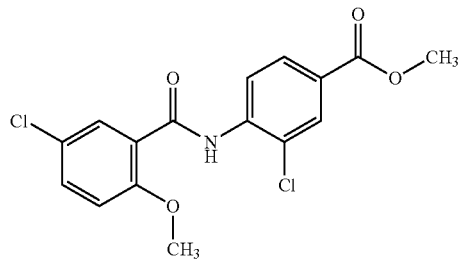 [SMILES: COC(=O)c1ccc(NC(=O)c2cc(Cl)ccc2OC)c(Cl)c1]

Step 1: 5-Chloro-2-methoxybenzoic acid

To a solution of Methyl 5-chloro-2-methoxybenzoate (2.0 g, 0.01 mol) [Alfa Aesar] in ethanol (60 mL) was added in one portion IM aqueous sodium hydroxide (60 mL, 0.06 mol) and the mixture was stirred at ambient temperature for 4 hr. Thin layer chromatography indicated that the reaction was complete. Concentrated the mixture in vacuo to remove the ethanol and extracted the aqueous residue with ethyl acetate. Chilled the aqueous phase in an ice bath and adjusted the pH to 2 with concentrated aqueous hydrogen chloride. After stirring in an ice bath for 1 hr., the resulting solid was filtered, washed with water and air dried to give 1.4 g (74.9%) of 3-chloro-2-methoxy benzoic acid as a white solid MS: m/z 185.1 (MH⁻).
$^1$H NMR (500 MHz, DMSO-$d_6$): δ 3.818 (s, 3H), 7.162 (d, 1H), 7.551 (dd, 1H), 7.607 (d, Step 2: Methyl 3-chloro-4-[(5-chloro-2-methoxybenzene)amido]benzoate This compound was prepared in a similar manner as described in Example 1, step 3 from 5-chloro-2-methoxybenzoic acid [prepared as described Example 67, Step 1] and methyl 4-amino-3-chlorobenzoate to obtain methyl 3-chloro-4-[(5-chloro-2-methoxybenzene)amido]benzoate. In this case the compound solidified out of the hot solution during transfer to the Erlenmeyer. Once all of the hot solution had been transferred, the compound was dissolved by addition of dichloromethane and the solution was concentrated in vacuo. The residue was dissolved in hot ethyl acetate, filtered and allowed to come to ambient temperature overnight. The resulting solid was filtered, washed once with ethyl acetate and several times with hexanes and air dried to give methyl 3-chloro-4-[(5-chloro-2-methoxybenzene)amino]-3-benzoate as a white solid in 43.8% yield.

MS: m/z 354.0 (MH⁺).
$^1$H NMR (500 MHz, DMSO-$d_6$): δ 3.866 (s, 3H), 4.105 (s, 3H), 7.371 (d, 1H), 7.697 (dd, 1H), 7.977 (dd, 1H), 7.998 (d, 1H), 8.054 (d, 1H), 8.644 (d, 1H), 10.768 (s, 1H).

Example 68: 3-Chloro-4-[(5-Chloro-2-methoxybenzene)amido]benzoic acid

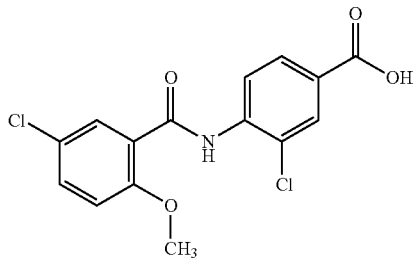 [SMILES: COc1ccc(Cl)cc1C(=O)Nc1ccc(C(=O)O)cc1Cl]

This compound was prepared in a similar manner as described in Example 2 substituting methyl 3-chloro-4-[(5-chloro-2-methoxybenzene)amido]benzoate [Example 67] for methyl 3-chloro-4-{[2-hydroxy-5-(trifluoromethyl)benzene]amido}benzoate to give 3-chloro-4-[(5-chloro-2-methoxybenzene)amido]benzoic acid. In this case, after stirring at ambient temperature for 1 hr, the mixture was warmed to 40° C. for 3 hr. The mixture was stirred at ambient temperature overnight but never became homogeneous. Thin layer chromatography indicated the reaction was complete and the reaction was worked up in the usual fashion.

LC/MS of the isolated product showed the presence of some starting methyl ester. The solid was dissolved in 0.15M aqueous NaOH and washed with ethyl acetate several times. The ethyl acetate washes were discarded. The aqueous phase was filtered to remove a small amount of solid material, the pH was adjusted to 2 with 1N aqueous HCl and extracted with ethyl acetate. The ethyl acetate extracts were washed with water and dried over sodium sulfate. The mixture was filtered and concentrated in vacuo to give 3-chloro-4-[(5-chloro-2-methoxybenzene)amido]benzoic acid as a white solid in a 1.9% yield.

MS: m/z 338.0 (MH⁻) and m/z 340.0 (MH⁺).
$^1$H NMR (500 MHz, DMSO-$d_6$): δ 4.108 (s, 3H), 7.379 (d, 1H), 7.704 (dd, 1H), 7.961 (dd, 1H), 8.008 (d, 1H), 8.039 (d, 1H), 8.620 (d, 1H), 10.758 (s, 1H), 13.169 (br s, 1H).

Example 69: Methyl 4-[(5-tert-butyl-2-hydroxybenzene)amido]-3-isopropoxybenzoate

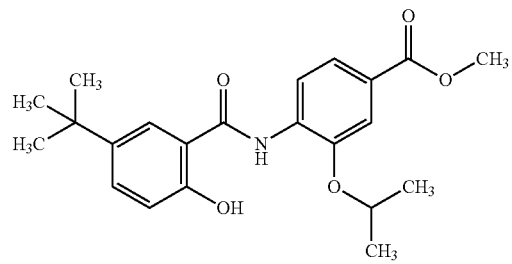 [SMILES: COC(=O)c1ccc(NC(=O)c2cc(C(C)(C)C)ccc2O)c(OC(C)C)c1]

Step 1: Methyl 4-amino-3-isopropoxybenzoate

This compound was prepared with minor modifications as described in PCT Int. Appl. 2005079541 (1 Sep. 2005) as follows: To a solution of Methyl 4-amino-3-hydroxybenzoate (1.0 g, 6.0 mmol) in acetone (20 mL) at ambient temperature was added 2-bromopropane (1.1 g, 9.0 mmol) followed by cesium carbonate (3.9 g, 12 mmol) each in one portion. The resulting mixture was heated a reflux temperature for 6 hr. Concentrated ammonium hydroxide (5 mL) was added and the mixture was refluxed for an additional 30 min. After cooling to ambient temperature the mixture was diluted with water (100 mL) and extracted with 3×75 mL of diethyl ether. The combined extracts were washed with 2×50 mL of brine and dried over magnesium sulfate. The mixture was filtered and concentrated in vacuo. The residue was taken up in diethyl ether, silica gel was added and the mixture concentrated in vacuo. The residue was transferred to a pre-column and purified by chromatography using initially hexanes (1 min.) as eluent. The eluent was modified to 30% ethyl acetate/hexanes over a 15 min. period and kept at 30% ethyl acetate/hexanes for the remainder of the purification. Fractions containing the pure desired component were combined and concentrated in vacuo to give 1.03 g (82.7% yield) of a pale yellow oil that solidified on standing to a white solid.

MS: m/z 210.1 (MH⁻).
$^1$H NMR (500 MHz, DMSO-$d_6$): δ 1.279 (d, 6H), 3.744 (s, 3H), 4.525 (m, 1H), 5.532 (s, 2H), 6.651 (d, 1H), 7.299 (d, 1H), 7.363 (dd,

Step 2: Methyl 4-[(5-tert-butyl-2-hydroxybenzene)amido]-3-isopropoxybenzoate

This compound was prepared in a similar manner as described in Example 1, step 3 from 5-tert-butyl-2-hydroxybenzoic acid [prepared as described in WO2005110996A1] and methyl 4-amino-3-isopropoxybenzoate (Example 69, step 1) to obtain methyl 4-[(5-tert-butyl-2-hydroxybenzene)

amido]-3-isopropoxybenzoate. Before chromatography, the cooled, pipetted reaction mixture was dissolved in ethyl acetate, silica gel was added and the mixture was concentrated in vacuo. The residue was transferred to a pre-column and purified by chromatography on a using initially hexanes for 1 min., then the eluent was modified to 20% ethyl acetate/hexanes over a 20 min. period, and held at 20% ethyl acetate/hexanes for the remainder of the separation. The fractions containing pure product were combined and concentrated in vacuo to give a 40.8% yield of methyl 4-[(5-tert-butyl-2-hydroxy)amido]-3-isopropoxybenzoate as an off-white solid.

MS: m/z 384.2 (MH$^-$) and m/z 386.2 (MH$^+$).

$^1$H NMR (500 MHz, DMSO-d$_6$): δ 1.287 (s, 9H), 1.373 (d, 6H), 3.846 (s, 3H), 4.796 (m, 1H), 7.031 (d, 1H), 7.497 (dd, 1H), 7.578 (d, 1H), 7.618 (dd, 1H), 8.051 (d, 1H), 8.662 (d, 1H), 11.223 (s, 1H), 11.411 (s, 1H).

Example 70: 4-[(5-tert-Butyl-2-hydroxybenzene)amido]-3-isopropoxybenzoic acid

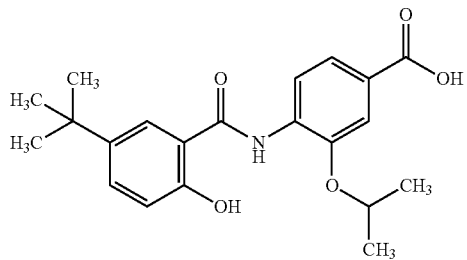 [SMILES: CC(C)Oc1cc(C(=O)O)ccc1NC(=O)c1cc(C(C)(C)C)ccc1O]

This compound was prepared in a similar manner as described in Example 2 substituting methyl 4-[(5-tert-butyl-2-hydroxybenzene)amido]-3-isopropoxybenzoate [Example 69, Step 2] for methyl 3-chloro-4-{[2-hydroxy-5-(trifluoromethyl)benzene]amido}benzoate to give 4-[(5-tert-butyl-2-hydroxybenzene)amido]-3-isopropoxybenzoic acid. In this case, the mixture was stirred at ambient temperature for 5 hr. The pH was adjusted to 2 and the reaction was worked up as described in Example 2 to give 4-[(5-tert-butyl-2-hydroxybenzene)amido]-3-isopropoxybenzoic acid as an off-white solid in a quantitative yield.

MS: m/z 370.1 (MH$^-$) and m/z 372.2 (MH$^+$).

$^1$H NMR (500 MHz, DMSO-d$_6$): δ 1.287 (s, 9H), 1.372 (d, 6H), 4.775 (m, 1H), 7.028 (d, 1H), 7.493 (dd, 1H), 7.563 (d, 1H), 7.588 (dd, 1H), 8.041 (d, 1H), 8.632 (d, 1H), 11.196 (s, 1H), 11.392 (s, 1H), 12.769 (br s, 1H).

Example 71: Methyl 4-[(5-tert-butyl-2-hydroxybenzene)amido]-3-ethoxybenzoate

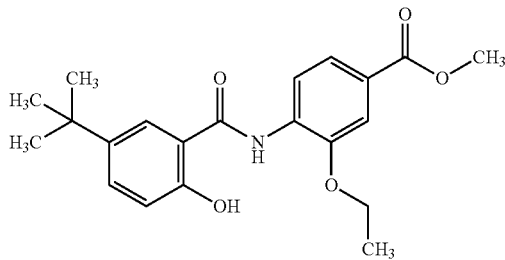 [SMILES: CCOc1cc(C(=O)OC)ccc1NC(=O)c1cc(C(C)(C)C)ccc1O]

Step 1: Methyl 4-amino-3-ethoxybenzoate

This compound was prepared using the procedure as described in Example 69, Step 1 with minor modifications. In this case the desired product was purified as follows: After drying and filtering, silica gel was added and the mixture concentrated in vacuo. The residue was transferred to a pre-column and purified by chromatography using initially hexanes (1 min.) as eluent. The eluent was modified to 20% ethyl acetate/hexanes over a 24 min. period and kept at 20% ethyl acetate/hexanes for the remainder of the purification. Fractions containing the pure desired component were combined and concentrated in vacuo to give methyl 4-amino-3-ethoxybenzoate in a 66.7% yield as a yellow solid.

MS: m/z 196.1 (MH$^+$).

$^1$H NMR (500 MHz, DMSO-d$_6$): δ 1.358 (t, 3H), 3.745 (s, 3H), 4.035 (q, 2H), 5.573 (s, 2H), 6.644 (d, 1H), 7.275 (d, 1H), 7.373 (dd, 1H).

Step 2: Methyl 4-[(5-tert-butyl-2-hydroxybenzene)amido]-3-ethoxybenzoate

This compound was prepared in a similar manner as described in Example 1, step 3 from 5-tert-butyl-2-hydroxybenzoic acid [prepared as described in WO2005110996A1] and methyl 4-amino-3-ethoxybenzoate (Example 71, step 1) to obtain methyl 4-[(5-tert-butyl-2-hydroxybenzene)amido]-3-ethoxybenzoate. Before chromatography, the cooled, pipetted reaction mixture was dissolved in ethyl acetate, silica gel was added and the mixture was concentrated in vacuo. The residue was transferred to a pre-column and purified by chromatography on a using initially hexanes for 1 min., then the eluent was modified to 20% ethyl acetate/hexanes over a 20 min. period, and held at 20% ethyl acetate/hexanes for the remainder of the separation. The fractions containing pure product were combined and concentrated in vacuo to give a 70.2% yield of methyl 4-[(5-tert-butyl-2-hydroxybenzene)amido]-3-ethoxybenzoate as an off-white solid.

MS: m/z 370.1 (MH$^-$) and m/z 372.1 (MH$^+$).

$^1$H NMR (500 MHz, DMSO-d$_6$): δ 1.289 (s, 9H), 1.472 (t, 3H), 3.847 (s, 3H), 4.209 (q, 2H), 7.028 (d, 1H), 7.497 (dd, 1H), 7.540 (d, 1H), 7.632 (dd, 1H), 8.055 (d, 1H), 8.651 (d, 1H), 11.236 (s, 1H), 11.435 (s, 1H).

Example 72: 4-[(5-tert-Butyl-2-hydroxybenzene)amido]-3-ethoxybenzoic acid

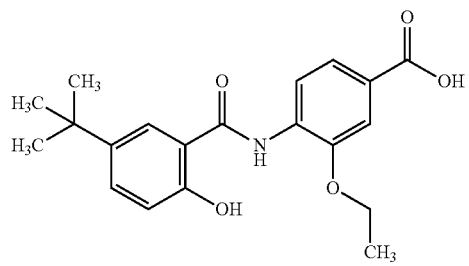 [SMILES: CCOc1cc(C(=O)O)ccc1NC(=O)c1cc(C(C)(C)C)ccc1O]

This compound was prepared in a similar manner as described in Example 2 substituting methyl 4-[(5-tert-butyl-2-hydroxybenzene)amido]-3-ethoxybenzoate [Example 71, Step 2] for methyl 3-chloro-4-{[2-hydroxy-5-(trifluoromethyl)benzene]amido}benzoate to give 4-[(5-tert-butyl-2-hydroxybenzene)amido]-3-ethoxybenzoic acid. In this case, the mixture was stirred at ambient temperature for 4.5 hr. The pH was adjusted to =2 and the reaction was worked up as described in Example 2 to give 4-[(5-tert-butyl-2-hydroxybenzene)amido]-3-ethoxybenzoic acid as an off-white solid in a 98.1% yield.

MS: m/z 356.1 (MH$^-$) and m/z 358.1 (MH$^+$).

$^1$H NMR (500 MHz, DMSO-d$_6$): δ 1.290 (s, 9H), 1.470 (t, 3H), 4.201 (q, 2H), 7.026 (d, 1H), 7.496 (dd, 1H), 7.535 (d, 1H), 7.604 (dd, 1H), 8.056 (d, 1H), 8.622 (d, 1H), 11.210 (s, 1H), 11.421 (s, 1H), 12.775 (br s, 1H).

Example 73: Methyl 3-chloro-4-[(2-hydroxy-5-phenylbenzene)amido]benzoate

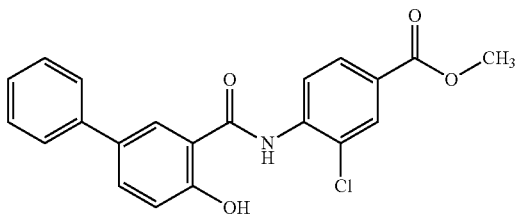 [SMILES: COC(=O)c1ccc(NC(=O)c2cc(-c3ccccc3)ccc2O)c(Cl)c1]

Step 1: 2-Hydroxy-5-phenylbenzaldehyde

This compound was prepared in a similar manner as described in Example 1, step 1 by substituting 4-phenylphenol [ACROS Organics] for 4-trifluoromethyl phenol except for column chromatography, hexane was used as eluent initially for one min., then the eluent was modified to 5% Ethyl Acetate/hexane over a 20 min. period and kept at 5% ethyl acetate/hexane for the remainder of the purification. Obtained two components: Component 1 was obtained by combining the fraction containing the pure desired product and concentrated in vacuo to give a 53.9% yield of a yellow solid. Component 2 was obtained by combining the fractions containing the desired product and starting material and concentrating in vacuo. The residue was rechromatographed using initially hexane (10 min), then the eluent was modified to 5% ethyl acetate/hexane over a 20 min. period and kept at 5% ethyl acetate/hexane for the remainder of the separation. The fractions containing the pure desired product were combined and concentrated in vacuo to give Component 2 in a 17.0% yield as a yellow solid. Total yield of 2-hydroxy-5-phenyl benzaldehyde was 70.9%. Both Components were identical by LC and NMR. The data below is for Component 2

MS: m/z 198 (M).

$^1$H NMR (500 MHz, DMSO-d$_6$): δ 7.111 (d, 1H), 7.346 (t, 1H), 7.459 (t, 2H), 7.637 (d, 2H), 7.862 (dd, 1H), 7.938 (d, 1H), 10.327 (s, 1H), 10.838 (s, 1H).

Step 2: 2-Hydroxy-5-phenylbenzoic acid

This compound was prepared in a similar manner as described in Example 1, step 2 substituting 2-hydroxy-5-phenylbenzaldehyde (Example 73, step 1) for 2-hydroxy-5-(trifluoromethyl)benzaldehyde to give the crude desired product as a white solid. This material was used without further purification.

MS: m/z 213.0 (MH$^-$).

$^1$H NMR (500 MHz, DMSO-d$_6$): δ 7.067 (d, 1H), 7.350 (br d, 1H), 7.456 (br t, 2H), 7.623 (d, 2H), 7.838 (br d, 1H), 8.037 (s, 1H), 11.346 (br s, 1H), 13.762 (br s, 1H).

Step 3: Methyl 3-chloro-4-[(2-hydroxy-5-phenylbenzene)amido]benzoate

This compound was prepared in a similar manner as described in Example 1, step 3 from 2-hydroxy-5-phenylbenzoic acid [prepared as described in WO2005110996A1, Example 73 steps 1 and 2] and methyl 4-amino-3-chlorobenzoate to obtain methyl 3-chloro-4-[(2-hydroxy-5-phenylbenzene)amido]benzoate as an off-white solid. The initial crude solid and the cooled hot reaction mixture were combined, diluted with ethyl acetate, silica gel was added and the mixture was concentrated in vacuo. The preabsorbed (on silica gel) material was purified by chromatography using a gradient as follows: initially hexane for 1 min., then the eluent was modified to 20% ethyl acetate/hexane over a 20 min. period and kept at 20% ethyl acetate/hexane for the remainder of the separation. The product was isolated as follows: Several fractions contained precipitated solid. These fractions were filtered and the solid was washed with hexanes to give 5.45% of the pure product as a white solid (A). The filtrate from A and the remaining fractions that contained impure product were combined and concentrated in vacuo. This was rechromatographed using initially hexane for 1 min., then the eluent was modified to 30% ethyl acetate/hexane over a 15 min. period and kept at 30% ethyl acetate/hexane for the remainder of the separation. The fractions containing pure product were combined and concentrated to give a 6.88% yield of pure product as a white solid (B). (A) and (B) were combined and mixed thoroughly to give a 12.3% yield of methyl 3-chloro-4-[(2-hydroxy-5-phenylbenzene)amido]benzoate as an off-white solid.

MS: m/z 380 (MH$^-$) and m/z 382 (MH$^+$).

$^1$H NMR (500 MHz, DMSO-d$_6$): δ 3.875 (s, 3H), 7.176 (d, 1H), 7.358 (t, 1H), 7.478 (m, 2H), 7.652 (dd, 2H), 7.812 (dd, 1H), 7.999 (dd, 1H), 8.072 (d, 1H), 8.316 (d, 1H), 8.730 (d, 1H), 11.262 (s, 1H), 12.225 (s, 1H).

Example 74: 3-Chloro-4-[(2-hydroxy-5-phenylbenzene)amido]benzoic acid

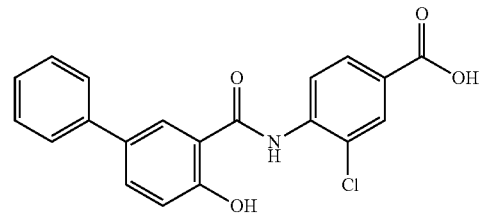 [SMILES: O=C(O)c1ccc(NC(=O)c2cc(-c3ccccc3)ccc2O)c(Cl)c1]

This compound was prepared in a similar manner as described in Example 2 substituting methyl 3-chloro-4-[(2-hydroxy-5-phenylbenzene)amido]benzoate [Example 73] for methyl 3-chloro-4-{[2-hydroxy-5-(trifluoromethyl)benzene]amido}benzoate to give 3-chloro-4-[(2-hydroxy-5-phenyl benzene)amido]benzoic acid as an off-white solid in a 93.3% yield.

MS: m/z 366 (MH$^-$) and m/z 368 (MH$^+$).

$^1$H NMR (500 MHz, DMSO-d$_6$): δ 7.172 (d, 1H), 7.356 (t, 1H) 7.475 (t, 2H), 7.654 (d, 2H), 7.809 (d, 1H), 7.970 (dd,

1H), 8.041 (s, 1H), 8.319 (s, 1H), 8.690 (d, 1H), 11.228 (s, 1H), 12.211 (s, 1H), 13.158 (s, 1H).

Example 75: Methyl 3-chloro-4-[(2-hydroxy-5-propylbenzene)amido]benzoate

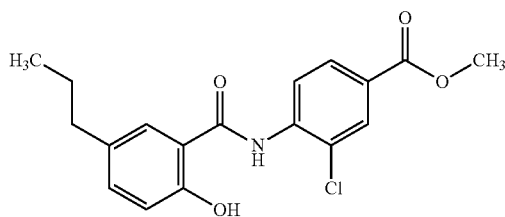 [SMILES: CCCc1ccc(O)c(C(=O)Nc2ccc(C(=O)OC)cc2Cl)c1]

Step 1: 2-Hydroxy-5-propylbenzaldehyde

This compound was prepared in a similar manner as described in Example 1, step 1 by substituting 4-propylphenol [ACROS Organics] for 4-trifluoromethyl phenol except for column chromatography. The crude product was purified using hexane as eluent. The fractions containing the pure product were concentrated in vacuo to give a 85.9% yield of 2-hydroxy-5-propylbenzaldehyde as a pale yellow oil.

$^1$H NMR (500 MHz, DMSO-$d_6$): δ 0.867 (t, 3H), 1.549 (q, 2H), =2.502 (2H under DMSO peak), 6.918 (d, 1H), 7.354 (d, 1H), 7.458 (s, 1H), 10.224 (s, 1H), 10.491 (s, 1H).

Step 2: 2-Hydroxy-5-propylbenzoic acid

This compound was prepared in a similar manner as described in Example 1, step 2 substituting 2-hydroxy-5-propylbenzaldehyde (Example 75, step 1) for 2-hydroxy-5-(trifluoromethyl)benzaldehyde to give the crude desired product as a reddish-white solid. This material was purified by chromatography using initially dichloromethane as eluent for one min., then the eluent was modified to 5% MeOH/dichloromethane over a 20 min. period and kept at 5% MeOH/dichloromethane for the remainder of the purification. The fractions containing the pure desired product were combined and concentrated in vacuo to give a 46.8% yield of 2-hydroxy-5-propylbenzoic acid as an off-white solid.

MS: m/z 179.0 (MH$^-$).

$^1$H NMR (500 MHz, DMSO-$d_6$): δ 0.871 (t, 3H), 1.549 (q, 2H), ~2.504 (2H under DMSO peak), 6.873 (d, 1H), 7.346 (d, 1H), 7.588 (s, 1H), 11.105 (br s, 1H), 13.886 (br s, 1H).

Step 3: Methyl 3-chloro-4-[(2-hydroxy-5-propylbenzene)amido]benzoate

This compound was prepared in a similar manner as described in Example 1, step 3 from 2-hydroxy-5-propylbenzoic acid [prepared as described in WO2005110996A1, Example 75 steps 1 and 2] and methyl 4-amino-3-chlorobenzoate to obtain methyl 3-chloro-4-[(2-hydroxy-5-propylbenzene)amido]benzoate as an off-white solid. The initial crude solid was dissolved in dichloromethane, silica gel was added and the mixture was concentrated in vacuo. The residue was transferred to a pre-column and purified by chromatography using hexanes as eluent for one min. The eluent was then modified to 40% dichloromethane/hexanes over a 20 min. period and kept at 40% dichloromethane/hexanes for the remainder of the separation. The fractions containing the pure product were combined and concentrated in vacuo. NMR indicates an impurity that elutes with the product. Dissolved the solid in ethyl acetate and washed with 2×75 mL of 5% aqueous citric acid solution, then water, washed with 2×75 mL of 1N hydrogen chloride (aq) solution, then water. The organic phase was dried over sodium sulfate, filtered and concentrated in vacuo to give a 29.9% yield of methyl 3-chloro-4-[(2-hydroxy-5-propylbenzene)amido]benzoate as an off-white solid.

MS: m/z 346 (MH$^-$) and m/z 348 (MH$^+$).

$^1$H NMR (500 MHz, DMSO-$d_6$): δ 0.893 (t, 3H), 1.579 (q, 2H), 2.543 (t, 2H), 3.867 (s, 3H), 6.990 (m, 1H), 7.308 (d, 1H), 7.853 (s, 1H), 7.977 (m, 1H), 8.049 (s, 1H), 8.724 (d, 1H), 11.242 (s, 1H), 11.810 (s, 1H).

Example 76: 3-Chloro-4-[(2-hydroxy-5-propylbenzene)amido]benzoic acid

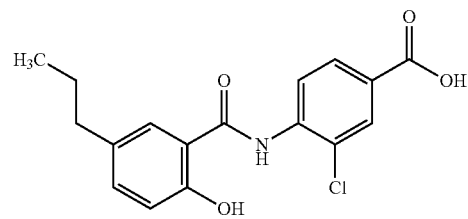 [SMILES: CCCc1ccc(O)c(C(=O)Nc2ccc(C(=O)O)cc2Cl)c1]

This compound was prepared in a similar manner as described in Example 2 substituting methyl 3-chloro-4-[(2-hydroxy-5-propylbenzene)amido]benzoate [Example 75] for methyl 3-chloro-4-{[2-hydroxy-5-(trifluoromethyl)benzene]amido}benzoate to give 3-chloro-4-[(2-hydroxy-5-propylbenzene)amido]benzoic acid as an off-white solid in a 96.3% yield.

MS: m/z 332 (MH$^-$).

$^1$H NMR (500 MHz, DMSO-$d_6$): δ 0.945 (t, 3H), 1.633 (qt, 2H) 2.596 (t, 2H), 7.040 (d, $^1$H), 7.359 (d, 1H), 7.907 (s, 1H), 8.003 (d, 1H), 8.074 (s, 1H), 8.741 (d, 1H), 11.2628 (s, 1H), 11.851 (s, 1H), 13.175 (br s, 1H).

Example 77: 5-Chloro-N-[2-chloro-4-(5-methyl-1,2,4-oxadiazol-3-yl)phenyl]-2-hydroxybenzamide

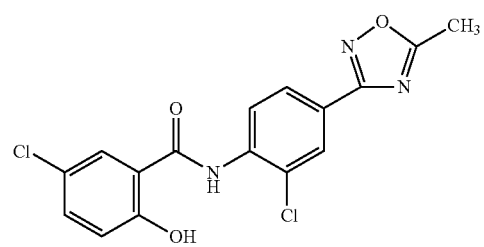 [SMILES: Cc1nc(-c2ccc(NC(=O)c3cc(Cl)ccc3O)c(Cl)c2)no1]

The synthetic route used to make this compound was adapted from the following published procedure: J. Med Chem., 37 (15), 2421-2436 (1994).

Step 1: 5-Chloro-N-{2-chloro-4-[N'-hydroxycarbaminidoyl]phenyl}-2-hydroxybenzamide

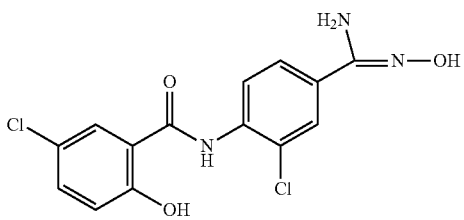 [SMILES: NC(=NO)c1ccc(NC(=O)c2cc(Cl)ccc2O)c(Cl)c1]

To a mixture of hydroxylamine hydrochloride (0.45 g, 6.5 mmol) and potassium carbonate (0.90 g, 6.5 mmol) in ethanol (10 mL) at ambient temperature was added 5-chloro-N-(2-chloro-4-cyanophenyl)-2-hydroxybenzamide (0.4 g, 1.3 mmol) [prepared as described in Example 28] in one portion and the mixture was heated at reflux for 21 hr. The hot reaction mixture was filtered and the solids were washed with ethanol. The combined filtrates were concentrated in vacuo to give the crude product as a yellow solid. LC/MS indicated 2 major components. The more prevalent component (approximately 65%) exhibited the mass for the desired product. [The impurity (approximately 35%) exhibited the mass of the primary amide of the starting nitrile.] This material was used without further purification.

MS: m/z 338 (MH$^-$) and m/z 340 (MH$^+$).

Step 2: 5-Chloro-N-[2-chloro-4-(5-methyl-1,2,4-oxadiazol-3-yl)phenyl]-2-hydroxybenzamide The solid from Step 1 was partially dissolved in pyridine (9 mL) and acetyl chloride (0.51 g, 6.5 mmol) was added dropwise rapidly. An exotherm was observed from ambient temperature to 65° C. The mixture was heated at reflux for 1 hr., cooled to ambient temperature, diluted with water and extracted twice with ethyl acetate. The organic phase was washed twice with water, then brine and dried over magnesium sulfate. The mixture was filtered and concentrated in vacuo to give 0.7 g of a dark orange oil. The residue was dissolved in ethyl acetate, silica gel was added and the mixture was concentrated in vacuo. The residue was transferred to pre-column and purified by chromatography using initially hexanes as eluent for 1 min. The eluent was then modified to 100% ethyl acetate over a 10 min. period and kept at 100% ethyl acetate for the remainder of the purification. Purification was not achieved. All fractions were combined and concentrated in vacuo. The residue was used without further purification.

The residue was dissolved in a mixture of ethanol (4 mL) and water (2 mL). To this mixture was added sodium hydroxide (2 mL of a 1M aqueous solution, 2.0 mmol) and the mixture was stirred at ambient temperature. After 5 hr, additional sodium hydroxide solution was added (3.2 mL, 3.2 mmol) and the mixture was stirred at ambient temperature overnight. Water (20 mL) was added to the reaction mixture and the mixture was acidified with 6N aqueous hydrogen chloride. The mixture was extracted several times with ethyl acetate. The combined organic phase was washed with water, then brine and dried over sodium sulfate. The mixture was filtered and concentrated in vacuo. The residue was dissolved in ethyl acetate, silica gel was added and the mixture was concentrated in vacuo. The residue was transferred to a pre-column and purified using initially hexanes as eluent for 1 min., then the eluent was modified to 25% ethyl acetate/hexanes over a 15 min. period, followed by immediately being modified to 50% ethyl acetate/hexanes over a 1 min. period. The eluent was kept at 50% ethyl acetate/hexanes for the remainder of the purification. The fractions containing the component with an R$_f$ of 0.53 (silica gel, 1:1 ethyl acetate/hexanes) were combined and concentrated in vacuo to give 0.153 g (32.3% yield) of 5-chloro-N-[2-chloro-4-(5-methyl-1,2,4-oxadiazol-3-yl)phenyl]-2-hydroxy benzamide as an off-white solid. This compound is approximately 90% pure.

MS: m/z 362 (MH$^-$).

$^1$H NMR (500 MHz, DMSO-d$_6$): δ 2.681 (s, 3H), 7.100 (d, 1H), 7.532 (dd, 1H), 7.989 (d, 1H), 8.019 (dd, 1H), 8.089 (d, 1H), 8.700 (d, 1H), 11.124 (s, 1H), 12.373 (s,

Example 78: Alternate Preparation of 5-tert-Butyl-N-(2-chloro-4-cyanophenyl)-2-hydroxybenzamide (see Example 53)

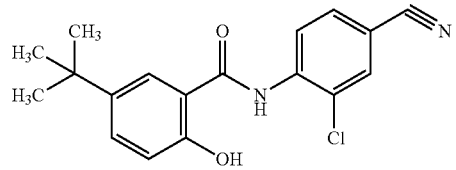 [SMILES: CC(C)(C)c1ccc(O)c(C(=O)Nc2ccc(C#N)cc2Cl)c1]

To a mixture of 5-tert-butylsalicylic acid (1.09 g, 5.6 mmol) [prepared as described in WO2005110996A1] and 4-amino-2-chloroaniline (0.86 g, 5.6 mmol) in xylenes (15 mL) at ambient temperature was added POCl$_3$ (0.25 g, 1.6 mmol) in one portion. The mixture was heated at 130° C. for 16.5 hr. After cooling to ambient temperature, the mixture was placed in an ice bath and stirred vigorously for 30 min. The resulting solid was washed once with ice-cold xylenes, then several times with hexanes and air dried. Obtained 0.92 g (50% yield) of 5-tert-butyl-N-(2-chloro-4-cyanophenyl)-2-hydroxybenzamide as an off-white solid. This material was used without further purification.

MS: m/z 327.1 (MH$^-$).

$^1$H NMR (500 MHz, DMSO-d$_6$): δ 1.286 (s, 9H), 7.014 (d, 1H), 7.542 (dd, 1H), 7.876 (dd, 1H), 8.038 (d, 1H), 8.177 (d, 1H), 8.758 (d, 1H), 11.291 (s, 1H).

Example 79: 5-tert-Butyl-N-[2-chloro-4-(2H-1,2,3,4-tetrazol-5-yl)phenyl]-2-hydroxybenzamide

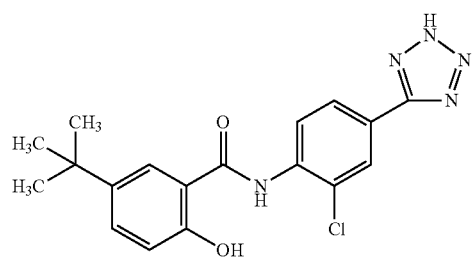 [SMILES: CC(C)(C)c1ccc(O)c(C(=O)Nc2ccc(-c3nn[nH]n3)cc2Cl)c1]

To a solution of ammonium chloride (0.06 g, 1.1 mmol) and sodium azide (0.07 g, 1.1 mmol) in dimethylformamide (5 mL) at ambient temperature was added in one portion 5-tert-butyl-N-(2-chloro-4-cyanophenyl)-2-hydroxybenzamide (0.4 g, 0.0 mmol) [prepared as described in Example 78]. The mixture was heated at 105° C. for 20.5 hr. The mixture was cooled to ambient temperature and the pH was adjusted to 1 by addition of a mixture of 1N HCl [aq] (5 mL) and water (5 mL). Added additional water (10 mL) and the mixture was stirred at ambient temperature for 1 hr. The resulting solid was filtered, washed with water and air dried. The crude material was dissolved in ethyl acetate, silica gel was added and the mixture was concentrated in vacuo. The residue was transferred to a pre-column and purified by chromatography using initially hexanes (1 min.) as eluent. The eluent was modified to 60% ethyl acetate/hexanes over a 20 min. period and held at 60% ethyl acetate/hexanes for the remainder of the purification. The fractions containing the pure desired product were combined and concentrated in vacuo to give 87.2 mgs (27.4% yield) of 5-tert-butyl-N-[2-chloro-4-(2H-1,2,3,4-tetrazol-5-yl)phenyl]-2-hydroxybenzamide as an off-white solid.

MS: m/z 370.1 (MH$^-$) and m/z 372.1 (MH$^+$).

$^1$H NMR (500 MHz, DMSO-d$_6$): δ 1.296 (s, 9H), 7.017 (d, 1H), 7.537 (dd, 1H), 8.053 (d, 1H), 8.068 (m, 1H), 8.202 (d, 1H), 8.760 (d, 1H), 11.186 (s, 1H), 11.823 (s, 1H).

Example 80: Alternate preparation of Methyl 4-[(5-tert-butyl-2-hydroxybenzene)amido]-3-chlorobenzoate (See Example 3)

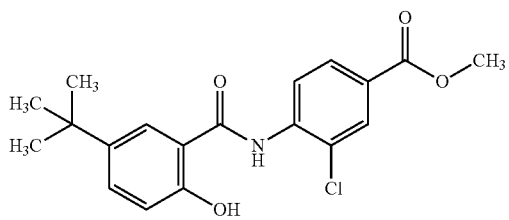 [SMILES: COC(=O)c1ccc(NC(=O)c2cc(C(C)(C)C)ccc2O)c(Cl)c1]

To a mixture of 4-[(5-tert-butyl-2-hydroxybenzene)amido]-3-chlorobenzoic acid (0.5 g, 1.4 mmol) [Example 4] in methanol (10 mL) was added concentrated sulfuric acid (0.05 mL) in one portion via syringe. The mixture was heated at reflux for two days. The mixture was homogeneous but thin layer chromatography still indicated starting material present. Concentrated sulfuric acid (3 drops) was added and the mixture was refluxed for 4 hr. The mixture was cooled to ambient temperature and poured into a separatory funnel containing a mixture of ethyl acetate and water. The phases were separated and the organic phase was washed with 2×100 mL of saturated sodium bicarbonate (aq), then 2×100 mL of brine and dried over sodium sulfate. The mixture was filtered and concentrated in vacuo to give 0.47 g (92.2% yield) of methyl 4-[(5-tert-butyl-2-hydroxybenzene)amido]-3-chlorobenzoate as an off-white solid.

MS: m/z 360.0 (MH$^-$) and m/z 362.0 (MH$^+$).

$^1$H NMR (500 MHz, DMSO-d$_6$): δ 1.290 (s, 9H), 3.68 (s, 3H), 7.013 (d, 1H), 7.535 (dd, 1H), 7.977 (dd, 1H), 8.052 (br d, 2H), 8.731 (d, 1H), 11.238 (s, 1H), 11.831 (s, 1H).

Example 81: 5-tert-Butyl-N-(2-chloro-4-iodophenyl)-2-hydroxybenzamide

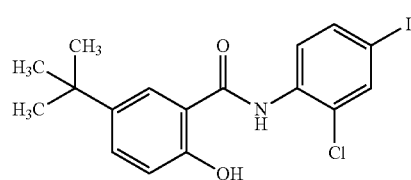 [SMILES: CC(C)(C)c1ccc(O)c(C(=O)Nc2ccc(I)cc2Cl)c1]

5-tert-butyl-N-(2-chloro-4-iodophenyl)-2-hydroxybenzamide

This compound was prepared in a similar manner as described in Example 1, step 3 from 5-tert-butyl-2-hydroxybenzoic acid and 2-chloro-4-iodoaniline [ACROS Organics] to obtain 5-tert-butyl-N-(2-chloro-4-iodophenyl)-2-hydroxy benzamide. The cooled reaction mixture was dissolved in ethyl acetate and washed with 2×50 mL of saturated aqueous sodium bicarbonate, 2×50 mL of 1N HCl (aq) and brine. Silica gel was added to the organic phase and the mixture was concentrated in vacuo. The residue was transferred to a pre-column and purified by chromatography using a gradient as follows: initially hexane for 1 min., then the eluent was modified to 15% ethyl acetate/hexane over a 20 min. period and kept at 15% ethyl acetate/hexane for the remainder of the separation. The fractions containing the pure major component were combined and concentrated in vacuo to give 5-tert-butyl-N-(2-chloro-4-iodophenyl)-2-hydroxy benzamide as an off-white solid in a 68.7% yield.

MS: m/z 427.9 (MH$^-$) and m/z 429.9 (MH$^+$).

$^1$H NMR (500 MHz, DMSO-d$_6$): δ 1.282 (s, 9H), 6.981 (d, 1H), 7.509 (dd, 1H), 7.730 (dd, 1H), 7.925 (d, 1H), 8.025 (d, 1H), 8.264 (d, 1H), 10.951 (s, 1H), 11.747 (s, 1H).

Example 82: 5-tert-Butyl-N-[2-chloro-4-(5-methyl-1,2,4-oxadiazol-3-yl)phenyl]-2-hydroxybenzamide

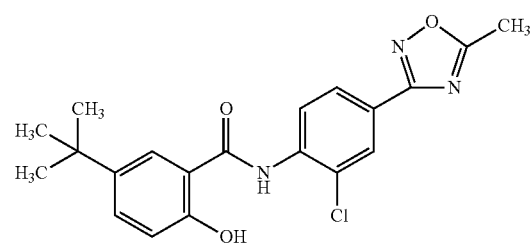 [SMILES: Cc1nc(-c2ccc(NC(=O)c3cc(C(C)(C)C)ccc3O)c(Cl)c2)no1]

This compound was prepared in similar manner as described in Example 77 with minor modifications as follows:

Step 1: 5-tert-Butyl-N-{2-chloro-4-[N'-hydroxycarbaminidoyl]phenyl}-2-hydroxybenzamide

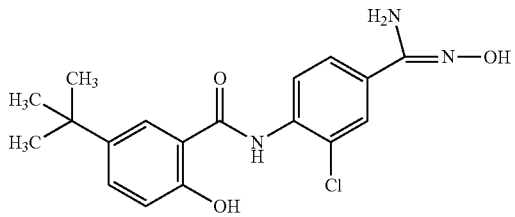 [SMILES: CC(C)(C)c1ccc(O)c(C(=O)Nc2ccc(C(N)=NO)cc2Cl)c1]

To a mixture of hydroxylamine hydrochloride (0.49 g, 7.0 mmol) and potassium carbonate (0.97 g, 7.0 mmol) in ethanol (10 mL) at ambient temperature was added 5-tert-Butyl-N-(2-chloro-4-cyanophenyl)-2-hydroxybenzamide (0.45 g, 1.4 mmol) [prepared as described in Example 78] in one portion and the mixture was heated at reflux for 24 hr. The hot reaction mixture was filtered and the solids were washed with ethanol. The combined filtrates were concentrated in vacuo to give 0.52 g of the crude product as a yellow solid. LC/MS indicated 2 major components. The more prevalent component exhibited the mass for the desired product. This material was used without further purification.

MS: m/z 360.1 (MH$^-$) and m/z 362.1 (MH$^+$).

Step 2: 5-tert-Butyl-N-[2-chloro-4-(5-methyl-1,2,4-oxadiazol-3-yl)phenyl]-2-hydroxybenzamide The solid from Step 1 was dissolved in pyridine (10 mL) and acetyl chloride (0.55 g, 7.0 mmol) was added dropwise rapidly. The reaction mixture exothermed from ambient temperature to 36.7° C. The mixture was heated at reflux for 1 hr., cooled to ambient temperature, diluted with water and extracted twice with ethyl acetate. The organic phase was washed with water, then brine and dried over magnesium sulfate. The mixture was filtered and concentrated in vacuo. The residue was dissolved in ethyl acetate, silica gel was added and the mixture was concentrated in vacuo. The residue was transferred to pre-column and purified using initially hexanes as eluent. The eluent was modified to 100% ethyl acetate over a 10 min. period and kept at 100% ethyl acetate for the remainder of the purification. Purification was not achieved. All fractions were combined and concentrated in vacuo. The residue was used without further purification. The residue was partially dissolved in a mixture of ethanol (5 mL) and water (2.5 mL). To this mixture was added sodium hydroxide (5 mL of a 1M aqueous solution, 5.0 mmol) and the mixture was stirred at ambient temperature for 21 hr. Water (20 mL) was added to the reaction mixture and the mixture was acidified with 6N aqueous hydrogen chloride to a pH of 2. The mixture was extracted several times with ethyl acetate. The combined organic phase was washed with water, then brine and dried over sodium sulfate. The mixture was filtered and concentrated in vacuo. The residue was dissolved in ethyl acetate, silica gel was added and the mixture was concentrated in vacuo. The residue was transferred to a pre-column and purified using initially hexanes as eluent for 1 min., then the eluent was modified to 35% ethyl acetate/hexanes over a 12 min. period and the eluent was kept at 35% ethyl acetate/hexanes for the remainder of the purification. Combined the fractions containing the component with an $R_f$ of 0.69 (silica gel, 1:1 ethyl acetate/hexanes) and concentrated in vacuo to give 0.196 g (36.3% yield) of 5-tert-butyl-N-[2-chloro-4-(5-methyl-1,2,4-oxadiazol-3-yl)phenyl]-2-hydroxy benzamide as a white solid. Compound is approximately 94% pure.

MS: m/z 384.1 (MH$^-$) and m/z 386.1 (MH$^+$).

$^1$H NMR (500 MHz, DMSO-d$_6$): δ 1.293 (s, 9H), 2.676 (s, 3H), 7.011 (d, 1H), 7.531 (dd, 1H), 8.010 (dd, 1H), 8.059 (d, 1H), 8.085 (d, 1H), 8.735 (d, 1H), 11.180 (s, 1H), 11.812 (s, 1H).

Example 83: 5-tert-Butyl-N-[2-chloro-4-(5-methyl-4H-1,2,4-triazol-3yl)phenyl]-2-hydroxybenzamide

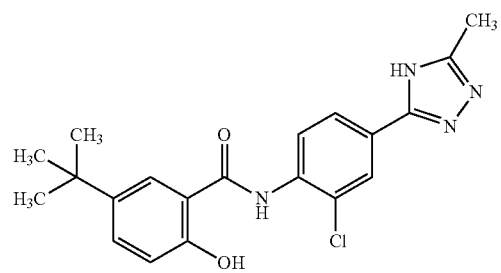 [SMILES: Cc1nnc(-c2ccc(NC(=O)c3cc(C(C)(C)C)ccc3O)c(Cl)c2)[nH]1]

To a screw cap vial was added 5-tert-Butyl-N-(2-chloro-4-cyanophenyl)-2-hydroxybenzamide [prepared as described in Example 78](0.150 g, 0.46 mmol), acetamidine HCl (0.06 g, 0.68 mmol), cesium carbonate (0.46 g, 1.4 mmol) and copper bromide (2.9 mgs, 0.02 mmol). Dimethylsulfoxide (1.2 mL) was added and the vial was sealed and heated at 120° C. for 22.5 hr. After cooling to ambient temperature, the reaction mixture was diluted with ethyl acetate (~100 mL) and washed with 2×75 mL of saturated aqueous sodium bicarbonate solution, then 2×75 mL of brine and dried over sodium sulfate. The mixture was filtered and concentrated in vacuo to give 0.125 g of a yellow glass. The residue was dissolved in ethyl acetate, silica gel was added and the mixture was concentrated in vacuo. The residue was transferred to a pre-column and purified using initially hexanes (2 min.) as eluent. The eluent was modified to Ethyl acetate/hexanes (1:1) over an 8 min period and kept at ethyl acetate/hexanes (1:1) for the remainder of the purification. Combined the fractions containing the pure desired component and concentrated in vacuo to get 35.1 mgs of an off-white solid. LC/MS shows a minor impurity that does not show on TLC. Dissolved the solid in dichloromethane, added silica gel and concentrated in vacuo. Transferred to a pre-column and rechromatographed using a 12 g column and initially dichloromethane (~15 min) as eluent. Modified the eluent to methanol/dichloromethane (2:98) over 1 min period and kept the eluent at methanol/dichloromethane (2:98) for the remainder of the purification. Combined the fractions containing the pure component with the correct mass as indicated by LC/MS and concentrated in vacuo to get 22.5 mgs (12.7%) of 5-tert-Butyl-N-[2-chloro-4-(5-methyl-4H-1,2,4-triazol-3yl)phenyl]-2-hydroxybenzamide as a white solid.

MS: m/z 383.1 (MH$^-$) and m/z 385.1 (MH$^+$).

$^1$H NMR (500 MHz, DMSO-d$_6$): δ 1.287 (s, 9H), 2.409 (s, 3H), 6.990 (d, 1H), 7.510 (dd, 1H), 7.959 (dd, 1H), 8.050 (m, 2H), 8.542 (d, 1H), 11.011 (s, 1H), 11.751 (s, 1H), 13.727 (s, 1H).

Example 84: Methyl 4-[(5-tert-butyl-2-methoxybenzene)amido]-3-chlorobenzoate

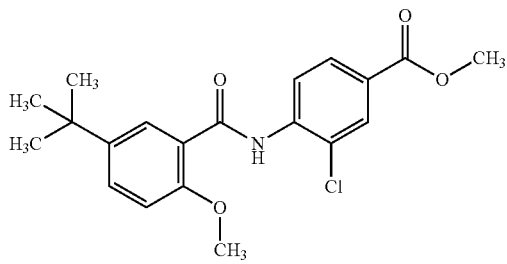 [SMILES: COC(=O)c1ccc(NC(=O)c2cc(C(C)(C)C)ccc2OC)c(Cl)c1]

To a heterogenous mixture of methyl 4-[(5-tert-butyl-2-hydroxybenzene)amido]-3-chlorobenzoate [Example 80] (0.47 g, 1.3 mmol) in acetonitrile (5 ml) was added cesium carbonate (0.54 g, 1.7 mmol) in one portion and the mixture was stirred a ambient temperature for 30 min. Methyl iodide (0.40 g, 2.8 mmol, 0.18 mL) was added dropwise rapidly via syringe and the resulting mixture was stirred at ambient temperature overnight. The reaction mixture was poured into a mixture of ethyl acetate and water, the phases were separated and the organic phase was washed with water and brine. The organic phase was dried over sodium sulfate, filtered and concentrated in vacuo to give a brown gooey solid. The crude product was taken up into ethyl acetate, silica gel was added and the mixture was concentrated in vacuo. The residue was transferred to a pre-column and purified by column chromatography using initially hexanes (1 min.) as eluent. The eluent was modified to 10% ethyl acetate/hexanes over a 15 min. period and held at 10% ethyl acetate/hexanes for the remainder of the purification. The fractions containing the pure major component (determined by TLC) were combined and concentrated in vacuo to give an off-white solid. Combined the fractions containing the major component plus an impurity and concentrated in vacuo. Rechromatographed as above using the following gradient: initially hexanes (1 min.), then modified the eluent to 10% ethyl acetate/hexanes over a 5 min period, held the eluent at 10% ethyl acetate/hexanes for the remainder of the purification. Combined the fractions containing the pure major component with the pure material obtained from the first purification and concentrated in vacuo to get a total of 0.307 g (62.8%) of methyl 4-[(5-tert-butyl-2-methoxybenzene)amido]-3-chlorobenzoate as an off-white solid. LC/MS shows one peak, NMR shows a minor impurity. Used this material without further purification.

MS: m/z 376.1 (MH$^+$).

$^1$H NMR (500 MHz, DMSO-d$_6$): δ 1.305 (s, 9H), 3.860 (s, 3H), 4.084 (s, 3H), 7.256 (d, 1H), 7.677 (dd, 1H), 7.973 (dd, 1H), 8.059 (d, 1H), 8.110 (d, 1H), 8.720 (d, 1H), 10.877 (s, 1H).

Example 85: 4-[(5-tert-Butyl-2-methoxybenzene)amido]-3-chlorobenzoic acid

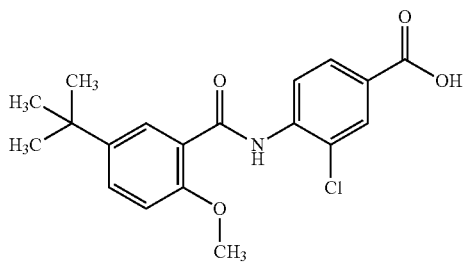 [SMILES: COc1ccc(C(C)(C)C)cc1C(=O)Nc1ccc(C(=O)O)cc1Cl]

A mixture of methyl 4-[(5-tert-butyl-2-methoxybenzene)amido]-3-chlorobenzoate [Example 84] (0.17 g, 0.45 mmol) suspended in aqueous sodium hydroxide (1 mL of a 1M solution) was heated at 60° C. for 1.5 hr. Ethanol (1 mL) was added to improve solubility. After 3 hr at reflux, ethanol (2 mL) was added and the mixture was heated at 60° C. overnight. The homogeneous solution was cooled to ambient temperature, diluted with water (25 mL), chilled in an ice bath and made acidic by addition of 1N aqueous hydrochloric acid (10 mL). After stirring in the ice bath for 30 min., the resulting solid was filtered, washed with water and air dried for 5 hr. to give 0.142 g (87.1%) of 4-[(5-tert-butyl-2-methoxybenzene)amido]-3-chlorobenzoic acid as white solid.

MS: m/z 362.1 (MH$^+$).

$^1$H NMR (500 MHz, DMSO-d$_6$): δ 1.258 (s, 9H), 4.035 (s, 3H), 7.206 (d, 1H), 7.626 (dd, 1H) 7.898 (br dd, 1H), 7.978 (d, 1H), 8.064 (d, 1H), 8.644 (d, 1H), 10.806 (s, 1H), 13.082 (s, 1H).

Example 86: Methyl 4-[(5-tert-butyl-2-hydroxybenzene)amido]-3,5-dichlorobenzoate

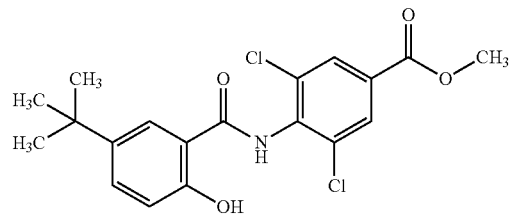 [SMILES: COC(=O)c1cc(Cl)c(NC(=O)c2cc(C(C)(C)C)ccc2O)c(Cl)c1]

Step 1: Methyl 4-amino-3,5-dichlorobenzoate

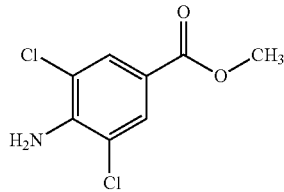

Thionyl chloride (2.14 g, 0.018 mol) was added dropwise to methanol (10 mL) at −3-4° C. via a syringe keeping the temperature at or below −1.1° C. over a 35 min. period. The resulting mixture was stirred at or below 0° C. for 1 hr., then 4-amino-3,5-dichloro benzoic acid (0.75 g, 3.6 mmol) [ACROS Organics] was added in one portion. The reaction mixture was stirred at ambient temperature for ~3 days after which the homogeneous mixture was concentrated in vacuo. Water (6 mL) was added to the residue and sodium bicarbonate (0.36 g, 4.3 mmol) was added in one portion and the mixture was stirred at ambient temperature for 30 min. The mixture was extracted several times with ethyl acetate. The combined organic phase was dried over sodium sulfate, filtered and concentrated in vacuo to give 0.79 g (quantitative yield) of methyl 4-amino-3,5-dichlorobenzoate as a tan solid.

MS: m/z 220 (MH$^+$).

$^1$H NMR (500 MHz, DMSO-d$_6$): δ 3.780 (s, 3H), 6.407 (br s, 2H), 7.731 (s, 2H).

Step 2: Methyl 4-[(5-tert-butyl-2-hydroxybenzene)amido]-3,5-dichlorobenzoate

This compound was prepared in a similar manner as described in Example 1, step 3 from 5-tert-butyl-2-hydroxybenzoic acid [prepared as described in WO2005110996A1] and methyl 4-amino-3,5-dichlorobenzoate (Example 86, step 1) to obtain methyl 4-[(5-tert-butyl-2-hydroxybenzene)amido]-3,5-dichlorobenzoate. The cooled reaction mixture was dissolved in ethyl acetate and washed with saturated aqueous sodium bicarbonate solution, 1N aqueous hydrogen chloride solution and brine, silica gel was added to the organic phase and the mixture was concentrated in vacuo. The residue was transferred to a pre-column and purified by chromatography using a gradient as follows: initially hexane for 2 min., then the eluent was modified to 10% ethyl acetate/hexane over an 18 min, period and kept at 10% ethyl acetate/hexane for the remainder of the separation. Combined the fractions containing material with the desired mass as shown by LC/MS and concentrated in vacuo to give a glass. To the residue was added hexanes (10-15 mL), followed by six drops of dichloromethane. The mixture was triturated at ambient temperature. The resulting solid was filtered and washed with hexanes to give 10.3 rags (1.7%) of methyl 4-[(5-tert-butyl-2-hydroxybenzene)amido]-3,5-dichlorobenzoate as a white solid.

MS: m/z 394 (MH$^-$) and m/z 396 (MH$^+$).

$^1$H NMR (500 MHz, DMSO-d$_6$): δ 1.305 (s, 9H), 3.915 (s, 3H), 6.957 (d, 1H), 7.553 (dd, 1H), 8.003 (d, 1H), 8.074 (br s, 2H), 10.629 (br s, 1H), 11.665 (s, 1H).

Example 87: Methyl 3-chloro-4-{[2-hydroxy-5-(2-methylbutan-2-yl)benzene]amido}benzoate

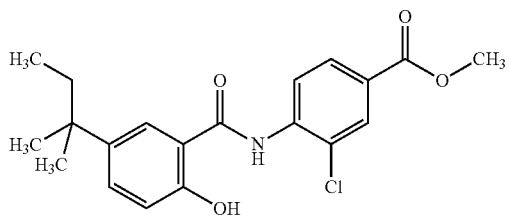 [SMILES: CCC(C)(C)c1ccc(O)c(C(=O)Nc2ccc(C(=O)OC)cc2Cl)c1]

Step 1:
2-Hydroxy-5-(2-methylbutan-2-yl)benzaldehyde

This compound was prepared in a similar manner as described in Example 1, step 1 by substituting 4-tert-amylphenol [ACROS Organics] for 4-trifluoromethyl phenol except for column chromatography. The crude product was purified using hexane as eluent. The fractions containing the pure product were concentrated in vacuo to give a 64.7% yield of 2-hydroxy-5-(2-methylbutan-2-yl)benzaldehyde as a yellow oil.

MS: m/z 193.1 (MH$^+$).

$^1$H NMR (500 MHz, DMSO-d$_6$): δ 0.615 (t, 3H), 1.223 (s, 6H), 1.581 (q, 2H), 6.947 (d, 1H), 7.525 (dd, 1H), 7.583 (d, 1H), 10.240 (s, 1H), 10.525 (s, 1H).

Step 2: 2-Hydroxy-5-(2-methylbutan-2-yl)benzoic acid

This compound was prepared in a similar manner as described in Example 1, step 2 substituting 2-hydroxy-5-(2-methylbutan-2-yl)benzaldehyde (Example 87, step 1) for 2-hydroxy-5-(trifluoromethyl)benzaldehyde. To the crude ethyl acetate solution after drying with magnesium sulfate was added silica gel and the mixture was concentrated in vacuo. The residue was transferred to a pre-column and purified by chromatography using initially hexanes as eluent for 4 min., then the eluent was modified to 10% ethyl acetate/hexanes over a 5 min. period and kept at 10% ethyl acetate/hexanes for the remainder of the purification. The fractions containing the pure desired product were combined and concentrated in vacuo to give a 37.4% yield of 2-hydroxy-5-(2-methylbutan-2-yl)benzoic acid as a pinkish white solid.

MS: m/z 207.1 (MH$^-$).

$^1$H NMR (500 MHz, DMSO-d$_6$): δ 0.615 (t, 3H), 1.220 (s, 6H), 1.581 (q, 2H), 6.901 (d, 1H), 7.509 (dd, 1H), 7.691 (d, 1H), 11.121 (br s, 1H), 13.883 (br s, 1H).

Step 3: Methyl 3-chloro-4-{[2-hydroxy-5-(2-methylbutan-2-yl)benzene]amido}-3-chlorobenzoate This compound was prepared in a similar manner as described in Example 1, step 3 from 2-hydroxy-(2-methylbutan-2-yl)benzoic acid [prepared as described in WO2005110996A1, Example 87 steps 1 and 2] and methyl 4-amino-3-chlorobenzoate to obtain methyl 3-chloro-4-{[2-hydroxy-5-(2-methylbutan-2-yl)benzene]amido}benzoate except the initial solid filtered from the cooled reaction mixture did not need further purification. The product was obtained in two crops of crystals totaling a 39.3% yield as a white solid. The MS and NMR data are reported for the first crop of crystals.

MS: m/z 374.1 (MH$^-$) and m/z 376.1 (MH$^+$).

$^1$H NMR (500 MHz, DMSO-d$_6$): δ 0.633 (t, 3H), 1.251 (s, 6H), 1.609 (q, 2H), 3.867 (s, 3H), 7.016 (d, 1H), 7.470 (dd, 1H), 7.980 (m, 2H), 8.053 (m, 1H), 8.732 (d, 1H), 11.242 (s, 1H), 11.831 (s, 1H).

Example 88: 3-Chloro-4-{[2-hydroxy-5-(2-methylbutan-2-yl)benzene]amido}benzoic acid

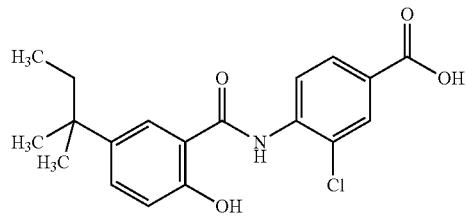 [SMILES: CCC(C)(C)c1ccc(O)c(C(=O)Nc2ccc(C(=O)O)cc2Cl)c1]

This compound was prepared in a similar manner as described in Example 2 substituting methyl 3-chloro-4-{[2-hydroxy-5-(2-methylbutan-2-yl)benzene]amido}benzoate [Example 87] for methyl 3-chloro-4-{[2-hydroxy-5-(trifluoromethyl)benzene]amido}benzoate to give 3-chloro-4-{[2-hydroxy-5-(2-methylbutan-2-yl)benzene]amido}benzoic acid as a beige solid in a 92.5% yield.

MS: m/z 360.1 (MH$^-$) and m/z 362.1 (MH$^+$).

$^1$H NMR (500 MHz, DMSO-d$_6$): δ 0.635 (t, 3H), 1.253 (s, 6H), 1.611 (qt, 2H), 7.015 (d, 1H), 7.464 (dd, 1H), 7.947 (dd, 1H), 7.995 (d, 1H), 8.023 (d, 1H), 8.698 (d, 1H), 11.220 (s, 1H), 11.821 (br s, 1H), 13.092 (br s, 1H).

Example 89: Methyl 3-chloro-4-(3-hydroxynaphthalene-2-amido)benzoate

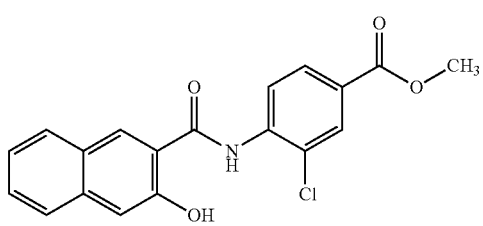 [SMILES: COC(=O)c1ccc(NC(=O)c2cc3ccccc3cc2O)c(Cl)c1]

Methyl 3-chloro-4-(3-hydroxynaphthalene-2-amido)benzoate

This compound was prepared in a similar manner as described in Example 1, step 3 from 3-hydroxy-2-naphthoic acid [ACROS Organics] and methyl 4-amino-3-chlorobenzoate to obtain methyl 3-chloro-4-(3-hydroxynaphthalene-2-amido)benzoate except the initial solid filtered from the cooled reaction mixture gave a 79.6% yield of a light pink solid that did not need further purification.

MS: m/z 354 (MH$^-$) and m/z 356 (MH$^+$).

$^1$H NMR (500 MHz, DMSO-d$_6$): δ 3.879 (s, 3H), 7.394 (m, 2H), 7.556 (m, 1H), 7.805 (d, 1H), 8.019 (m, 2H), 8.079 (d, 1H), 8.741 (s, 1H), 8.791 (d, 1H), 11.463 (s, 1H), 12.096 (s, 1H).

Example 90: 3-Chloro-4-(3-hydroxynaphthalene-2-amido)benzoic acid

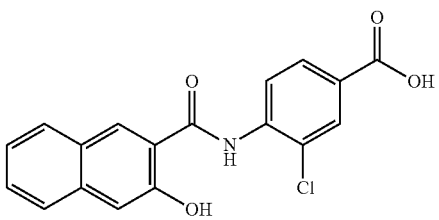 [SMILES: O=C(O)c1ccc(NC(=O)c2cc3ccccc3cc2O)c(Cl)c1]

This compound was prepared in a similar manner as described in Example 2 substituting methyl 3-chloro-4-(3-hydroxynaphthalene-2-amido)benzoate [Example 89] for methyl 3-chloro-4-{[2-hydroxy-5-(trifluoromethyl)benzene]amido}benzoate to give 3-chloro-4-(3-hydroxynaphthalene-2-amido)benzoic acid as a tan solid in a quantitative yield.

MS: m/z 340 (MH$^-$) and m/z 342 (MH$^+$).

$^1$H NMR (500 MHz, DMSO-d$_6$): δ 7.385 (m, 1H), 7.406 (s, 1H), 7.553 (m, 1H), 7.803 (d, 1H), 7.988 (dd, 1H), 8.024 (d, 1H), 8.050 (d, 1H), 8.755 (m, 2H), 11.435 (s, 1H), 12.080 (s, 1H), 13.141 (br s, 1H).

Example 91: Methyl 3-chloro-4-{[2-hydroxy-5-(morpholin-4-yl)benzene]amido}benzoate

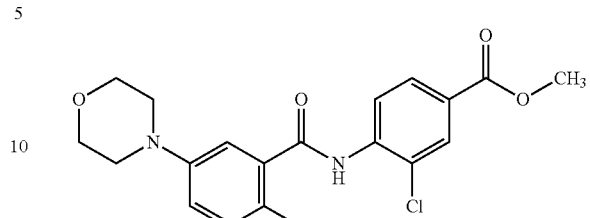

Step 1: Methyl 5-amino-2-hydroxybenzoate

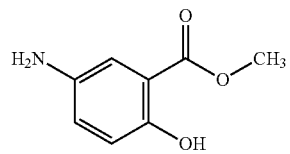

This compound was prepared as described in J. Med. Chem., 76, 5873-5881 (2011) as follows: To a heterogeneous mixture of 5-aminosalicylic acid (2.0 g, 0.013 mol) [ACROS Organics] in methanol (30 mL) was added concentrated sulfuric acid (2.9 mL) dropwise. An exotherm was observed and the resulting homogeneous solution was heated at 65° C. for 16.25 hr. After cooling to ambient temperature, the volume was reduced to ¼ its original size and the pH was adjusted to 7-8 by addition of saturated aqueous sodium bicarbonate solution. The resulting solid was filtered, washed with water and air dried to give 1.59 g (73.3%) of methyl 5-amino-2-hydroxybenzoate as an off-white solid.

MS: m/z 168.1 (MH$^+$).

Step 2: Methyl 2-hydroxy-5-(morpholin-4-yl)benzoate

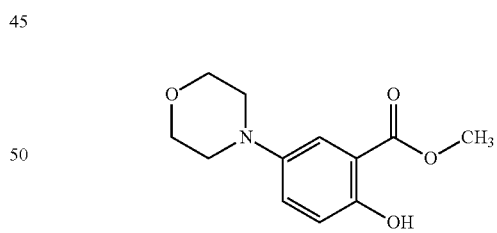

This compound was prepared in a similar manner as described in WO 02/20500 A2 as follows:

To the methyl 5-amino-2-hydroxybenzoate (1.0 g, 0.006 mol) in toluene (10 mL) was added diisopropylethylamine (1.55 g, 0.012 mol), 2-chloroethylether (0.86 g, 0.006 mol) and sodium iodide (1.80 g, 0.012 mol) each in one portion. The mixture was heated at reflux for 3 days. After cooling to ambient temperature, the reaction was quenched by addition of 20 mL of 0.5M aqueous citric acid solution. The resulting mixture was extracted with ethyl acetate (3×80 mL). The combined organic phase was washed with saturated aqueous sodium bicarbonate solution, then brine and dried over sodium sulfate. The mixture was filtered, silica gel was added to the filtrate and the mixture was evaporated to dryness in vacuo. The residue was transferred to a pre-column and purified by chromatography using initially hexanes (1 min.) as eluent. The eluent was then modified to 20% ethyl acetate/hexanes over a 10 min period and kept at 20% ethyl acetate/hexanes for the remainder of the purification. The fractions containing the pure major component were combined and concentrated in vacuo to give 0.393 g (27.7%) of methyl 2-hydroxy-5-(morpholin-4-yl)benzoate as a viscous yellow oil.

MS: m/z 238.1 (M$^+$)

$^1$H NMR (500 MHz, CDCl$_3$): δ 3.057 (m, 4H), 3.866 (m, 4H), 3.952 (s, 3H), 6.942 (d, 1H), 7.161 (dd, 1H), 7.339 (d, 1H), 10.370 (s, 1H).

Step 3: 2-Hydroxy-5-(morpholin-4-yl)benzoic acid

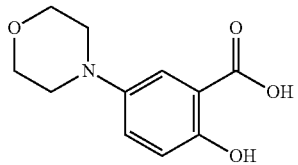 [SMILES: O=C(O)c1cc(N2CCOCC2)ccc1O]

This compound was prepared in a similar manner as described in WO 02/20500 A2 as follows: A mixture of methyl 2-hydroxy-5-(morpholin-4-yl)benzoate (0.39 g, 1.6 mmol) and LiOH (0.19 g, 8.0 mmol) in methanol (10 mL) and water (5 mL) was heated at 66° C. for 17 hr. After cooling to ambient temperature the reaction mixture was partitioned between ethyl acetate and water. The pH of the aqueous phase was adjusted to 4 with 1N aqueous hydrogen chloride. Concentrated the solution to dryness in vacuo and triturated the residue with MeOH-no crystals. Concentrated in vacuo. Dissolved the residue in MeOH, added silica gel and concentrated in vacuo. Transferred the residue to a pre-column and purified by chromatography using initially dichloromethane (5 min.) as eluent. The eluent was then modified to 10% MeOH/dichloromethane over a 5 min. period and kept at 10% MeOH/dichloromethane for the remainder of the purification. The fractions containing the pure major component was concentrated in vacuo to give 0.31 g (86.8%) of 2-hydroxy-5-(morpholin-4-yl)benzoic acid as an orange glass.

MS: m/z 222.1 (M$^-$) and m/z 224.1 (M$^+$)

$^1$H NMR (500 MHz, DMSO-d$_4$): δ 2.983 (m, 4H), 3.729 (m, 4H), 6.851 (d, 1H), 7.221 (dd, 1H), 7.253 (d, 1H).

The COOH and OH signals apparently are with the water signal at δ3.319.

Step 4: Methyl 3-chloro-4-{[2-hydroxy-5-(morpholin-4-yl)benzene]amido}benzoate

This compound was prepared in a similar manner as described in Example 1, step 3 using 2-hydroxy-5-(morpholin-4-yl)benzoic acid in place of 2-hydroxy-5-(trifluoromethyl)benzoic acid to obtain methyl 3-chloro-4-{[2-hydroxy-5-(morpholin-4-yl)benzene]amido}benzoate as a brown solid in a 5.5% yield. The solid filtered from the hot reaction mixture contained one impurity (the starting benzoic acid). Added ethyl acetate to the cooled filtrate, added silica gel and concentrated in vacuo. Transferred the residue to a pre-column and purified by chromatography using ethyl acetate as eluent. Complete separation was not achieved. Combined the fractions containing the major component plus impurity and concentrated in vacuo. Dissolved the residue in ethyl acetate, added silica gel and concentrated in vacuo. Transferred to a pre-column and purified by chromatography using initially hexanes (3 min.) as eluent. The eluent was modified to 30% ethyl acetate/hexanes over a 6 min. period and kept at 30% ethyl acetate/hexanes for the remainder of the purification. Combined the fractions containing the pure component at R$_f$=0.08 (30% ethyl acetate/hexanes) and concentrated in vacuo to give a 5.5% yield MS: m/z 389.1 (MH$^-$) and m/z 391 (MH$^+$).

$^1$H NMR (500 MHz, DMSO-d$_6$): δ 3.033 (m, 4H), 3.754 (m, 4H), 3.869 (s, 3H), 6.992 (d, 1H), 7.193 (dd, 1H), 7.557 (d, 1H), 7.978 (dd, 1H), 8.052 (d, 1H), 8.725 (d, 1H), 11.306 (s, 1H), 11.512 (s, 1H).

Example 92: Methyl 3-chloro-4-[(3,5-di-tert-butyl-2-hydroxybenzene)amido]benzoate

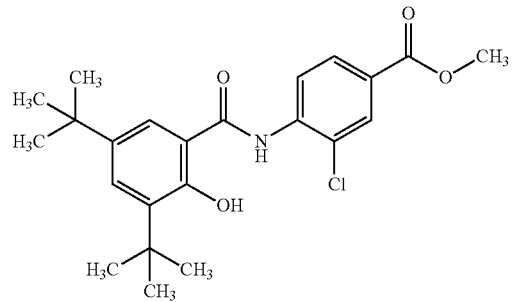 [SMILES: COC(=O)c1ccc(NC(=O)c2cc(C(C)(C)C)cc(C(C)(C)C)c2O)c(Cl)c1]

Step 1: Methyl 3,5-di-tert-butylsalicylate and Methyl 5-tert-butylsalicylate

This compound was prepared as described in Synthetic Communications, 37 (14), 2391-2397, (2007) with some modifications as follows: To a solution of methyl salicylate (5.0 g, 0.033 mol) and tert-butanol (6.2 g, 0.083 mol) in Methanol (3.3 mL) at −3.4° C. was added slowly dropwise concentrated sulfuric acid (11.6 mL) at such a rate as to keep the temperature below 7° C. The resulting mixture was stirred at ambient temperature for 5 h. No solid formed as described in the literature. Water (250 mL) was added to the reaction mixture and the mixture was stirred at ambient temperature for 2.5 days. A white gooey material surrounding the stir bar was obtained. Decanted off the aqueous solution and washed the gooey material twice with water decanting off the aqueous phase each time. Dissolved the gooey material in ethyl acetate and washed with brine, then dried over sodium sulfate. Filtered and concentrated the filtrate in vacuo. Dissolved the residue in ethyl acetate, added silica gel and concentrated in vacuo. Transferred the residue to a pre-column and purified by chromatography using a 24 g column and hexanes as eluent. Obtained three components: Component 1 was obtained by combining the fractions containing the pure faster running material and concentrating in vacuo to obtain 4.39 g of a colorless oil. Component 2 was obtained by combining the fractions containing the pure slower running material and concentrating in vacuo to give 0.29 g of a colorless oil. Component 3 was obtained by combining the fractions containing both materials and concentrating in vacuo to give 2.09 g of a colorless oil. Component 3 was rechromatographed as described above. The fractions containing the pure faster running material was combined with Component 1 above and concentrated in vacuo to give 5.5 g (63.2%) of the desired product methyl 3,5-di-tert-butylsalicylate as a colorless oil that solidified on cooling to a white solid.

MS: m/z 265.1 (MH$^+$).

$^1$H NMR (500 MHz, CDCl$_3$): δ 1.305 (s, 9H), 1.425 (s, 9H), 3.936 (s, 3H), 7.521 (d, 1H), 7.706 (d, 1H), 11.338 (s, 1H).

The fractions containing the slower running material were combined with Component 2 above and concentrated in vacuo to obtain 0.97 g of methyl 5-tert-butylsalicylate as a colorless oil.

MS: m/z 209.1 (MH$^+$).

$^1$H NMR (500 MHz, CDCl$_3$): δ 1.302 (s, 9H), 3.955 (s, 3H), 6.927 (d, 1H), 7.511 (dd, 1H), 7.818 (d, 1H), 10.592 (s, 1H).

Step 2: 3,5-di-tert-Butylsalicylic acid

This compound was prepared as described in Synthetic Communications, 37 (14), 2391-2397, (2007) with some modifications as follows: methyl 3,5-di-tert-butylsalicylate (5.5 g, 0.021 mol) was dissolved in methanol (150 mL). Potassium hydroxide (6.7 g, 0.12 mol) in water (50 mL) was added slowly in a steady stream. The resulting mixture was refluxed of 1 h. The hot solution was poured into a 1:1 mixture of ice (200 g) and 1N aqueous hydrogen chloride (200 mL) and the mixture was stirred at ambient temperature. The resulting solid was filtered and washed several times with water. The material was air dried to give 4.85 g (92% yield) of 3,5-di-tert-butylsalicylic acid as a white solid.

MS: m/z 249.1 (MH$^-$) and m/z 251.1 (MH$^+$).

123-13, Step 3: Methyl 3-chloro-4-[(3,5-di-tert-butyl-2-hydroxybenzene)amido]benzoate This compound was prepared in a similar manner as described in Example 1, step 3 from 3,5-di-tert-butylsalicylic acid (Example 92, step 2) and methyl 4-amino-3-chlorobenzoate to obtain methyl 3-chloro-4-[(3,5-di-tert-butyl-2-hydroxybenzene)amido]benzoate except the reaction mixture was taken up in ethyl acetate and washed twice with 1N aqueous hydrogen chloride, twice with saturated aqueous sodium bicarbonate and once with brine. The mixture was dried over sodium sulfate, filtered, silica gel was added and the mixture was concentrated in vacuo. The residue was transferred to a pre-column and the material was purified by chromatography using a 24 g column and initially hexanes as eluent (4 min.). The eluent was modified to 5% ethyl acetate/hexanes over a 6 min. period and kept at 5% ethyl acetate/hexanes for the remainder of the purification. The fractions containing the pure major component were combined and concentrated in vacuo to give 0.203 g (44.1% yield) of methyl 3-chloro-4-[(3,5-di-tert-butyl-2-hydroxybenzene)amido]benzoate as a white solid.

MS: m/z 416.2 (MH$^-$) and m/z 418.1 (MH$^+$).

Example 93: 3-Chloro-4-[(3,5-di-tert-butyl-2-hydroxybenzene)amido]benzoic acid

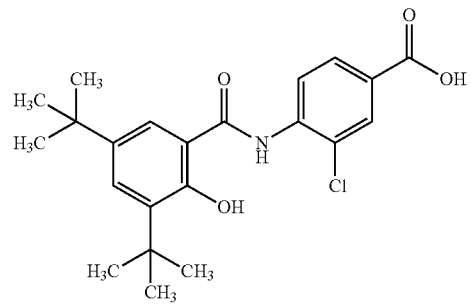 [SMILES: CC(C)(C)c1cc(C(=O)Nc2ccc(C(=O)O)cc2Cl)c(O)c(C(C)(C)C)c1]

This compound was prepared in a similar manner as described in Example 2 substituting methyl 3-chloro-4-[(3,5-di-tert-butyl-2-hydroxybenzene)amido]benzoate [Example 92] for methyl 3-chloro-4-{[2-hydroxy-5-(trifluoromethyl)benzene]amido}benzoate to give 3-chloro-4-[(3,5-di-tert-butyl-2-hydroxybenzene)amido]benzoic acid as a white solid in a quantitative yield.

MS: m/z 402.1 (MH$^-$) and m/z 404.1 (MH$^+$).

Example 94: 5-tert-Butyl-N-[2-chloro-4-(3-methyl-1,2,4-oxadiazol-5yl)phenyl]-2-hydroxybenzamide

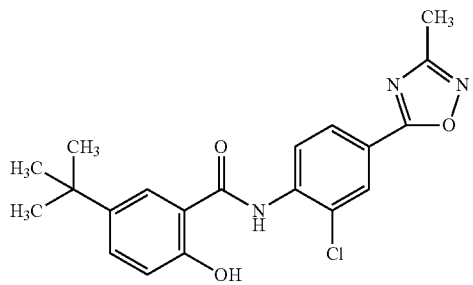 [SMILES: Cc1noc(-c2ccc(NC(=O)c3cc(C(C)(C)C)ccc3O)c(Cl)c2)n1]

5-tert-Butyl-N-[2-chloro-4-(3-methyl-1,2,4-oxadiazol-5-yl)phenyl]-2-hydroxybenzamide This compound was prepared from a procedure adopted from WO2012/125893 as follows: A mixture of 4-[(5-tert-butyl-2-hydroxybenzene)amido]-3-chlorobenzoic acid [Example 4] (0.40 g, 1.0 mmol), HOBt (0.18 g, 1.2 mmol) and EDC.HCl (0.23 g, 1.2 mmol) in DMF (7 mL) was stirred at ambient temperature for 30 min. N'-hydroxyacetimidamide (0.16 g, 2.2 mmol) was added in one portion and the mixture was stirred at ambient temperature to 50° C. for 30 min., then the mixture was heated at 125° C. for 5 h. After cooling to ambient temperature, the reaction mixture was partitioned between ethyl acetate and saturated aqueous sodium bicarbonate solution. The aqueous phase was extracted with ethyl acetate. The combined organic phase was washed with saturated aqueous sodium bicarbonate solution, twice with 30 mL each of 10% aqueous lithium chloride solution, then brine. The organic phase was dried over magnesium sulfate. The mixture was filtered, silica gel was added to the filtrate and the mixture was concentrated in vacuo. The residue was transferred to a pre-column and purified by chromatography using a 24 g column and initially hexanes as eluent (1 min.). The eluent was modified to 35% ethyl acetate/hexanes over a 9 min. period and kept at 35% ethyl acetate/hexanes for the remainder of the purification. The fractions containing the pure major component were combined and concentrated in vacuo to give 0.171 g (44.3% yield) of 5-tert-Butyl-N-[2-chloro-4-(3-methyl-1,2,4-oxadiazol-5-yl)phenyl]-2-hydroxybenzamide as an off-white solid.

MS: m/z 384.1 (MH$^-$) and m/z 386.1 (MH$^+$).

$^1$H NMR (500 MHz, DMSO-d$_6$): δ 1.292 (s, 9H), 2.418 (s, 3H), 7.016 (d, 1H), 7.537 (dd, 1H), 8.054 (d, 1H), 8.102 (dd, 1H), 8.198 (d, 1H), 8.821 (d, 1H), 11.285 (s, 1H), 11.871 (s, 1H).

Biological Examples

Fatty Liver Disease Contributes to the Metabolic Syndrome/Obesity Epidemic:

A combination of interrelated disorders associated with obesity including hyperglycemia, insulin resistance, hypertension and elevated plasma triglycerides define metabolic syndrome (MetS). Type 2 diabetes (T2D) is one manifestation of the metabolic syndrome epidemic; however, non-alcoholic fatty liver disease (NAFLD) is less appreciated as the manifestation of MetS in the liver. Normally, excess fatty acids accumulate as triglycerides in adipose tissue; however, ectopic triglyceride accumulation (in non-adipose tissue) causes lipotoxicity and impairs cellular function. By definition, NAFLD is a form of lipotoxicity characterized by excessive triglyceride deposits in the liver. NAFLD can also contribute to diabetic hyperglycemia and correlates with T2D as the vast majority of type 2 diabetics (70-90%) have some form of NAFLD. In mouse genetic models of lipodystrophy, whereby lipids cannot be deposited in adipose tissue, but instead deposit ectopically in the liver: mice develop MetS/T2D despite not even having peripheral white fat cells. One unifying therapeutic approach for NAFLD, MetS, and improving T2D is to decrease ectopic triglyceride accumulation in the liver.

Identifying Novel Compounds that Promote Hepatic Lipid Clearance In Vivo:

Currently, the most commonly used animal model of metabolic syndrome and related disorders is the C57BL/6J 60% fat diet, diet-induced obesity (MO) mouse model. This C57-D10 model mimics many aspects of Western diet associated disorders including hyperphagia/obesity, fatty liver, insulin resistance, and increased plasma fatty acids/triglycerides. Using this standard model, the phenotypic high content-high throughput screening assay can identify small molecules with efficacy in reducing triglyceride content in the liver. In proof-of-principle studies, two prototype compounds were tested in C57BL/6J mice on a 60% high-fat diet and have demonstrated substantial therapeutic value (see Preliminary Data). The present invention will provide additional scaffolds and derivatized compounds to improve potency, while reducing toxicity—toward pre-clinical development for new treatments for NAFLD.

Any new treatment for NAFLD would fulfill a large unmet medical need that will only grow larger with the T2D/MetS/obesity epidemic. Herein, a two stage approach is described for drug development for a novel chemical scaffold: 1) develop a robust structure activity relationship (SAR) for optimal therapeutic effects using validated bioassays for NAFLD in vitro; and 2) subsequent in vivo profiling of therapeutic effects, with additional biomarker discovery and validation, and preliminary PK/ADME/Tox studies towards generating a clinical candidate.

Biomarker Discovery and Validation that Informs SAR:

Several innovative technologies were employed while optimizing robust molecular and phenotypic bioassays for compound development for in vivo profiling/validation. From preliminary animal studies with compounds with in vivo efficacy, we have identified a suite of molecular biomarkers using multiple biodiscovery-based experiments including mRNA GeneChips, liver-focused taqman arrays and comparative proteomics (iTRAQ and 2D-DiGE). Biomarkers that highly correlate with liver histology improvement and decreased triglyceride content that also have mechanistic rationale include fibroblast growth factor-21 (FGF21) and carbonic anhydrase-3 (CAR3) among others. FGF21 is particularly interesting because it is actively pursued as a clinical candidate for treating diabetes (Merck/Ambrx partnership) and has demonstrated potent anti-diabetic and anti-obesity properties and exerts beneficial effects on hepatic steatosis when injected. Preliminary results indicate that our leading small molecule stimulates FGF21 expression in a PPAR-independent manner, and has dramatic potential for treating NAFLD and diabetes as an oral formulation in contrast to FGF21 that requires parenteral administration (developed by Merck/Ambrx).

We have been able to reproduce positive biomarker responses in both human liver cell lines and in primary rat hepatocytes with our innovative in vitro assay for fatty liver disease where liver cells are 'loaded' with a mixture of fatty acids to mimic microvesicular steatosis, and are then treated with test compounds to measure stimulation of lipid clearance. Compounds with positive effects in this assay are then selected for in vivo compound profiling/screening. In addition, new compounds with increased efficacy can then be used to provide new tissue samples for further biomarker discovery and validation, in an iterative manner.

Liver Biomarkers that Reflect Cellular Nutrient Status, FGF21 and Car3:

Energy balance in the liver requires a complex molecular network of regulatory mechanisms involving transcription factors, nuclear receptors, secreted molecules, cell surface receptors, and intrinsic energy metabolizing molecules. Initial in vivo studies of compounds identified previously allowed us to select and characterize biomarkers that correlate highly with therapeutic efficacy. Previous accomplishments include translating biomarkers from in vivo to in vitro bioassays that enable rapid measurement of compound effects on lipid metabolism and balance between catabolic and anabolic processes.

Among several biomarkers identified, two of the more intriguing biomarkers were FGF21 and Car3; both molecules are highly nutrient/energy responsive. FGF21 is a nutrient adaptation hormone (mainly produced by the liver and also fat) that increases lipolysis in adipose tissue and glycemic balance in the liver. Importantly, FGF21 peptide, when infused into mouse disease models improves multiple types of metabolic disorders. FGF21 re-sensitizes peripheral tissues to insulin and controls glycemia through hepatic glucose flux in obese mice. Furthermore, FGF21 reverses hepatic steatosis and obesity in high fat diet fed and ob/ob mice, respectively. The natural progression for peptide mimetic development is from native peptide proof of principle toward a modified peptide with longer acting duration in vivo. Indeed, Merck Research Laboratories have demonstrated that a PEGylated FGF21 peptide injected twice weekly also controls type 2 diabetes symptoms and hyperlipidemia in animal models.

Car3, like FGF21, also demonstrates high nutrient state responsiveness decreasing nearly 60-fold in the livers of fasted mice. Protein-depleted diets also lead to massive reductions in Car3 protein in liver cytosol. Intriguingly, although Car3 represents 30% of soluble protein in adipose tissue, "there is no convincing evidence of the primary function of the enzyme". Although Car3 is related to carbonic anhydrases by sequence, it has virtually no enzymatic activity as a carbonic anhydrase. However, Car3 is useful as a nutrient-regulated biomarker, whose expression is elevated in fat tissue of mice fed a high fat diet or 3T3 cells differentiating into 3T3-L1 fat-like cells. Car3 is also an insulin-regulated gene as its expression changes dramatically in both liver and fat in response to pancreatic beta cell death caused by streptozotocin in obese Zucker rats. Using both FGF21 and Car3 as biomarkers allows guidance of SAR drug development with potent indicators of the cellular nutrient state and insulin signaling.

Development of New Clinical Biomarkers and Diagnostics:

Current clinical serum biomarkers for liver disease do not indicate the severity of NAFLD and can entirely miss some patients with NAFLD; those patients whose ALT, AST, and GGT levels are within "normal" ranges). To develop new, more accurate clinical serum biomarkers for NAFLD, serum samples will be banked from all animals in this study to facilitate future proteomic biomarker identification (using iTRAQ/2D-DiGE and other comparative proteomics techniques).

The lack of accurate serum biomarkers for fatty liver disease requires histological evaluation to accurately assess the severity of NAFLD and evaluate therapeutic effects of drugs in vivo. In addition, accurate quantification of drug induced therapeutic benefit, even by histology, can also be challenging and laborious, requiring several highly trained individuals to independently score histology slides. A quantitative histomorphometry platform was developed to more rigorously quantify the liver lipid content/phenotype from automated/scanned slides of entire liver sections. An Aperio ScanScope slide scanner is used to scan entire histological sections for image analysis and quantification of macrovesicular and microvesicular steatosis. This quantitative histomorphometry approach is compatible with H&E, Masson's Trichrome and PAS staining. Data has demonstrated the robustness of the automated histomorphometry platform upon treatment of our leading scaffold and corresponds with manual visual scores from our staff veterinarian. Quantitative automated scoring for fatty liver is an innovation that can be commercialized independently of the drug development project to aid clinicians in accurate/unbiased and automated scoring of NAFLD severity in liver biopsy samples. This new software platform can be translated easily for human liver histology and dramatically reduce the time/cost associated with histological scoring while simultaneously improving result accuracy.

Preliminary Data:

Preliminary experiments focusing on: 1) prioritizing compounds for in vivo studies, developing initial SAR through similarity searching and high-throughput screening, 2) resynthesizing selected molecules and, 3) in vivo testing of 4-6 compounds for positive therapeutic effects for Type II Diabetes and Fatty Liver Disease were conducted. Results are summarized below.

Bioassay Analysis of Mined Similar Compounds:

A set of similar compounds were selected and evaluated in our validated high-content assay based on initial 5-scaffolds selected for exploratory studies. An average of 100 compounds per scaffold were selected for analysis in dose response and results were tabulated. Of the available similar compounds of B-127443—a substituted salicylanilide (FIG. 1), exhibited marked improvement in potency/efficacy in the bioassay panel. Screening results from other scaffolds showed a relatively "flat" SAR with no major improvements in potency among congeners. The tight correlation between human in vitro cell models and in vivo rodent studies validates the bioassay platform and our approach for NAFLD drug development.

Compound Re-Synthesis and New Analogs of B-127443:

We selected a lead scaffold earlier than anticipated and its synthetic route was amenable to analog synthesis. The first phase in developing the SAR was to identify critical substituents for modulating efficacy in the bioassays. FIG. 1 shows the R-group decomposition and an abbreviated SAR table showing FGF21 fold-change as measured by OCR.

Earlier screening of similar molecules, several structural classes showed positive activity in bioassays including FGF21 stimulation, CAR3 suppression and stimulation of lipolysis. The most potent small molecule was Niclosamide—B-127443 (Fig-I), a known FDA-approved antihelmintic. Our initial Structure-Activity Relationship (SAR) efforts was two pronged: 1) substitute R1 of the salicylic acid moiety at the 5-position, and 2) find a suitable replacement for the nitro group (R3) to avoid potentially toxicity often associated with aryl nitro groups. Replacement of the R1 group with various groups such as Methyl, H, OMe, F, and t-Butyl found that lipophilic groups, in particular the t-Butyl group greatly increased potency/efficacy. The nitro group was replaced with a carboxylic ester, carboxylic acid, cyano, Methyl and OMe groups. We found that the ester and acid groups generally led to more potent analogs. FIG. 2 shows the general synthetic route to analogs containing the ester and the acid groups.

To further investigate the salicylic acid portion of the molecule, we retained the ester and acid groups in the aniline portion of the molecule (R3 see FIG. 2) and replaced the t-Butyl group with sec-Butyl, iso-propyl, ethyl, cyclohexyl and $CF_3$ groups. The analogs possessing a sec-Butyl and $CF_3$ groups also showed enhanced activity.

With the discovery of enhanced activity of a t-Butyl group at R1 and either an ester or an acid group at R3, we began exploring the effect on activity of replacing the chloro group at the 4-position of the aniline moiety (R4 in FIG. 2). A methoxy group at this position retained activity. Recently, the analog with $OCF_3$ at the 2-position of the aniline was prepared. While not wishing to be bound to any particular theory, if this analog retains activity it may show better metabolic stability than the methoxy compound.

Finally, analogs where the hydrogen of the OH group of the salicylic acid moiety was replaced by a phosphate group or an acetyl group were prepared. While not wishing to be bound to any particular theory, the proton at this position may be necessary for activity. An analog where the OH has been replaced by OMe is currently being prepared to test this idea. While not wishing to be bound to any particular theory, the methoxy group may be more stable than the phosphate or acetyl analogs.

Biomarkers Guiding MedChem/SAR Optimization:

Having discovered pronounced differences in FGF21 and Car3 expression in entire cohorts of treated animals (FIG. 3A western blot), we developed cell-based bioassays that recapitulated the in vivo effects. The three bioassays for use in this study are: qPCR quantitation of FGF21 levels in HepG2 cells (FIG. 3B—left), qPCR quantification of Car3 in primary rat hepatocytes (FIG. 3B-right) and lipid droplet clearance in HepaRG cells (FIG. 3C).

Once these bioassays were developed, we explored the effect of B127443 and 70 structural analogs on these endpoints with positive outcomes passing to in vivo screening in an iterative process. We have found these compounds to be predictive/correlative of in vivo efficacy with adequate bioavailability. The qPCR assay confirmed that FGF21 gene expression increases in both liver and HepG2 cells confirming that HepG2s are a reliable in vitro model for FGF21 SAR development of B127443 analogs. Although Car3 is expressed at very low levels in liver-derived cell lines, it is highly expressed in rat primary hepatocytes and shows the predicted decrease in expression both at the mRNA (FIG. 3) and protein (data not shown) levels. Based on the results of both biomarkers in primary hepatocytes and cell lines, we chose the most potent analogs (B500199, B500845, B500200, B500203, B500828) for further evaluation. The effect of these 5 selected compounds on FGF21 expression levels is shown in FIG. 1/SAR table above with R-group substitutions indicated. Our current set of lead molecules has importantly eliminated the undesirable aryl nitro-group through bioisostere substitutions, while improving both in vitro and in vivo efficacy, thereby avoiding potential aryl nitro-group toxicity.

Phenotypic Lipid Clearance as a Functional Bioassay and Biomarker:

Mice deficient in components necessary to form lipid droplets are resistant to fatty liver and obesity on high fat diets and also show increased lipolysis. The in vitro models of lipid droplet metabolism involve 'lipid loading" cells with a mixture of fatty acids to establish a lipid loading capacity, and subsequent compound treatment to determine the rate of lipid clearance. We utilized this well-established assay using lipid loaded HepaRG (Life Technologies) and HepG2 cells to determine compound effects by staining neutral lipid droplets with HCS LipitoxGreen (Life Technologies) and quantitation using flow cytometry. Briefly, cells are loaded with 1:1 Oleate/Palmitate fatty acid-BSA conjugate for 24 hours in media; subsequently, cells are treated with compound for an additional 24 hours and then remaining lipid content is evaluated by flow cytometry relative to the 'not loaded" positive control. B127443, B500199, B500203, and B500828 significantly reduced lipid content as compared to untreated controls (FIG. 3C, only B-127443 shown).

Figure 4:
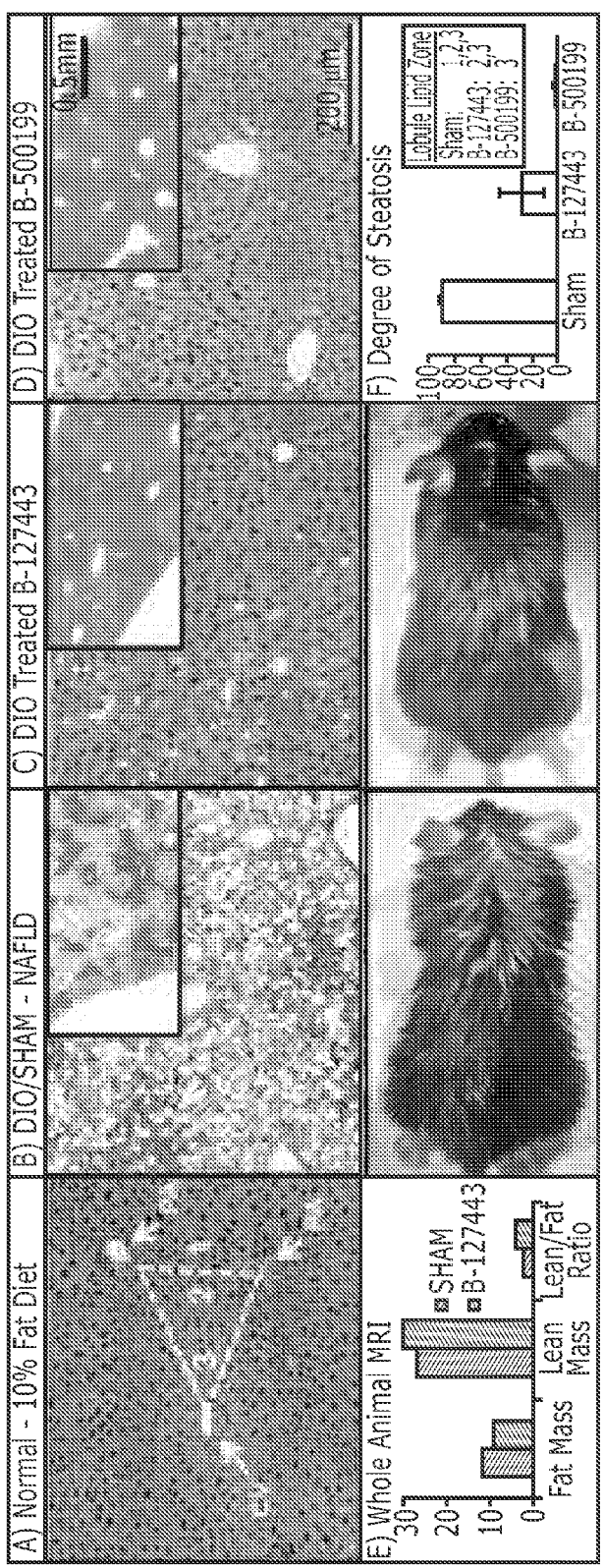
FIG. 4 presents H&E stained rodent liver sections in a once-daily, 12-day IP injection trial showing: A) normal, B) DIO sham injection group with fatty liver and C) reversal of fatty phenotype with B-127443 and D) stronger reversal of fatty liver phenotype with B-500199. E) Whole animal MRI shows significant change in lean-to-fat ratio, and animals show a dry coat effect, indicative of improved lipid metabolism. F) Degree of steatosis for treatment groups. Central vein (CV), portal area (PA) and Zones 1-3 are indicated in A). Compounds were administered IP at 10 mg/kg body weight.

Demonstration of In Vivo Efficacy for NAFLD and Hepatic Insulin Resistance:

The C57-diet induced obesity (DIO) mouse model was used in this study as a disease model for fatty liver disease and hepatic insulin resistance (FIG. 4). It was observed that eighty percent of the C57-DIO animals develop the fatty liver phenotype at 20-weeks, which highly correlates with insulin resistance penetrance and poor glycemic control. Novel compounds developed in previous studies exhibited dramatic therapeutic effects—returning the liver to a healthy state, and normalizing glucose tolerance in 12 days. In humans, progressive accumulation of hepatic triglycerides is associated with metabolic syndrome/T2D and leads to impairment of insulin action in the liver. The two guiding phenotypic indicators of test compound efficacy in earlier studies were: histological scoring of hepatic steatosis, and intraperitoneal (IP) glucose tolerance.

The initial lead compound (B-127443) was evaluated plus five novel analogs using standard histological scoring of hepatic steatosis in the C57-DIO mouse model. Singly housed mice raised on a 60%-fat diet (20-week old males purchased from Sax labs) with extensive fatty liver were treated with the test compound for 12 days via daily intraperitoneal injection (IP). Histological analysis demonstrated highly significant, striking improvement in NAFLD symptoms in liver (FIG. 4). In addition, coats of treated animals were drier (FIG. 4B vs. C), consistent with reduction in triglycerides (also observed in the DGAT1 mouse knockout with dry coat). This proof-of-principle in vivo study demonstrated dramatic therapeutic effects with B-127443 and B-500199 in C57-DIO mice with 13-500199 exhibiting a statistically significant improvement over B-127443.

Glucose tolerance testing (IP-GTT) was performed via an IP injection of a 10% glucose solution at ling/kg body weight within a 10 mL/kg body weight volume. Blood glucose was monitored pre and post injection at 15-minute intervals for 60 minutes using a standard glucometer. IP-GTT was chosen over oral GTT to bypass gut hormone signaling (GLP-1) for a more direct assessment of hepatic insulin resistance. IPGTT was performed on animals both prior to and after the 12-day test compound administration period to glean both individual animal responses and cohort averaged responses. FIG. 5 shows both cohort-averaged improvements in IP-GTT and responses in a group of three cohort tested pre and post-test compound trial.

12-days of B-127443 markedly improved IP-GTT. Interestingly, FIG. 5B shows three animals, two of which (Animals 1 & 3) are massively insulin resistant, whose IP-GTT "collapsed" down onto Animal-2, who appears resistant to the high-fat diet. Indeed, as described, some C57 animals have differences in leptin signaling, which causes them to be somewhat resistant to a high-fat diet. B-127443 and other compounds in this series can be viewed as reducing the metabolic derangements associated with a high-fat diet and could potentially also be evaluated for obesity.

Biomarker Discovery and Validation:

As a first step toward biomarker discovery we performed a number of genomic (gene chip microarrays, HepG2 liver-focused Taqman arrays), and comparative proteomic studies of sham and drug treated liver to discern potential targets of B-127443. The expression and proteomic studies were implemented with particular interest in lipid/energy metabolism pathways. Interestingly, microarray analysis revealed that B127443 significantly changed the expression of many genes involved in lipid/energy metabolism (FGF21, Fitm1, Fitm2, CideC, Cyp7A1, chn) and therefore may be used to identify relevant biomarkers/targets for fatty liver disease. Additionally, a comparative proteomics approach (2D-DiGE) revealed that livers derived from B127443-treated mice contained significantly lower levels of CAR3 protein. We were particularly interested in elevated FGF21 levels in response to B127443 since an injectable synthetic peptide of FGF21 is actively being pursued in clinical trials for treating diabetes (MercklAmbrx partnership) and has demonstrated potent antidiabetic and anti-obesity properties. We are also particularly interested in Car3, since this gene represents ~30% of soluble protein in adipose tissue, goes up in adipocytes (~2-fold) in response to high fat diet, but goes down in the liver dramatically in response to energetic starvation. Finally, Car3 is negatively regulated by insulin signaling and thus might reflect insulin sensitivity. FGF21 and Car3 are good biomarkers for liver function in response to metabolic changes. Indeed, our trials on large numbers of mice validated our initial findings that B127443 increases FGF21 expression, while decreasing Car3 expression, and also reverses lipid-loaded cells to a normal lipid phenotype (FIG. 2).

Figure 6:
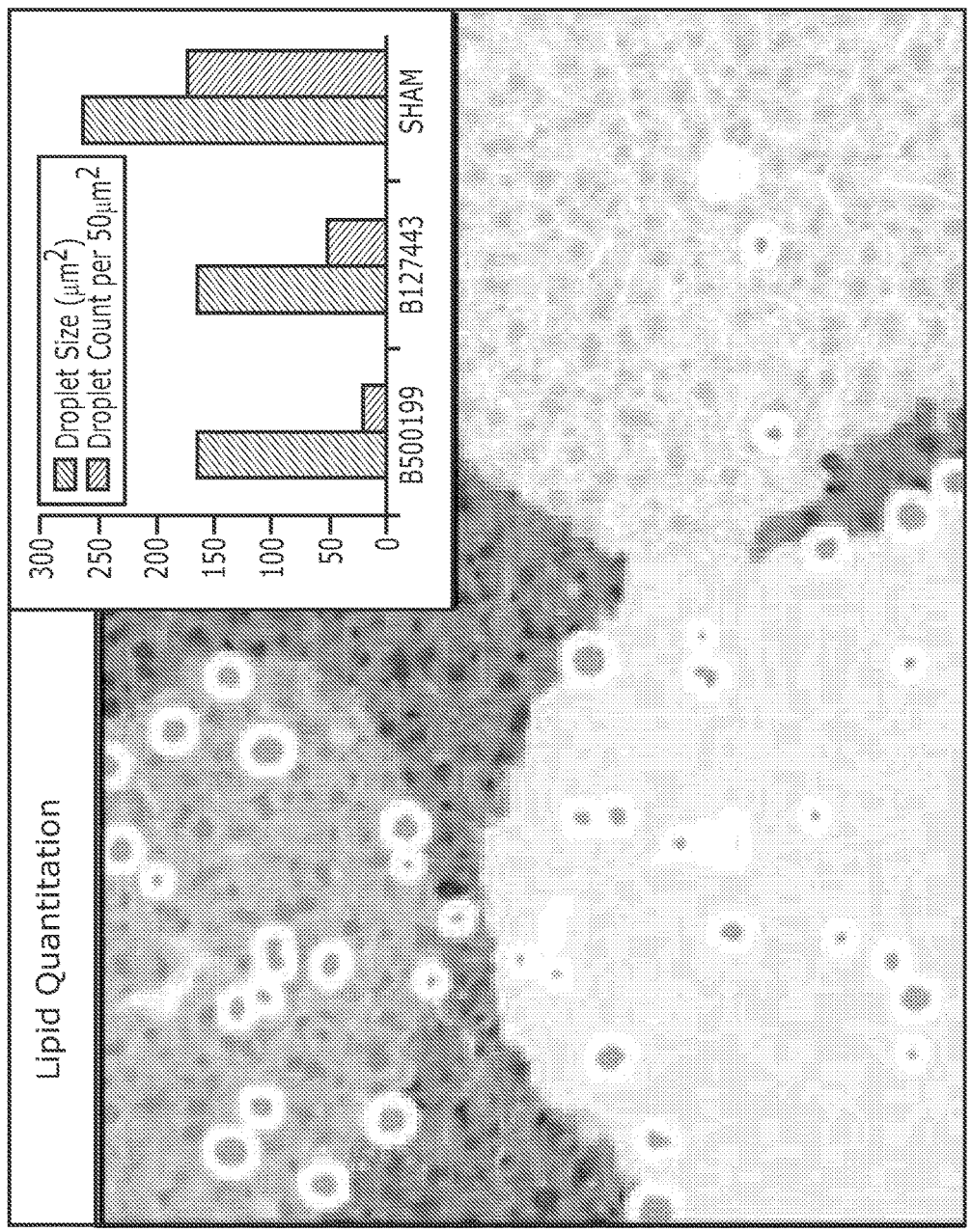
FIG. 6 shows the quantitative, automated assessment of lipid phenotype in H&E stained entire liver sections yielding a robust score for lipid accumulation. Lobule areas are individually assigned a color and identified lipid droplets are assigned green color. Inset shows tabulated lipid droplet statistics for sham vs. treatments.

Quantitative Histomorphometric Analysis Platform:

During initial animal screening, we developed a quantitative histomorphometry platform software using components of the open-source CellProfiler software for automatically quantifying/scoring liver lipid content through lipid droplet detection in entire liver sections. In brief, entire H&E liver slides are scanned at 400× total magnification using an Aperio ScanScope slide scanner. For automated lipid phenotyping, we 1) detect entire pieces of tissue, 2) identify individual lipid droplets based on size and shape and, 3) measure mean droplet size and droplet density per pm2. This automated quantitation of liver lipid phenotype, supervised and verified by a trained veterinary pathologist (PI Yi), offers an unbiased and simple method for comparing compound effects. Results from manual scoring of average degree of steatosis in cohorts are; Sham-90%, B127443-27% and are in good agreement with machine-aided scoring results as shown in FIG. 6. Note: This quantitation does not replace comprehensive manual scoring and will be used in conjunction to measure changes in the lipid phenotype including changes in size, zonal distribution and count of intracellular lipid.

Figure 7:
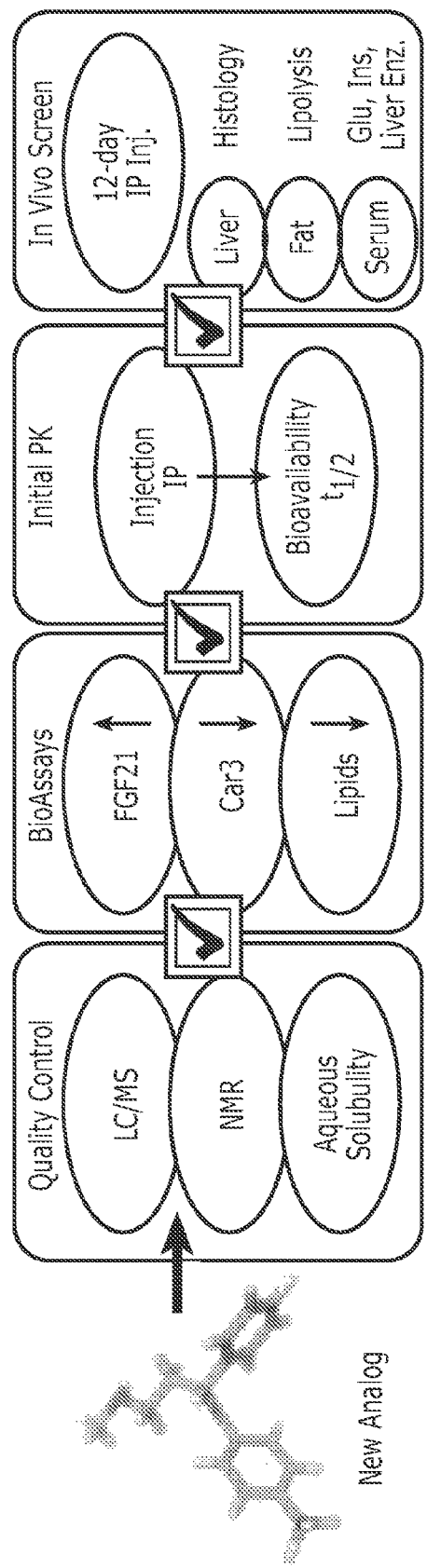
FIG. 7 presents a flow chart of compound evaluations from new analog synthesis to in vivo screening.

Further Optimization of Lead Compounds for Fatty Liver Disease Using Established Bioassays and In Vivo Screening:

Additional studies will be conducted to attain optimization of lead compounds for fatty liver disease using established bioassays and in vivo screening for efficacy in: reducing ectopic liver lipids, improving bioavailability, and minimizing toxicity. A flow chart and decision tree for synthesized compounds is shown in FIG. 7.

Optimization of Small Molecule Efficacy Through Medicinal Chemistry/SAR:

Lead compounds developed previously have significant efficacy for both fatty-liver and for type-II diabetes endpoints including reducing ectopic lipid/triglyceride accumulation in the liver, and normalizing blood glucose homeostasis in the C57-diet induced obesity animal model. In these studies, we will extensively characterize medicinal chemistry/SAR studies to fully optimize efficacy and minimize toxicity for active molecular scaffolds. Active scaffold derivatives will be tested with validated molecular/cellular bioassays including: qPCR, Western blots, and flow cytometry to measure lipid content. We will develop structure-activity relationships (SAR) to optimize select chemotype clades through chemical synthesis of novel analogs with already established therapeutic potential. Workflow will involve medicinal chemistry prioritization/evaluation, chemical synthesis of new analogs of active scaffolds, followed by assessment of dose/response through bioassays and biomarker measurements. The goal of these studies is to develop a complete SAR and identify a subset of active compounds for in vivo screening for efficacy, toxicity and appropriate DMPK properties in the C57-DIO animal model.

The initial structure activity relationship will be expanded by synthesizing and evaluating approximately 300 small molecule analogs of the lead scaffold for in vitro effects in our validated bioassays for fatty liver disease and type-II diabetes. The goal of this aim is to optimize efficacy, minimize toxicity while improving bioavailability towards the goal of producing an orally-bioavailable drug for NAFLD.

Medicinal Chemistry Approach—Data Driven SAR:

Three main R-groups (see FIG. 1, R1, R3 & R4) will be substituted to generate active analogs based on preliminary SAR with further expansion planned to additional R-groups. From preliminary studies, the activity increased dramatically upon the substitution of a—chloro to a—t-butyl group, indicating that R1 may be binding a lipophilic pocket, suggesting that we explore additional bulky non-polar R-groups. R3 substitution from a—nitro to a -methyl ester significantly improved activity primarily through increased solubility and we will explore additional ester and amid groups in this position using established coupling chemistry. We have observed a complete loss of activity when the salicylate hydroxyl group (R2) is substituted or removed, indicating that this functional group is critical for activity.

We propose to continue to expand the SAR of this class of molecules largely through parallel expansion of series about each R-group with recombination of the optimal representative of each series. We are particularly interested in replacing the ester moiety with known bioisosteres such as an amide or certain heterocycles, i.e. 1,2,4-oxadiazoles-1,2,4-triazoles or oxazolines—to improve solubility, permeability and metabolic stability. Combining salicylic acid moieties with aniline moieties have given rise to more active analogs.

Stable Isotope Analog Synthesis:

Isotopically labeled analogs will be prepared to enable comparative metabolic studies. Our strategy involves custom synthesis of $^{13}C$ labeled substituted salicylic acids starting with paraformaldehyde-$^{13}C$ and deuterium-labeled 4-aminobenzoic-2,6-$d_2$-benzoic acid for the aniline portion of the molecule, enabling metabolite tracing of both moieties.

Figure 3:
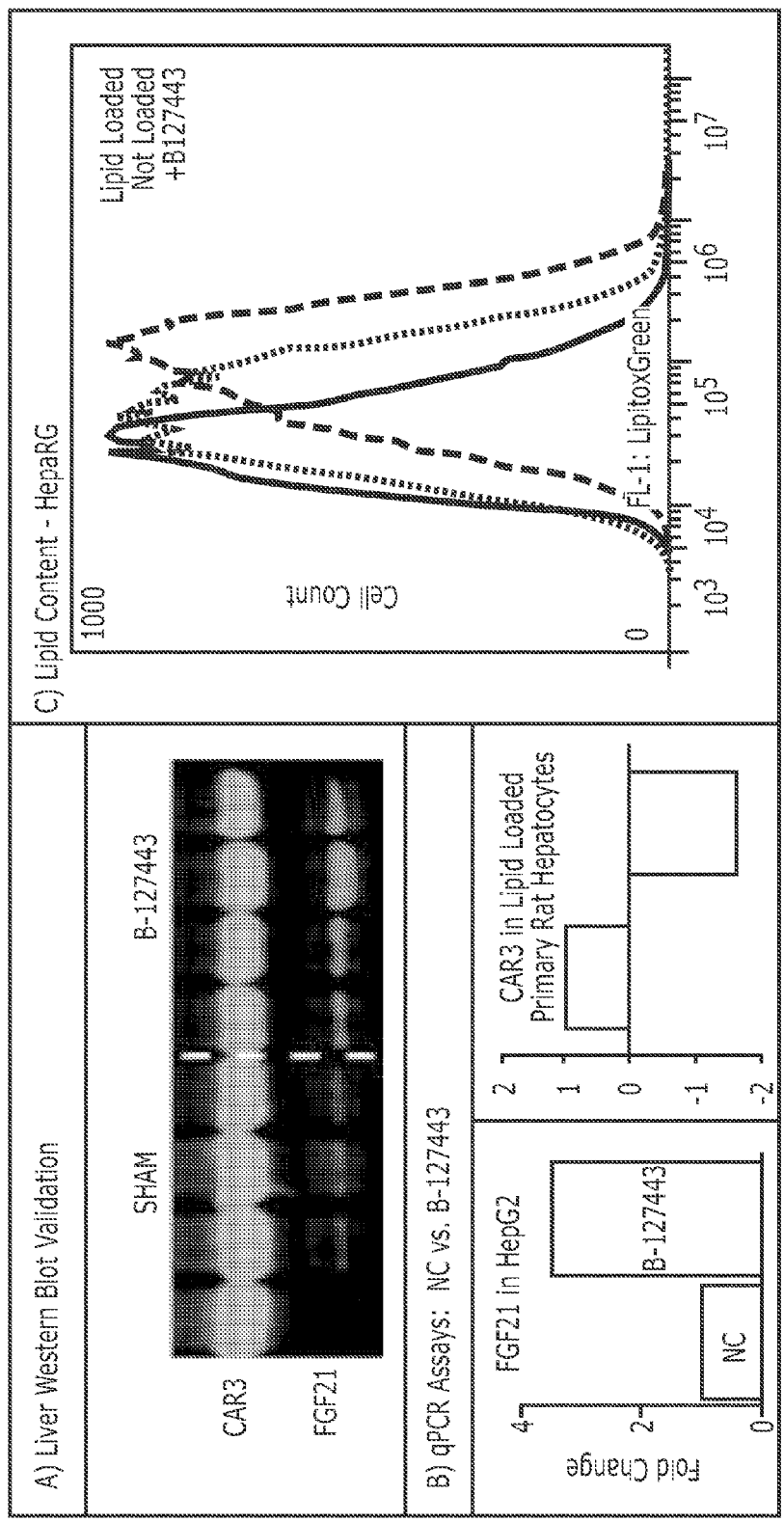
FIG. 3 shows in vivo biomarkers for NAFLD: FGF21, Car3 and lipid accumulation. A) Western blot analysis of liver from drug treated (B-127443 at 10 mg/kg) vs. vehicle treatment groups showing significant reduction in CAR3 and stimulation of FGF21 expression. B) Validated qPCR bioassay endpoints for in vitro models showing the same trend as in vivo. C) 100 nM B-127443 stimulates lipolysis in lipid-loaded liver cells.

Bioassay Evaluation of New Analogs:

New compounds will be tested in panels of validated bioassays including: 1) primary rat hepatocytes for effects on Car3 mRNA and protein, 2) HepG2 cells for FGF21 mRNA fold change, and 3) HepaRG and primary rat hepatocytes for lipid content (LipitoxGreen/flow cytometry). Following compound treatment (48 hours), both mRNA and protein will be isolated from cellular lysates. The RNA will be processed for qPCR analysis. We will probe for a number of biomarkers that are involved in lipid and energy metabolism (preliminary data) to gain mechanistic insight and to aid in planning further synthesis. The qPCR results will be verified at the protein level by Western blot analysis as we have done with FGF21 and Car3 (FIG. 3).

Compound Selection Criteria:

Compounds will be selected to advance into additional PK studies if they stimulate at least a 3-fold increase in FGF21 and/or simulate at least a 1.5-fold reduction in Car3 and stimulate lipid clearance.

Evaluate Small Molecule In Vivo Efficacy in the C57-DIO Mouse Model of NAFLD with Preliminary PK/Tox Evaluation:

The diet induced obesity (DIO) model relies on feeding C57BL/6J mice high-fat chow (60% of calories from fat) to induce numerous deleterious phenotypes including: insulin resistance, obesity, elevated blood glucose, increased plasma fatty acids and extensive fatty liver disease (FIG. 1). Our in vivo compound screening is guided by improvements in liver histopathology as the primary endpoint. Liver histology is also the gold standard for diagnosing NAFLD severity in humans due to lack of clinical diagnostics. The C57-DIO model and approach have proven successful in our proof-of-concept studies to find efficacious compounds (B127443 and B500199) and novel biomarkers. For up to 100 compounds with positive bioassay results, we will perform basic pharmacokinetic studies to ensure bioavailability in the blood compartment with hopes of identifying 50 compounds for detailed in vivo profiling. In addition to liver histology, routine blood chemistry assays for insulin, blood glucose, liver enzymes (toxicity) and fatty acids/triglycerides will also be conducted following compound treatment to further elaborate therapeutic mechanisms. Importantly, animals with improved liver histology will provide tissue and serum samples to serve as sources for future additional biomarker discovery. Animals will be monitored closely for signs of distress and discomfort as initial signs of compound toxicity.

Experimental Design: In Vivo Screening for NAFLD and T2D:

An overview of our pipeline for compound screening is shown in FIG. 4. Selected compounds will be profiled for bioavailability using a simplified IP pharmacokinetic protocol (3-normal animals, 3 time points) to estimate serum concentration of the parent compound using triple-quad LC/MS/MS. Compounds with a minimum 4-hour half-life and comparable IP bioavailability will be selected for screening. This will ensure new compounds enter the blood compartment and that negative histology results are due to lack of efficacy rather than poor bioavailability. We anticipate screening 50 compounds in vivo with adequate PK and for full liver histopathology analysis. Compounds with bioavailability comparable or greater than the initial parent compound (B-127443) will be selected for animal screening.

A Two-Sample T-Test was performed to determine the sample size with a power of 0.9 using average sigma values for physiological measurements (like serum concentrations of glucose, insulin, triglycerides, etc), which are small due to the inbred strain. This power analysis yielded n=10 for each cohort. Cohorts often 20-week old C57-D10 mice will be purchased directly from JAX labs and will be pre-screened for abnormal body weight, insulin or blood glucose. (Not all C57 mice respond equally to DIO and therefore must be pre-selected to eliminate outliers from further study.) We will administer test compounds via IP injection at 10 mg/kg/day for a 12-day period, since this protocol gives robust responses for both B127443 and B500199. All necessary assurances will be made as defined in the IACUC guidelines for humane endpoints if substantial compound toxicity is observed. During the course of compound screening, we will monitor baseline and ongoing fasting blood glucose (enzymatic/fluorescent, in 0.5 microliter serum), insulin (ELISA, in 2 microliter serum), and non-esterified free fatty acids (NEFA, in 4 microliter serum) from serum collected from a tail nick. We have developed and miniaturized these assays in-house in 384-well format so that we can monitor these endpoints in live animals requiring periodic tail-nicks, substantially reducing animal numbers and cost. At the end of the 12-day IP injection trial, the animals will be humanely euthanized to collect liver, pancreas, epididymal fat pad (and other organs) and blood for analysis of histology, lipolysis and blood chemistry. Specimens collected in this study will prove invaluable for future proteomic identification of serum and liver biomarkers of NAFLD.

Analytical Methods for NAFLD/Diabetes Endpoints:

Liver tissue will be collected and aliquoted for various purposes including histological evaluation (see below), western blot, expression profiling and quantitation of triglycerides per gram of liver tissue. This simple biochemical triglyceride determination (kit from ZenBio Inc, RTP, NC) is a rapid/robust indication of the extent of lipid accumulation and highly correlates with the steatosis score from histological analysis. Routine pre- and post-treatment glucose tolerance testing will be performed along with HbA1C (percent glycated hemoglobing—A1C-now point-of-care kit available as a real-time, portable test from Bayer), insulin and NEFA in-house. The Yale mouse metabolic phenotyping center will be used for serum chemistry assays as fee for service including the comprehensive serum metabolic panel (many endpoints including lipid panel (6-assays) and liver function (7-assays)).

Histological Evaluation of NAFLD and Liver Toxicity:

After mice are humanely euthanized, the entire liver will be excised, weighed and liver color (yellow color indicates moderate to severe fatty liver) will be evaluated immediately. Other tissues/organs will be harvested and reserved for future/retrospective analyses. Following fixation, paraffin embedding, sectioning, and staining of liver tissue with hematoxylin and eosin, histological examination will be performed using the standardized histological scoring system for NAFLD. Degrees of steatosis and lobular inflammation are graded 0 to 3. Fatty infiltration is classified as microvesicular, macrovesicular, or mixed and the location (Zone 1-3 or atonal) is recorded. Additional findings, such as fibrosis (using Mason's trichrome staining) and hepatocellular ballooning will also be recorded, but are not anticipated and have not been observed for this series of compounds at up to 25 mg/kg body weight. Additionally, automated quantitative histomorphometry will be performed on entire H&E stained sections to extract the global lipid phenotype including cell size, average lipid droplet number per zone and per cell, and total lipid content per area.

Evaluation of Oral Bioavailability:

Selected compounds showing improvements in efficacy (~50) with adequate IP bioavailability will be tested for oral bioavailability to further the underlying goal of producing an orally bioavailable, once-daily treatment for NAFLD and potentially for insulin resensitization that could be administered in conjunction with Metformin. Fed animals will be administered with a standard dose of 10 mg/kg body weight (in saline) of the test compound in 0.01 mL/g body weight by oral gavage using a ball-tipped needle. Blood samples will be obtained at 2, 5, 10, 20, and 40 minutes and 1, 2, 3, 4, 6 and 8 hours post-dose administration. The administered compound serum concentration will be quantitated as in IP-bioavailability studies using LC/MS/MS.

Toxicity/Metabolic Profiling in Primary Human Hepatocytes and Ex Vivo Liver:

Although compounds pursued in this study have proven in vivo efficacy in mouse models of fatty liver disease and type 2 diabetes, these compounds must be evaluated for toxicity in primary human liver cells and tissues prior to advancing to clinical candidacy. In this study, we will utilize Baylor Hospital's tissue procurement and cGMP tissue processing infrastructure/expertise to evaluate toxicity and small molecule metabolism for the most promising molecules from earlier studies. Up to 10 compounds will be profiled for toxicity and comparative metabolism in primary human hepatocytes derived from multi-donor organs. 2-3 selected compounds will then be evaluated in the state-of-the-art ex vivo liver perfusion model for predicting drug-induced liver injury in a dose-escalation study. Although more expensive than animal studies, 22% of clinical trials end due to drug-induced liver injury; therefore, profiling toxicity and drug metabolism in this ex vivo human assay will help ensure success in future clinical studies if no toxicity is observed.

Experimental Design: In Vitro Cellular Testing Using Primary Human Hepatocytes:

Primary human hepatocytes will be isolated from cadaveric donor healthy livers that are procured for the purpose of liver transplant. The Annual Data Report of the US Organ Procurement and Transplantation Network for 2011 showed that about 13.5% of livers procured from qualified deceased donors are discarded due to several reasons that include damage during surgery or biopsy findings documenting fatty liver. Baylor Simmons Transplant Institute is linked with two major organ procurement organizations (OPO) in Texas: Southwest Transplant Alliance and LifeGift. Together these two OPOs were responsible for procuring 398 livers in the year 2011 out of which 22 were not used for transplants. We propose that such discarded healthy livers be used for this study to isolate primary hepatocytes and for ex vivo experiments. The process of isolation of hepatocytes primarily involves digestion of liver tissue with collagenase enzyme followed by purification using percoll gradients. The isolated hepatocytes will be cultured for up to 7 days with intact function as determined by urea and albumin production. Baylor's research team has several years of experience processing tissue under cGMP conditions for transplantation and research purposes and no difficulty is expected in isolating primary hepatocytes for the experiments proposed below. We propose to use ten livers per year from healthy donors.

Initial experiments will separately test efficacy and toxicity of up to 10 selected compounds on primary hepatocytes in culture at several doses at and above the in vitro EC50 established in select bioassays. For efficacy testing, compounds will be tested for lipid-clearing effects in hepatocytes cultured in DMEM in the presence or absence (control) of high concentration of FFA mixture (palmitic & oleic acids with albumin as a carrier) consistent with the HepaRG/rat hepatocyte experiments. For toxicity testing, hepatocytes will be measured using standard Hoechst/propidium iodide staining for viability by flow cytometry. Cell morphology will be assessed by staining for Cytokeratin 18 (hepatocellular marker), Cytokeratin 19 (epithelial cell marker) and EpCAM (hepatic progenitor marker). Induction of apoptosis will be measured by flow cytometry using a validated multiplexed assay including FLICA-caspase 3/7 activation, Annexin-5 and mitochondrial membrane potential. Cell function will be determined by urea and albumin production. Importantly, alteration of lipid metabolism will be analyzed for consistency in biomarker changes including CARS, FGF21.

Ex Vivo Perfusion Dose-Escalation Study to Measure Compound Toxicity/Metabolism:

2-3 compounds selected from previous studies for in vivo efficacy and negligible toxicity in other hepatocyte studies will be assessed using an ex vivo perfusion model with human liver tissue. This model is an alternative means of evaluating safety and efficacy of new compounds for hepatocyte lipid metabolism in a pre-clinical study. The benefits include preservation of three-dimensional organ architecture, and physiological phase I and II metabolism of cytochrome P450 and uridine diphosphate glucuronosyltransferase (UGT) lacking in cultured hepatocytes or liver-derived cell lines. The ex vivo model, however, cannot mimic the in vivo environment because of the lack of blood supply, immune function, and communication with other tissues. The ex vivo perfusion system has been validated as an appropriate model for drug-induced liver damage and is similar to the perfusion circuit used in human pancreatic islet isolation.

Multiple cadaveric livers from a diverse segment of the population will be used to detect signs of toxicity and for comparative metabolism in a dose escalation study. Basic characteristics of donors such as age, height, body weight, and medication are also available for this study. We will test selected stable isotopically labeled compounds in the ex vivo perfusion model at three doses above the comparable efficacious dose from rodent studies. Livers will be divided into several pieces by a Baylor liver transplant surgeon (approximately 50 grams per each group) and will be attached to ex vivo circulation systems for 6 hours. Tissue from the same donor will be simultaneously tested in control/vehicle, and escalating dosage groups for comparative metabolic analysis and to detect the onset of adverse effects. During the experiment, we will collect circulating culture media every hour. The collected samples will be evaluated for liver function by measuring outputs including: glucose, lactose, urea, bile acids, AST, ALT, LDH, GGT and cytochrome P450 products. Additionally, culture media will be analyzed for isotopically labeled metabolites of test compounds using LC/MS/MS (see Aim 1 approach—stable isotopes).

Tissue sections will be evaluated before and after the ex vivo culture with immunohistochemical staining for markers of cell damage (including cleaved caspase-3 (apoptosis)) and inflammation). A Baylor hospital pathologist to assess general state of each liver will score H&E stained sections for NAFLD. Histomorphometric analysis for macrovesicular and microvesicular steatosis will also be performed on the tissue sections as described earlier, and sections will also be scored for lipid clearance. The perfusate will also be analyzed by metabolomic profiling (by Metabolon Inc., Durham, N.C.) which could give insight into any efficacy differences between compounds. Thus, the ex vivo model can help establish the safety of test compounds and possibly measure efficacy for ultimate selection of a clinical candidate.

The foregoing is illustrative of the present invention, and is not to be construed as limiting thereof. The invention is defined by the following claims, with equivalents of the claims to be included therein.

That which is claimed is:

1. A compound of Formula II:

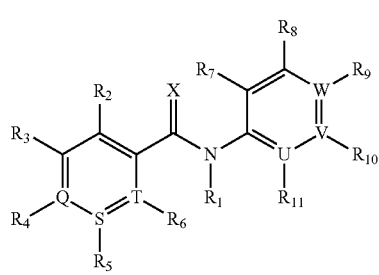

wherein:
X is O;
Q, S, T, U, V, and W are CH;
$R_1$ is hydrogen;
$R_2$, $R_4$, $R_5$, $R_7$, $R_8$, and $R_{10}$ are H;
$R_3$ is $C_{1-6}$ alkyl, which is unsubstituted;
$R_6$ is OH;
$R_9$ is $CO_2R^a$, wherein $R^a$ is hydrogen or $C_{1-6}$ alkyl, which is unsubstituted;
$R_{11}$ is Br or Cl; or a pharmaceutically acceptable salt thereof.

2. The compound of claim 1 selected from the group consisting of:

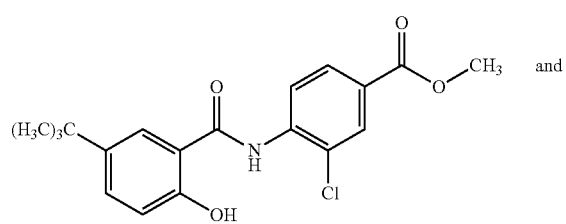

and

-continued

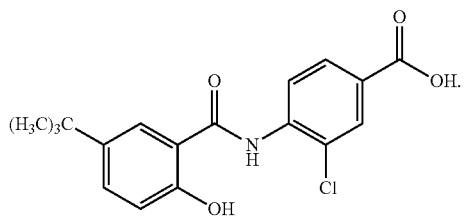
4

3. A compound having the following structure:

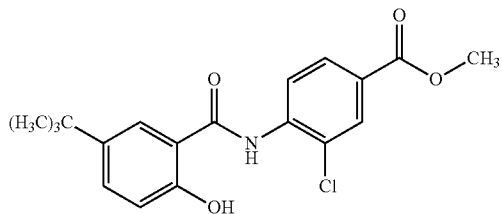
3

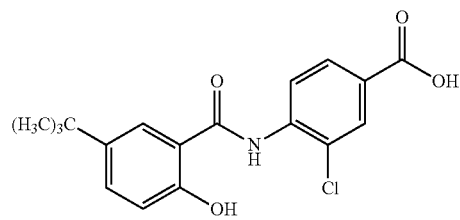
4

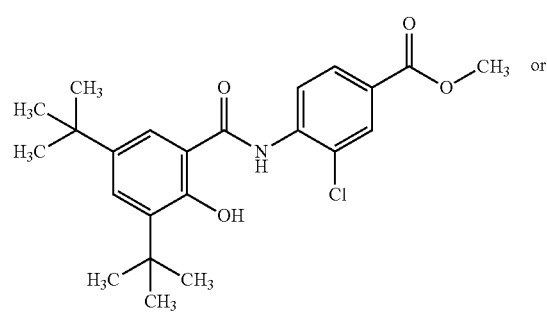
92

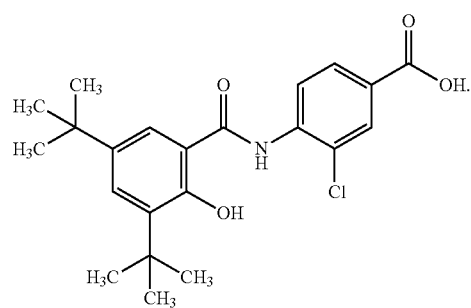
93

4. A pharmaceutical composition comprising one or more pharmaceutically acceptable carriers and a compound of claim 1, or a pharmaceutically acceptable salt thereof.

5. The pharmaceutical composition comprising an effective amount of a compound of claim 1, or a pharmaceutically acceptable salt thereof, in combination with a pharmaceutically acceptable carrier and one or more hypoglycemic agents.

6. The pharmaceutical composition of claim 5, wherein the hypoglycemic agent is selected from the group consisting of insulin, biguanidines, sulfonylureas, insulin secretagogues, α-glycosidase inhibitors, and β$_3$-adrenoreceptor agonists.

7. A method of treating a disease in which glutamate dehydrogenases are involved comprising the administration to a subject in need thereof of an effective amount of a compound of claim 1.

8. The method of claim 7, wherein the disease is non-alcoholic fatty liver disease.

9. The compound of claim 3, wherein the compound has the following structure:

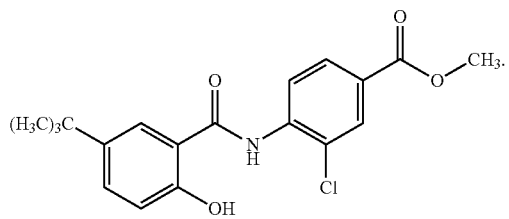
3

10. The compound of claim 3, wherein the compound has the following structure:

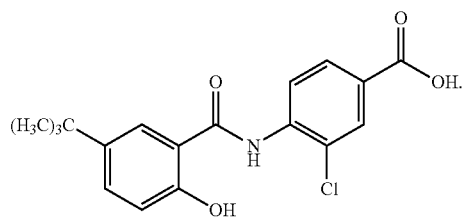
4

11. The compound of claim 3, wherein the compound has the following structure:

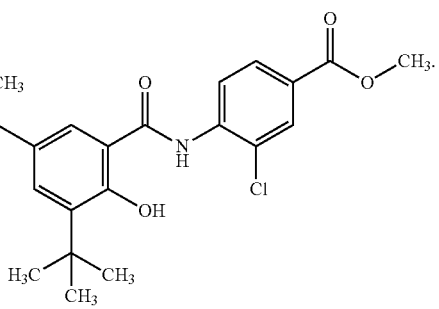
92

12. The compound of claim 3, wherein the compound has the following structure:

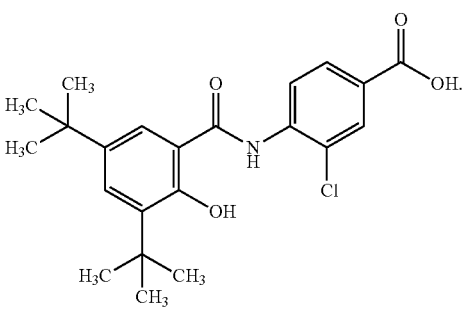
93

13. A pharmaceutical composition comprising one or more pharmaceutically acceptable carriers and a compound selected from the group consisting of one of the following:

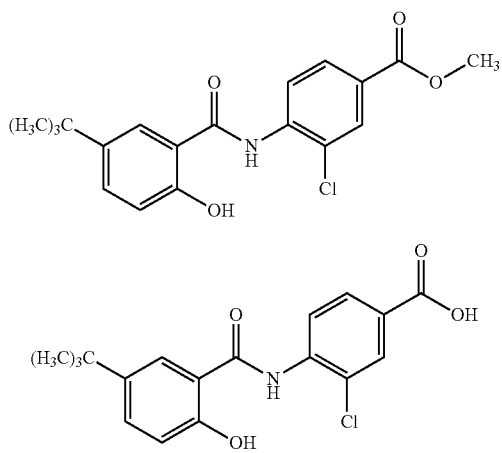

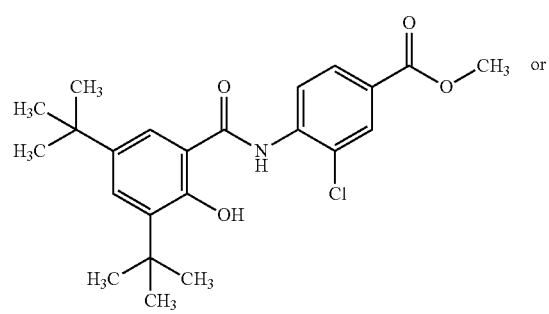

or

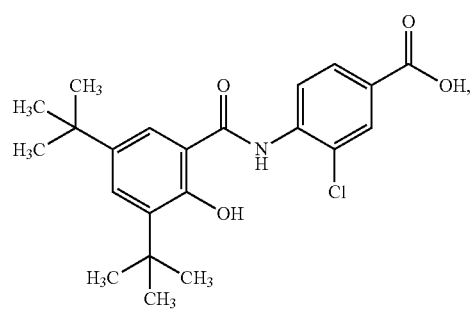

or a pharmaceutically acceptable salt thereof.

14. The method of claim 7, wherein the disease is fatty liver disease.

15. The method of claim 7, wherein the compound is

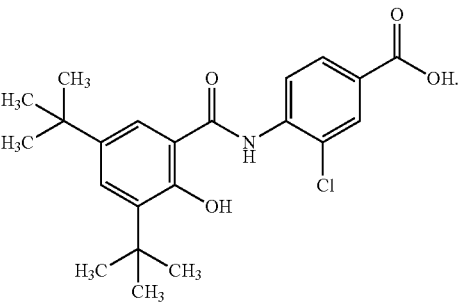

16. The method of claim 7, wherein the compound is

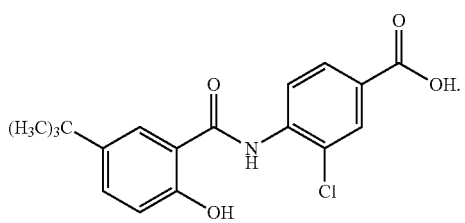

17. The compound of claim 1, wherein $R_{11}$ is Br.

18. The compound of claim 1, wherein $R_{11}$ is Cl.

19. The pharmaceutical composition of claim 13 further comprising one or more hypoglycemic agents.

20. The pharmaceutical composition of claim 19, wherein the hypoglycemic agent is selected from the group consisting of insulin, biguanidines, sulfonylureas, insulin secretagogues, α-glycosidase inhibitors, and β$_3$-adrenoreceptor agonists.

* * * * *